United States Patent
Heald

(10) Patent No.: US 9,206,174 B2
(45) Date of Patent: *Dec. 8, 2015

(54) 5-ANILINOIMIDAZOPYRIDINES AND METHODS OF USE

(71) Applicant: Genentech, Inc., South San Francisco, CA (US)

(72) Inventor: Robert Heald, Essex (GB)

(73) Assignee: Genentech, Inc., South San Francisco, CA (US)

( * ) Notice: Subject to any disclaimer, the term of this patent is extended or adjusted under 35 U.S.C. 154(b) by 306 days.

This patent is subject to a terminal disclaimer.

(21) Appl. No.: 13/759,850

(22) Filed: Feb. 5, 2013

(65) Prior Publication Data

US 2013/0150584 A1    Jun. 13, 2013

Related U.S. Application Data

(60) Continuation of application No. 13/586,147, filed on Aug. 15, 2012, now abandoned, which is a continuation of application No. 13/041,735, filed on Mar. 7, 2011, now Pat. No. 8,288,408, which is a division of application No. 12/432,529, filed on Apr. 29, 2009, now Pat. No. 7,923,456, which is a continuation of application No. PCT/US2008/087482, filed on Dec. 18, 2008.

(51) Int. Cl.
| | | |
|---|---|---|
| *C07D 471/04* | (2006.01) | |
| *C07D 235/00* | (2006.01) | |
| *C07D 401/04* | (2006.01) | |
| *C07D 487/04* | (2006.01) | |

(52) U.S. Cl.
CPC ............ *C07D 471/04* (2013.01); *C07D 235/00* (2013.01); *C07D 401/04* (2013.01); *C07D 487/04* (2013.01)

(58) Field of Classification Search
CPC ... C07D 235/00; C07D 247/02; C07D 401/04
See application file for complete search history.

(56) References Cited

U.S. PATENT DOCUMENTS

| | | | |
|---|---|---|---|
| 5,688,949 A | 11/1997 | Inoue et al. | |
| 2005/0049276 A1 | 3/2005 | Kaufman et al. | |
| 2005/0153942 A1 | 7/2005 | Wallace et al. | |

FOREIGN PATENT DOCUMENTS

| | | |
|---|---|---|
| IE | 35118 B1 | 11/1975 |
| JP | B S55-004105 | 11/1975 |
| JP | 2002-534510 | 7/2000 |
| JP | 2002020386 | 1/2002 |
| JP | 2002020386 A | 1/2002 |
| JP | 2006-525997 | 11/2004 |
| JP | 2007-504241 | 3/2005 |
| WO | 92/18504 A1 | 10/1992 |
| WO | 00/42022 A1 | 7/2000 |
| WO | 02/06216 A2 | 1/2002 |
| WO | 02/06216 A3 | 1/2002 |
| WO | 02/06231 A2 | 1/2002 |
| WO | 02/06231 A3 | 1/2002 |
| WO | 03/077855 A2 | 9/2003 |
| WO | 03/077855 A3 | 9/2003 |
| WO | 03/077914 A1 | 9/2003 |
| WO | 2004/099204 A1 | 11/2004 |
| WO | 2005/023759 A2 | 3/2005 |
| WO | 2005/023759 A3 | 3/2005 |
| WO | 2006/058752 A1 | 6/2006 |

OTHER PUBLICATIONS

International Search Report and Written Opinion for International Patent Application No. PCT/US2008/087482.
Cross and Sinha, "Meat-related mutagens/carcinogens in the etiology of colorectal cancer" Enviromental and Molec Mutagenesis 44:44-55 (2004).
Marlins et al., "The etiology of breast cancer" Cancer 71:3036-3043 (1993).
Sebolt-Leopold et al., "Blockage of the MAP kinase pathway suppresses growth of colon tumors in vivo" Nat Med 5(7):810-816 (Jul. 1999).
Price, B., "Putative allosteric MEK1 and MEK2 inhibitors" Expert Opinther Patents 18(6):603-627 (2008).
Sebolt-Leopold et al., "Blockade of the MAP kinase pathway suppresses growth of colon tumors in vivo" Nat Med 5(7):810-816 (Jul. 1999).
Malins et al., "The etiology of breast cancer" Cancer 71:3036-3043 (1993).
Hoshino et al., "Constitutive activation of the 41-/43-kDa mitogen-activated protein kinase signaling pathway in human tumors" Oncogene 18:813-822 (1999).
Cross and Sinha "Meat-related mutagens/carcinogens in the etiology of colorectal cancer" Enviromental and Molec Mutagenesis 44:44-55 (2004).
Lewis et al., "Signal transduction through MAP kinase cascades" Adv Cancer Res 74:49-139 (1998).
Interanational Search Report and Written Opinion for International Patent Application No. PCT/US/2008/087482.

*Primary Examiner* — Samira Jean-Louis
(74) *Attorney, Agent, or Firm* — Todd M. Crissey; Genentech, Inc.

(57) ABSTRACT

The invention relates to a method of inhibiting abnormal cell growth or treating a hyperproliferative disorder in a mammal comprising administering to said mammal a therapeutically effective amount of an imidazopyridine of formula I with anti-hyperproliferative activity.

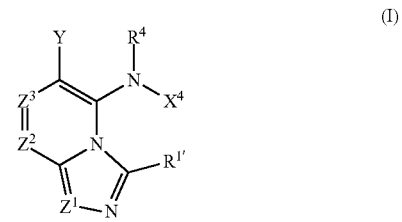

(I)

2 Claims, No Drawings

5-ANILINOIMIDAZOPYRIDINES AND METHODS OF USE

CROSS REFERENCE TO RELATED APPLICATIONS

This application is a continuation of U.S. Ser. No. 13/586,147, filed Aug. 15, 2012 which is a continuation of U.S. Ser. No. 13/041,735, filed Mar. 7, 2011 which is a divisional application of U.S. Pat. No. 7,923,456, issued Apr. 12, 2011, which claims the benefit of priority to international application number PCT/US2008/087482 and to U.S. provisional Application Ser. No. 61/015,129, filed 19 Dec. 2007, and to U.S. provisional Application Ser. No. 61/054,014, filed 16 May 2008, the disclosures of all are incorporated herein by reference in their entirety.

FIELD OF THE INVENTION

The invention relates to imidazopyridines with anti-cancer activity and more specifically to imidazopyridines which inhibit MEK kinase activity. The invention also relates to methods of using the compounds for in vitro, in situ, and in vivo diagnosis or treatment of mammalian cells, or associated pathological conditions.

BACKGROUND OF THE INVENTION

In the quest to understand how Ras transmits extracellular growth signals, the MAP (mitogen-activated protein) kinase (MAPK) pathway has emerged as the crucial route between membrane-bound Ras and the nucleus. The MAPK pathway encompasses a cascade of phosphorylation events involving three key kinases, namely Raf, MEK (MAP kinase kinase) and ERK (MAP kinase). Active GTP-bound Ras results in the activation and indirect phosphorylation of Raf kinase. Raf then phosphorylates MEK1 and 2 on two serine residues (S218 and S222 for MEK1 and S222 and S226 for MEK2) (Ahn et al., *Methods in Enzymology* 2001, 332, 417-431). Activated MEK then phosphorylates its only known substrates, the MAP kinases, ERK1 and 2. ERK phosphorylation by MEK occurs on Y204 and T202 for ERK1 and Y185 and T183 for ERK2 (Ahn et al., *Methods in Enzymology* 2001, 332, 417-431). Phosphorylated ERK dimerizes and then translocates to the nucleus where it accumulates (Khokhlatchev et al., *Cell* 1998, 93, 605-615). In the nucleus, ERK is involved in several important cellular functions, including but not limited to nuclear transport, signal transduction, DNA repair, nucleosome assembly and translocation, and mRNA processing and translation (Ahn et al., *Molecular Cell* 2000, 6, 1343-1354). Overall, treatment of cells with growth factors leads to the activation of ERK1 and 2 which results in proliferation and, in some cases, differentiation (Lewis et al., Adv. Cancer Res. 1998, 74, 49-139).

There has been strong evidence that genetic mutations and/or overexpression of protein kinases involved in the MAP kinase pathway lead to uncontrolled cell proliferation and, eventually, tumor formation, in proliferative diseases. For example, some cancers contain mutations which result in the continuous activation of this pathway due to continuous production of growth factors. Other mutations can lead to defects in the deactivation of the activated GTP-bound Ras complex, again resulting in activation of the MAP kinase pathway. Mutated, oncogenic forms of Ras are found in 50% of colon and >90% pancreatic cancers as well as many others types of cancers (Kohl et al., Science 1993, 260, 1834-1837). Recently, bRaf mutations have been identified in more than 60% of malignant melanoma (Davies, H. et al., Nature 2002, 417, 949-954). These mutations in bRaf result in a constitutively active MAP kinase cascade. Studies of primary tumor samples and cell lines have also shown constitutive or over-activation of the MAP kinase pathway in cancers of pancreas, colon, lung, ovary and kidney (Hoshino, R. et al., Oncogene 1999, 18, 813-822).

MEK has emerged as an attractive therapeutic target in the MAP kinase cascade pathway. MEK, downstream of Ras and Raf, is highly specific for the phosphorylation of MAP kinase; in fact, the only known substrates for MEK phosphorylation are the MAP kinases, ERK1 and 2. Inhibition of MEK has been shown to have potential therapeutic benefit in several studies. For example, small molecule MEK inhibitors have been shown to inhibit human tumor growth in nude mouse xenografts, (Sebolt-Leopold et al., *Nature-Medicine* 1999, 5 (7), 810-816); Trachet et al., AACR Apr. 6-10, 2002, Poster #5426; Tecle, H. IBC 2.sup.nd International Conference of Protein Kinases, Sep. 9-10, 2002), block static allodynia in animals (WO 01/05390 published Jan. 25, 2001) and inhibit growth of acute myeloid leukemia cells (Milella et al., *J Clin Invest* 2001, 108 (6), 851-859).

Several small molecule MEK inhibitors have also been discussed in, for example, WO02/06213, WO 03/077855 and WO03/077914. There still exists a need for new MEK inhibitors as effective and safe therapeutics for treating a variety of proliferative disease states, such as conditions related to the hyperactivity of MEK, as well as diseases modulated by the MEK cascade.

SUMMARY OF THE INVENTION

The invention relates generally to imidazopyridines of formula I (and/or solvates, hydrates and/or salts thereof) with anti-cancer and/or anti-inflammatory activity, and more specifically with MEK kinase inhibitory activity. Certain hyperproliferative and inflammatory disorders are characterized by the modulation of MEK kinase function, for example by mutations or overexpression of the proteins. Accordingly, the compounds of the invention and compositions thereof are useful in the treatment of hyperproliferative disorders such as cancer and/or inflammatory diseases such as rheumatoid arthritis.

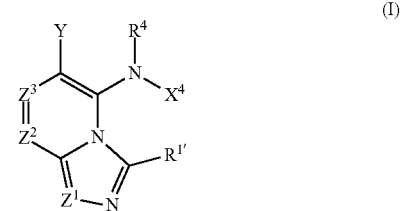

and salts thereof, wherein:

$Z^1$ is $CR^1$ or N;

$R^1$ is H, $C_1$-$C_3$ alkyl, halo, $CF_3$, $CHF_2$, CN, $OR^A$ or $NR^AR^A$;

$R^{1'}$ is H, $C_1$-$C_3$ alkyl, halo, $CF_3$, $CHF_2$, CN, $OR^A$, or $NR^AR^A$;

wherein each $R^A$ is independently H or $C_1$-$C_3$ alkyl;

$Z^2$ is $CR^2$ or N;

$Z^3$ is $CR^3$ or N; provided that only one of $Z^1$, $Z^2$ and $Z^3$ can be N at the same time;

$R^2$ and $R^3$ are independently selected from H, halo, CN, $CF_3$, —$OCF_3$, —$NO_2$, —$(CR^{14}R^{15})_nC(=Y')R^{11}$, —$(CR^{14}R^{15})_nC(=Y')OR^{11}$, —$(CR^{14}R^{15})_nC(=Y')$ $NR^{11}R^{12}$, $-(CR^{14}R^{15})_nNR^{11}R^{12}$, $-(CR^{14}R^{15})_nOR^{11}$, $-(CR^{14}R^{15})_nSR^{11}$, $-(CR^{14}R^{15})_nNR^{12}C(=Y')R^{11}$, $-(CR^{14}R^{15})_nNR^{12}C(=Y')OR^{11}$, $-(CR^{14}R^{15})_nNR^{13}C(=Y')NR^{11}R^{12}$, $-(CR^{14}R^{15})_nNR^{12}SO_2R^{11}$, $-(CR^{14}R^{15})_nOC(=Y')R^{11}$, $-(CR^{14}R^{15})_nOC(=Y')OR^{11}$, $-(CR^{14}R^{15})_nOC(=Y')NR^{11}R^{12}$, $-(CR^{14}R^{15})_nOS(O)_2(OR^{11})$, $-(CR^{14}R^{15})_nOP(=Y')(OR^{11})(OR^{12})$, $-(CR^{14}R^{15})_nOP(OR^{11})(OR^{12})$, $-(CR^{14}R^{15})_nS(O)R^{11}$, $-(CR^{14}R^{15})_nS(O)_2R^{11}$, $-(CR^{14}R^{15})_nS(O)_2NR^{11}R^{12}$, $-(CR^{14}R^{15})_nS(O)(OR^{11})$, $-(CR^{14}R^{15})_nS(O)_2(OR^{11})$, $-(CR^{14}R^{15})_nSC(=Y')R^{11}$, $-(CR^{14}R^{15})_nSC(=Y')OR^{11}$, $-(CR^{14}R^{15})_nSC(=Y')NR^{11}R^{12}$, $C_1$-$C_{12}$ alkyl, $C_2$-$C_8$ alkenyl, $C_2$-$C_8$ alkynyl, carbocyclyl, heterocyclyl, aryl, and heteroaryl;

$R^4$ is H, $C_1$-$C_6$ alkyl or $C_3$-$C_4$ carbocyclyl;

Y is W—C(O)— or W';

W is

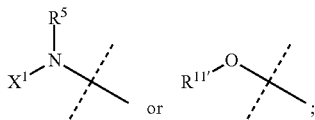

$R^5$ is H or $C_1$-$C_{12}$ alkyl;

$X^1$ is selected from $R^{11'}$ and $-OR^{11'}$; when $X^1$ is $R^{11'}$, $X^1$ is optionally taken together with $R^5$ and the nitrogen atom to which they are bound to form a 4-7 membered saturated or unsaturated ring having 0-2 additional heteroatoms selected from O, S and N, wherein said ring is optionally substituted with one or more groups selected from halo, CN, $CF_3$, $-OCF_3$, $-NO_2$, oxo, $-(CR^{19}R^{20})_nC(=Y')R^{16}$, $-(CR^{19}R^{20})_nC(=Y')OR^{16}$, $-(CR^{19}R^{20})_nC(=Y')NR^{16}R^{17}$, $-(CR^{19}R^{20})_nNR^{16}R^{17}$, $-(CR^{19}R^{20})_nOR^{16}$, $-(CR^{19}R^{20})_n-SR^{16}$, $-(CR^{19}R^{20})_nNR^{16}C(=Y)R^{17}$, $-(CR^{19}R^{20})_nNR^{16}C(=Y')OR^{17}$, $-(CR^{19}R^{20})_nNR^{18}C(=Y')NR^{16}R^{17}$, $-(CR^{19}R^{20})_nNR^{17}SO_2R^{16}$, $-(CR^{19}R^{20})_nOC(=Y')R^{16}$, $-(CR^{19}R^{20})_nOC(=Y')OR^{16}$, $-(CR^{19}R^{20})_nOC(=Y')NR^{16}R^{17}$, $-(CR^{19}R^{20})_nOS(O)_2(OR^{16})$, $-(CR^{19}R^{20})_nOP(=Y')(OR^{16})(OR^{17})$, $-(CR^{19}R^{20})_nOP(OR^{16})(OR^{17})$, $-(CR^{19}R^{20})_nS(O)R^{16}$, $-(CR^{19}R^{20})_nS(O)_2R^{16}$, $-(CR^{19}R^{20})_nS(O)_2NR^{16}R^{17}$, $-(CR^{19}R^{20})_nS(O)(OR^{16})$, $-(CR^{19}R^{20})_nS(O)_2(OR^{16})$, $-(CR^{19}R^{20})_nSC(=Y')R^{16}$, $-(CR^{19}R^{20})_n SC(=Y')OR^{16}$, $-(CR^{19}R^{20})_nSC(=Y)NR^{16}R^{17}$, and $R^{21}$;

each $R^{11'}$ is independently H, $C_1$-$C_{12}$ alkyl, $C_2$-$C_8$ alkenyl, $C_2$-$C_8$ alkynyl, carbocyclyl, aryl, or heteroaryl;

$R^{11}$, $R^{12}$ and $R^{13}$ are independently H, $C_1$-$C_{12}$ alkyl, $C_2$-$C_8$ alkenyl, $C_2$-$C_8$ alkynyl, carbocyclyl, heterocyclyl, aryl, or heteroaryl, or $R^{11}$ and $R^{12}$ together with the nitrogen to which they are attached form a 3-8 membered saturated, unsaturated or aromatic ring having 0-2 heteroatoms selected from O, S and N, wherein said ring is optionally substituted with one or more groups selected from halo, CN, $CF_3$, $-OCF_3$, $-NO_2$, $C_1$-$C_6$ alkyl, $-OH$, $-SH$, $-O(C_1$-$C_6$ alkyl), $-S(C_1$-$C_6$ alkyl), $-NH_2$, $-NH(C_1$-$C_6$ alkyl), $-N(C_1$-$C_6$ alkyl)$_2$, $-SO_2(C_1$-$C_6$ alkyl), $-CO_2H$, $-CO_2(C_1$-$C_6$ alkyl), $-C(O)NH_2$, $-C(O)NH(C_1$-$C_6$ alkyl), $-C(O)N(C_1$-$C_6$ alkyl)$_2$, $-N(C_1$-$C_6$ alkyl)$C(O)(C_1$-$C_6$ alkyl), $-NHC(O)(C_1$-$C_6$ alkyl), $-NHSO_2(C_1$-$C_6$ alkyl), $-N(C_1$-$C_6$ alkyl)$SO_2(C_1$-$C_6$ alkyl), $-SO_2NH_2$, $-SO_2NH(C_1$-$C_6$ alkyl), $-SO_2N(C_1$-$C_6$ alkyl)$_2$, $-OC(O)NH_2$, $-OC(O)NH(C_1$-$C_6$ alkyl), $-OC(O)N(C_1$-$C_6$ alkyl)$_2$, $-NHC(O)NH(C_1$-$C_6$ alkyl), $-NHC(O)N(C_1$-$C_6$ alkyl)$_2$, $-N(C_1$-$C_6$ alkyl)$C(O)NH(C_1$-$C_6$ alkyl), $-N(C_1$-$C_6$ alkyl)$C(O)N(C_1$-$C_6$ alkyl)$_2$, $-NHC(O)NH(C_1$-$C_6$ alkyl), $-NHC(O)N(C_1$-$C_6$ alkyl)$_2$, $-NHC(O)O(C_1$-$C_6$ alkyl), and $-N(C_1$-$C_6$ alkyl)$C(O)O(C_1$-$C_6$ alkyl);

$R^{14}$ and $R^{15}$ are independently selected from H, $C_1$-$C_{12}$ alkyl, aryl, carbocyclyl, heterocyclyl, and heteroaryl;

W' is

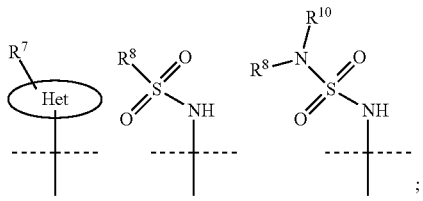

wherein

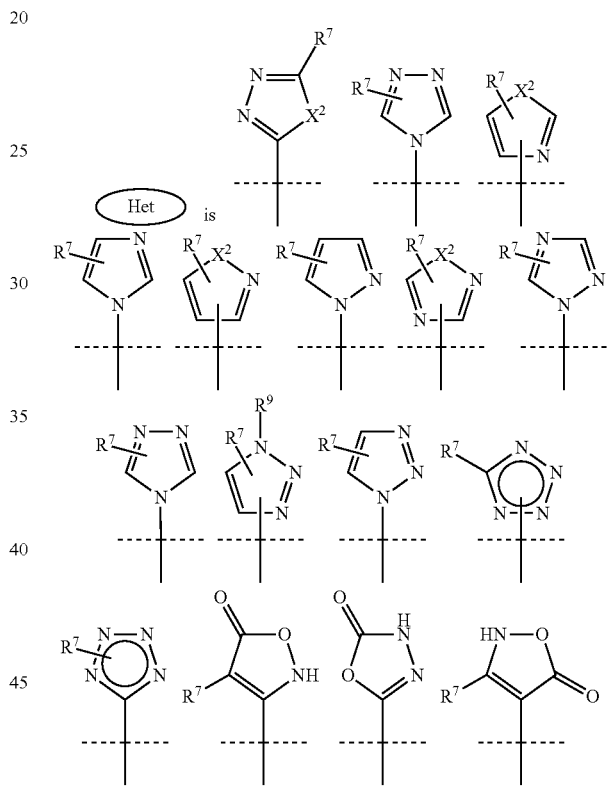

each $X^2$ is independently O, S, or $NR^9$;

each $R^7$ is independently selected from H, halo, CN, $CF_3$, $-OCF_3$, $-NO_2$, $-(CR^{14}R^{15})_nC(=Y')R^{11}$, $-(CR^{14}R^{15})_nC(=Y')OR^{11}$, $-(CR^{14}R^{15})_nC(=Y')NR^{11}R^{12}$, $-(CR^{14}R^{15})_nNR^{11}R^{12}$, $-(CR^{14}R^{15})_nOR^{11}$, $-(CR^{14}R^{15})_nSR^{11}$, $-(CR^{14}R^{15})_nNR^{12}C(=Y')R^{11}$, $-(CR^{14}R^{15})_nNR^{12}C(=Y')OR^{11}$, $-(CR^{14}R^{15})_nNR^{13}C(=Y')NR^{11}R^{12}$, $-(CR^{14}R^{15})_nNR^{12}SO_2R^{11}$, $-(CR^{14}R^{15})_nOC(=Y')R^{11}$, $-(CR^{14}R^{15})_nOC(=Y')OR^{11}$, $-(CR^{14}R^{15})_nOC(=Y')NR^{11}R^{12}$, $-(CR^{14}R^{15})_nOS(O)_2(OR^{11})$, $-(CR^{14}R^{15})_nOP(=Y')(OR^{11})(OR^{12})$, $-(CR^{14}R^{15})_nOP(OR^{11})(OR^{12})$, $-(CR^{14}R^{15})_nS(O)R^{11}$, $-(CR^{14}R^{15})_nS(O)_2R^{11}$, $-(CR^{14}R^{15})_nS(O)_2NR^{11}R^{12}$, $-(CR^{14}R^{15})_nS(O)(OR^{11})$, $-(CR^{14}R^{15})_nS(O)_2(OR^{11})$, $-(CR^{14}R^{15})_nSC(=Y')R^{11}$, $-(CR^{14}R^{15})_nSC(=Y')OR^{11}$, $-(CR^{14}R^{15})_nSC(=Y')NR^{11}R^{12}$, $C_1$-$C_{12}$ alkyl, $C_2$-$C_8$ alkenyl, $C_2$-$C_8$ alkynyl, carbocyclyl, heterocyclyl, aryl, and heteroaryl;

each $R^8$ is independently selected from $C_1$-$C_{12}$ alkyl, aryl, carbocyclyl, heterocyclyl, and heteroaryl;

$R^9$ is selected from H, $-(CR^{14}R^{15})_nC(=Y')R^{11}$, $-(CR^{14}R^{15})_nC(=Y')OR^{11}$, $-(CR^{14}R^{15})_nC(=Y')NR^{11}R^{12}$, $-(CR^{14}R^{15})_qNR^{11}R^{12}$, $-(CR^{14}R^{15})_qOR^{11}$, $-(CR^{14}R^{15})_qSR^{11}$, $-(CR^{14}R^{15})_qNR^{12}C(=Y')R^{11}$, $-(CR^{14}R^{15})_qNR^{12}C(=Y')OR^{11}$, $-(CR^{14}R^{15})_qNR^{13}C(=Y')NR^{11}R^{12}$, $-(CR^{14}R^{15})_qNR^{12}SO_2R^{11}$, $-(CR^{14}R^{15})_qOC(=Y')R^{11}$, $-(CR^{14}R^{15})_qOC(=Y')OR^{11}$, $-(CR^{14}R^{15})_qOC(=Y')NR^{11}R^{12}$, $-(CR^{14}R^{15})_qOS(O)_2(OR^{11})$, $-(CR^{14}R^{15})_qOP(=Y')(OR^{11})(OR^{12})$, $-(CR^{14}R^{15})_qOP(OR^{11})(OR^{12})$, $-(CR^{14}R^{15})S(O)R^{11}$, $-(CR^{14}R^{15})_nS(O)_2R^{11}$, $-(CR^{14}R^{15})_nS(O)_2NR^{11}R^{12}$, $C_{1-2}$ alkyl, $C_2$-$C_8$ alkenyl, $C_2$-$C_8$ alkynyl, carbocyclyl, heterocyclyl, aryl, and heteroaryl;

$R^{10}$ is H, $C_1$-$C_6$ alkyl or $C_3$-$C_4$ carbocyclyl;

$X^4$ is

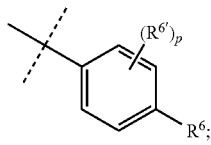

$R^6$ is H, halo, $C_1$-$C_6$ alkyl, $C_2$-$C_8$ alkenyl, $C_2$-$C_8$ alkynyl, carbocyclyl, heteroaryl, heterocyclyl, $-OCF_3$, $-NO_2$, $-Si(C_1$-$C_6$ alkyl), $-(CR^{19}R^{20})_nNR^{16}R^{17}$, $-(CR^{19}R^{20})_nOR^{16}$, or $-(CR^{19}R^{20})_n-SR^{16}$;

$R^{6'}$ is H, halo, $C_1$-$C_6$ alkyl, carbocyclyl, $CF_3$, $-OCF_3$, $-NO_2$, $-Si(C_1$-$C_6$ alkyl), $-(CR^{19}R^{20})_nNR^{16}R^{17}$, $-(CR^{19}R^{20})_nOR^{16}$, $-(CR^{19}R^{20})_n-SR^{16}$, $C_2$-$C_8$ alkenyl, $C_2$-$C_8$ alkynyl, heterocyclyl, aryl, or heteroaryl;

p is 0, 1, 2 or 3;

n is 0, 1, 2 or 3;

q is 2 or 3;

wherein each said alkyl, alkenyl, alkynyl, carbocyclyl, heterocyclyl, aryl and heteroaryl of $R^1$, $R^2$, $R^3$, $R^4$, $R^5$, $R^6$, $R^{6'}$, $R^7$, $R^8$, $R^9$, $R^{10}$, $R^{11}$, $R^{12}$, $R^{13}$, $R^{14}$, $R^{15}$ and $R^A$ is independently optionally substituted with one or more groups independently selected from halo, CN, $CF_3$, $-OCF_3$, $-NO_2$, oxo, $-Si(C_1$-$C_6$ alkyl), $-(CR^{19}R^{20})_nC(=Y')R^{16}$, $-(CR^{19}R^{20})_nC(=Y')OR^{16}$, $-(CR^{19}R^{20})_nC(=Y')NR^{16}R^{17}$, $-(CR^{19}R^{20})_nNR^{16}R^{17}$, $-(CR^{19}R^{20})_nOR^{16}$, $-(CR^{19}R^{20})_nSR^{16}$, $-(CR^{19}R^{20})_nNR^{16}C(=Y')R^{17}$, $-(CR^{19}R^{20})_nNR^{16}C(=Y')OR^{17}$, $-(CR^{19}R^{20})_nNR^{18}C(=Y')NR^{16}R^{17}$, $-(CR^{19}R^{20})_nNR^{17}SO_2R^{16}$, $-(CR^{19}R^{20})_nOC(=Y')R^{16}$, $-(CR^{19}R^{20})_nOC(=Y')OR^{16}$, $-(CR^{19}R^{20})_nOC(=Y')NR^{16}R^{17}$, $-(CR^{19}R^{20})_nOS(O)_2(OR^{16})$, $-(CR^{19}R^{20})_nOP(=Y')(OR^{16})(OR^{17})$, $-(CR^{19}R^{20})_nOP(OR^{16})(OR^{17})$, $-(CR^{19}R^{20})_nS(O)R^{16}$, $-(CR^{19}R^{20})_nS(O)_2R^{16}$, $-(CR^{19}R^{20})_nS(O)_2NR^{16}R^{17}$, $-(CR^{19}R^{20})_nS(O)(OR^{16})$, $-(CR^{19}R^{20})_nS(O)_2(OR^{16})$, $-(CR^{19}R^{20})_nSC(=Y')R^{16}$, $-(CR^{19}R^{20})_nSC(=Y')OR^{16}$, $-(CR^{19}R^{20})_nSC(=Y')NR^{16}R^{17}$, and $R^{21}$;

each $R^{16}$, $R^{17}$ and $R^{18}$ is independently H, $C_1$-$C_{12}$ alkyl, $C_2$-$C_8$ alkenyl, $C_2$-$C_8$ alkynyl, carbocyclyl, heterocyclyl, aryl, or heteroaryl, wherein said alkyl, alkenyl, alkynyl, carbocyclyl, heterocyclyl, aryl, or heteroaryl is optionally substituted with one or more groups selected from halo, CN, $-OCF_3$, $CF_3$, $-NO_2$, $C_1$-$C_6$ alkyl, $-OH$, $-SH$, $-O(C_1$-$C_6$ alkyl), $-S(C_1$-$C_6$ alkyl), $-NH_2$, $-NH(C_1$-$C_6$ alkyl), $-N(C_1$-$C_6$ alkyl)$_2$, $-SO_2(C_1$-$C_6$ alkyl), $-CO_2H$, $-CO_2(C_1$-$C_6$ alkyl), $-C(O)NH_2$, $-C(O)NH(C_1$-$C_6$ alkyl), $-C(O)N(C_1$-$C_6$ alkyl)$_2$, $-N(C_1$-$C_6$ alkyl)C(O)(C_1$-$C_6$ alkyl), $-NHC(O)(C_1$-$C_6$ alkyl), $-NHSO_2(C_1$-$C_6$ alkyl), $-N(C_1$-$C_6$ alkyl)SO_2(C_1$-$C_6$ alkyl), $-SO_2NH_2$, $-SO_2NH(C_1$-$C_6$ alkyl), $-SO_2N(C_1$-$C_6$ alkyl)$_2$, $-OC(O)NH_2$, $-OC(O)NH(C_1$-$C_6$ alkyl), $-OC(O)N(C_1$-$C_6$ alkyl)$_2$, $-OC(O)O(C_1$-$C_6$ alkyl), $-NHC(O)NH(C_1$-$C_6$ alkyl), $-NHC(O)N(C_1$-$C_6$ alkyl)$_2$, $-N(C_1$-$C_6$ alkyl)C(O)NH(C_1$-$C_6$ alkyl), $-N(C_1$-$C_6$ alkyl)C(O)N(C_1$-$C_6$ alkyl)$_2$, $-NHC(O)NH(C_1$-$C_6$ alkyl), $-NHC(O)N(C_1$-$C_6$ alkyl)$_2$, $-NHC(O)O(C_1$-$C_6$ alkyl), and $-N(C_1$-$C_6$ alkyl)C(O)O(C_1$-$C_6$ alkyl);

or $R^{16}$ and $R^{17}$ together with the nitrogen to which they are attached form a 3-8 membered saturated, unsaturated or aromatic ring having 0-2 heteroatoms selected from O, S and N, wherein said ring is optionally substituted with one or more groups selected from halo, CN, $-OCF_3$, $CF_3$, $-NO_2$, $C_1$-$C_6$ alkyl, $-OH$, $-SH$, $-O(C_1$-$C_6$ alkyl), $-S(C_1$-$C_6$ alkyl), $-NH_2$, $-NH(C_1$-$C_6$ alkyl), $-N(C_1$-$C_6$ alkyl)$_2$, $-SO_2(C_1$-$C_6$ alkyl), $-CO_2H$, $-CO_2(C_1$-$C_6$ alkyl), $-C(O)NH_2$, $-C(O)NH(C_1$-$C_6$ alkyl), $-C(O)N(C_1$-$C_6$ alkyl)$_2$, $-N(C_1$-$C_6$ alkyl)C(O)(C_1$-$C_6$ alkyl), $-NHC(O)(C_1$-$C_6$ alkyl), $-NHSO_2(C_1$-$C_6$ alkyl), $-N(C_1$-$C_6$ alkyl)SO_2(C_1$-$C_6$ alkyl), $-SO_2NH_2$, $-SO_2NH(C_1$-$C_6$ alkyl), $-SO_2N(C_1$-$C_6$ alkyl)$_2$, $-OC(O)NH_2$, $-OC(O)NH(C_1$-$C_6$ alkyl), $-OC(O)N(C_1$-$C_6$ alkyl)$_2$, $-OC(O)O(C_1$-$C_6$ alkyl), $-NHC(O)NH(C_1$-$C_6$ alkyl), $-NHC(O)N(C_1$-$C_6$ alkyl)$_2$, $-N(C_1$-$C_6$ alkyl)C(O)NH(C_1$-$C_6$ alkyl), $-N(C_1$-$C_6$ alkyl)C(O)N(C_1$-$C_6$ alkyl)$_2$, $-NHC(O)NH(C_1$-$C_6$ alkyl), $-NHC(O)N(C_1$-$C_6$ alkyl)$_2$, $-NHC(O)O(C_1$-$C_6$ alkyl), and $-N(C_1$-$C_6$ alkyl)C(O)O(C_1$-$C_6$ alkyl);

$R^{19}$ and $R^{20}$ are independently selected from H, $C_1$-$C_{12}$ alkyl, $-(CH_2)_n$-aryl, $-(CH_2)_n$-carbocyclyl, $-(CH_2)_n$-heterocyclyl, and $-(CH_2)_n$-heteroaryl;

$R^{21}$ is $C_1$-$C_{12}$ alkyl, $C_2$-$C_8$ alkenyl, $C_2$-$C_8$ alkynyl, carbocyclyl, heterocyclyl, aryl, or heteroaryl, wherein each member of $R^{21}$ is optionally substituted with one or more groups selected from halo, oxo, CN, $-OCF_3$, $CF_3$, $-NO_2$, $C_1$-$C_6$ alkyl, $-OH$, $-SH$, $-O(C_1$-$C_6$ alkyl), $-S(C_1$-$C_6$ alkyl), $-NH_2$, $-NH(C_1$-$C_6$ alkyl), $-N(C_1$-$C_6$ alkyl)$_2$, $-SO_2(C_1$-$C_6$ alkyl), $-CO_2H$, $-CO_2(C_1$-$C_6$ alkyl), $-C(O)NH_2$, $-C(O)NH(C_1$-$C_6$ alkyl), $-C(O)N(C_1$-$C_6$ alkyl)$_2$, $-N(C_1$-$C_6$ alkyl)C(O)(C_1$-$C_6$ alkyl), $-NHC(O)(C_1$-$C_6$ alkyl), $-NHSO_2(C_1$-$C_6$ alkyl), $-N(C_1$-$C_6$ alkyl)SO_2(C_1$-$C_6$ alkyl), $-SO_2NH_2$, $-SO_2NH(C_1$-$C_6$ alkyl), $-SO_2N(C_1$-$C_6$ alkyl)$_2$, $-OC(O)NH_2$, $-OC(O)NH(C_1$-$C_6$ alkyl), $-OC(O)N(C_1$-$C_6$ alkyl)$_2$, $-OC(O)O(C_1$-$C_6$ alkyl), $-NHC(O)NH(C_1$-$C_6$ alkyl), $-NHC(O)N(C_1$-$C_6$ alkyl)$_2$, $-N(C_1$-$C_6$ alkyl)C(O)NH(C_1$-$C_6$ alkyl), $-N(C_1$-$C_6$ alkyl)C(O)N(C_1$-$C_6$ alkyl)$_2$, $-NHC(O)NH(C_1$-$C_6$ alkyl), $-NHC(O)N(C_1$-$C_6$ alkyl)$_2$, $-NHC(O)O(C_1$-$C_6$ alkyl), and $-N(C_1$-$C_6$ alkyl)C(O)O(C_1$-$C_6$ alkyl);

each Y' is independently O, $NR^{22}$, or S; and $R^{22}$ is H or $C_1$-$C_{12}$ alkyl.

The present invention includes a composition (e.g., a pharmaceutical composition) comprising a compound of formula I (and/or solvates, hydrates and/or salts thereof) and a carrier (a pharmaceutically acceptable carrier). The present invention also includes a composition (e.g., a pharmaceutical composition) comprising a compound of formula I (and/or solvates, hydrates and/or salts thereof) and a carrier (a pharmaceutically acceptable carrier), further comprising a second chemotherapeutic and/or a second anti-inflammatory agent. The present compositions are useful for inhibiting abnormal cell growth or treating a hyperproliferative disorder in a mammal (e.g., human). The present compositions are also useful for treating inflammatory diseases in a mammal (e.g., human).

The present invention includes a method of inhibiting abnormal cell growth or treating a hyperproliferative disorder in a mammal (e.g., human) comprising administering to said mammal a therapeutically effective amount of a compound of formula I (and/or solvates and salts thereof) or a composition thereof, alone or in combination with a second chemotherapeutic agent.

The present invention includes a method of treating an inflammatory disease in a mammal (e.g., human) comprising administering to said mammal a therapeutically effective amount of a compound of formula I (and/or solvates and salts thereof) or a composition thereof, alone or in combination with a second anti-inflammatory agent.

The present invention includes a method of using the present compounds for in vitro, in situ, and in vivo diagnosis or treatment of mammalian cells, organisms, or associated pathological conditions.

DETAILED DESCRIPTION OF EXEMPLARY EMBODIMENTS

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

Definitions

The term "alkyl" as used herein refers to a saturated linear or branched-chain monovalent hydrocarbon radical of one to twelve carbon atoms. Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (1-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkenyl" refers to linear or branched-chain monovalent hydrocarbon radical of two to twelve carbon atoms with at least one site of unsaturation, i.e., a carbon-carbon, $sp^2$ double bond, wherein the alkenyl radical includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like.

The term "alkynyl" refers to a linear or branched monovalent hydrocarbon radical of two to twelve carbon atoms with at least one site of unsaturation, i.e., a carbon-carbon, sp triple bond. Examples include, but are not limited to, ethynyl (—C≡CH), propynyl (propargyl, —$CH_2$C≡CH), and the like.

The terms "carbocycle", "carbocyclyl", "carbocyclic ring" and "cycloalkyl" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-18 carbon atoms derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, indenyl, indanyl, 1,2-dihydronaphthalene, 1,2,3,4-tetrahydronaphthyl, and the like.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to 18 ring atoms in which at least one ring atom is a heteroatom selected from nitrogen, oxygen and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W.A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidinyl, morpholinyl, thiomorpholinyl, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, and azabicyclo[2.2.2]hexanyl. Spiro moieties are also included within the scope of this definition. Examples of a heterocyclic group wherein ring atoms are substituted with oxo (=O) moieties are pyrimidinonyl and 1,1-dioxo-thiomorpholinyl.

The term "heteroaryl" refers to a monovalent aromatic radical of 5- or 6-membered rings, and includes fused ring systems (at least one of which is aromatic) of 5-18 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The heterocycle or heteroaryl groups may be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "halo" refers to F, Cl, Br or I. The heteroatoms present in heteroaryl or heterocyicyl include the oxidized forms such as N$^+$→O$^-$, S(O) and S(O)$_2$.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "abnormal cell growth" and "hyperproliferative disorder" are used interchangeably in this application. "Abnormal cell growth", as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, acute leukemia, as well as head/brain and neck cancer.

A "chemotherapeutic agent" is a compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKF.RB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE™ (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above. Other anti-angiogenic agents include MMP-2 (matrix-metalloproteinase 2) inhibitors, MMP-9 (matrix-metalloproteinase 9) inhibitors, COX-II (cyclooxygenase II) inhibitors, and VEGF receptor tyrosine kinase inhibitors. Examples of such useful matrix metalloproteinase inhibitors that can be used in combination with the present compounds/compositions (such as any one of the title compounds of EXAMPLES 5-25) are described in WO 96/33172, WO 96/27583, EP 818442, EP 1004578, WO 98/07697, WO 98/03516, WO 98/34918, WO 98/34915, WO 98/33768, WO 98/30566, EP 606,046, EP 931,788, WO 90/05719, WO 99/52910, WO 99/52889, WO 99/29667, WO 99/07675, EP 945864, U.S. Pat. No. 5,863,949, U.S. Pat. No. 5,861,510, and EP 780,386, all of which are incorporated herein in their entireties by reference. Examples of VEGF receptor tyrosine kinase inhibitors include 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)-quinazoline (AZD2171; Example 240 within WO 00/47212), vatalanib (PTK787; WO 98/35985) and SU11248 (sunitinib; WO 01/60814), and compounds such as those disclosed in PCT Publication Nos. WO 97/22596, WO 97/30035, WO 97/32856, and WO 98/13354).

Other examples of chemotherapeutic agents that can be used in combination with the present compounds (such as any one of the title compounds of EXAMPLES 5-25) include inhibitors of PI3K (phosphoinositide-3 kinase), such as those reported in Yaguchi et al (2006) Jour. of the Nat. Cancer Inst. 98(8):545-556; U.S. Pat. No. 7,173,029; U.S. Pat. No. 7,037,915; U.S. Pat. No. 6,608,056; U.S. Pat. No. 6,608,053; U.S. Pat. No. 6,838,457; U.S. Pat. No. 6,770,641; U.S. Pat. No. 6,653,320; U.S. Pat. No. 6,403,588; US 2008/0242665; WO 2006/046031; WO 2006/046035; WO 2006/046040; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070; U.S. Pat. No. 6,703,414; and WO 97/15658, all of which are incorporated herein in their entireties by reference. Specific examples of such PI3K inhibitors include SF-1126 (PI3K inhibitor, Semafore Pharmaceuticals), BEZ-235 (PI3K inhibitor, Novartis), XL-147 (PI3K inhibitor, Exelixis, Inc.), and GDC-0941 (PI3K inhibitor, Genentech, Inc.).

The term "inflammatory diseases" as used in this application includes, but not limited to, rheumatoid arthritis, atherosclerosis, congestive hear failure, inflammatory bowel disease (including, but not limited to, Crohn's disease and ulcerative colitis), chronic obstructive pulmonary disease in the lung, fibrotic disease in the liver and kidney, Crohn's disease, lupus, skin diseases such as psoriasis, eczema and scleroderma, osteoarthritis, multiple sclerosis, asthma, diseases and disorders related to diabetic complications, fibrotic organ failure in organs such as lung, liver, kidney, and inflammatory complications of the cardiovascular system such as acute coronary syndrome.

An "anti-inflammatory agent" is a compound useful in the treatment of inflammation. Examples of anti-inflammatory agents include injectable protein therapeutics such as Enbrel®, Remicade®, Humira® and Kineret®. Other examples of anti-inflammatory agents include non-steroidal anti-inflammatory agents (NSAIDs), such as ibuprofen or aspirin (which reduce swelling and alleviate pain); disease-modifying anti-rheumatic drugs (DMARDs) such as methotrexate; 5-aminosalicylates (sulfasalazine and the sulfa-free agents); corticosteroids; immunomodulators such as 6-mercaptoputine ("6-MP"), azathioprine ("AZA"), cyclosporines, and biological response modifiers such as Remicade® (infliximab) and Enbrel® (etanercept); fibroblast growth factors; platelet derived growth factors; enzyme blockers such as Arava® (leflunomide); and/or a cartilage protecting agent such as hyaluronic acid, glucosamine, and chondroitin.

The term "prodrug" as used in this application refers to a precursor or derivative form of a compound of the invention that is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, ester-containing prodrugs, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

A "metabolite" is a product produced through metabolism in the body of a specified compound or salt thereof. Metabolites of a compound may be identified using routine techniques known in the art and their activities determined using tests such as those described herein. Such products may result for example from the oxidation, hydroxylation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

A "liposome" is a small vesicle composed of various types of lipids, phospholipids and/or surfactant which is useful for delivery of a drug (such as the MEK inhibitors disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomer" refers to compounds which have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as crystallization, electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and trialkylsilyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "compound of this invention", "compounds of the present invention" "compounds of formula I", "imidazopyridines" and "imidazopyridines of formula I", unless otherwise indicated, include compounds/imidazopyridines of formula I and stereoisomers, geometric isomers, tautomers, solvates, metabolites, salts (e.g., pharmaceutically acceptable salts) and prodrugs thereof.

The present invention provides imidazopyridines of formula I as described above useful as kinase inhibitors, particularly useful as MEK kinase inhibitors. In an embodiment of the present invention, when $R^3$ is $(CR^{14}R^{15})_nC(=O)R^{11}$, $—(CR^{14}R^{15})_nNR^{11}R^{12}$, $(CR^{14}R^{15})_nOR^{11}$, $—(CR^{14}R^{15})_nSR^{11}$, $(CR^{14}R^{15})_nS(O)R^{11}$, or $—(CR^{14}R^{15})S(O)_2R^{11}$; n is 0; and $Z^1$ is N, then said $R^{11}$ or $R^{12}$ is not aryl; when $Z^1$ is N, then $R^3$ is not $CH_2$-aryl; and all other variables are as defined in formula I.

In an embodiment of the present invention, compounds are of formula I-a or I-b and all other variables are as defined in formula I, or as defined in the embodiment described above.

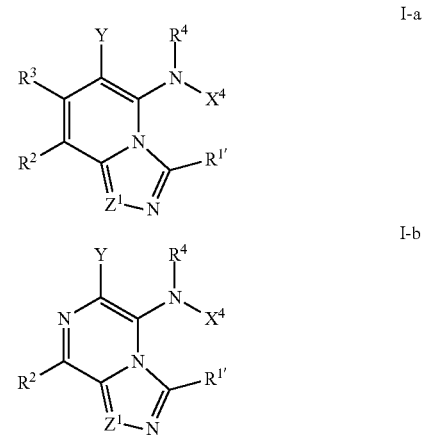

In an embodiment of the present invention, $R^2$ is H, halo, $CF_3$, or $C_1$-$C_3$ alkyl; and all other variables are as defined in formula I, I-a or I-b, or as defined in any one of the embodiments described above.

In another embodiment of the present invention, $R^2$ is H, methyl, $CF_3$, F, or Cl; and all other variables are as defined in formula I, I-a or I-b, or as defined in any one of the embodiments described above.

In another embodiment of the present invention, $R^2$ is H, F or Cl; and all other variables are as defined in formula I, I-a or I-b, or as defined in any one of the embodiments described above.

In an embodiment of the present invention, $R^3$ is H, halo, $CF_3$, or $C_1$-$C_3$ alkyl; and all other variables are as defined in formula I or I-a, or as defined in any one of the embodiments described above.

In another embodiment of the present invention, $R^3$ is H, methyl, $CF_3$, F, or Cl; and all other variables are as defined in formula I or I-a, or as defined in any one of the embodiments described above.

In another embodiment of the present invention, $R^3$ is H, F or Cl; and all other variables are as defined in formula I or I-a, or as defined in any one of the embodiments described above.

In an embodiment of the present invention, $R^P$ is H or $C_1$-$C_3$ alkyl; and all other variables are as defined in formula I, I-a or I-b, or as defined in any one of the embodiments described above. In another embodiment, $R^{1'}$ is H, and all other variables are as defined in formula I, I-a or I-b, or as defined in any one of the embodiments described above.

In an embodiment of the present invention, $Z^1$ is $CR^1$ and all other variables are as defined in formula I, I-a or I-b, or as defined in any one of the embodiments described above.

In an embodiment of the present invention, $Z^1$ is N and all other variables are as defined in formula I or I-a, or as defined in any one of the embodiments described above.

In another embodiment of the present invention, $Z^1$ is $CR^1$ and $R^1$ is H or $C_1$-$C_3$ alkyl; and all other variables are as defined in formula I, I-a or I-b, or as defined in any one of the embodiments described above. In another embodiment, $R^1$ is H, and all other variables are as defined in formula I, I-a or I-b, or as defined in any one of the embodiments above. In another embodiment, $R^1$ is methyl, and all other variables are as defined in formula I, I-a or I-b, or as defined in any one of the embodiments above.

In an embodiment of the present invention, $R^4$ is H or $C_1$-$C_6$ alkyl; and all other variables are as defined in formula I, I-a or I-b, or as defined in any one of the embodiments above.

In an embodiment of the present invention, $R^4$ is H or methyl; and all other variables are as defined in formula I, I-a or I-b, or as defined in any one of the embodiments above. In another embodiment of the present invention, $R^4$ is H; and all other variables are as defined in formula I, I-a or I-b, or as defined in any one of the embodiments above.

In an embodiment of the present invention, $R^5$ is H or $C_1$-$C_6$ alkyl; and all other variables are as defined in formula I, I-a or I-b, or as defined in any one of the embodiments above.

In another embodiment of the present invention, $R^5$ is H or methyl; and all other variables are as defined in formula I, I-a or I-b, or as defined in any one of the embodiments above.

In another embodiment of the present invention, $R^5$ is H; and all other variables are as defined in formula I, I-a or I-b, or as defined in any one of the embodiments above.

In another embodiment of the present invention, $R^5$ is methyl; and all other variables are as defined in formula I, I-a or I-b, or as defined in any one of the embodiments above.

In an embodiment of the present invention, $X^1$ is $OR^{11'}$; and all other variables are as defined in formula I, I-a or I-b; or as defined in any one of the embodiments above.

In another embodiment of the present invention, $X^1$ is $OR^{11'}$ wherein $R^{11'}$ is H or $C_1$-$C_{12}$ alkyl (e.g., $C_1$-$C_6$ alkyl) substituted with one or more groups independently selected from halo, CN, $CF_3$, $-OCF_3$, $-NO_2$, oxo, $-(CR^{19}R^{20})_nC(=Y')R^{16}$, $-(CR^{19}R^{20})_nC(=Y')OR^{16}$, $-(CR^{19}R^{20})_nC(=Y')NR^{16}R^{17}$, $-(CR^{19}R^{20})_nNR^{16}R^{17}$, $-(CR^{19}R^{20})_nOR^{16}$, $-(CR^{19}R^{20})_nSR^{16}$, $-(CR^{19}R^{20})_nNR^{16}C(=Y')R^{17}$, $-(CR^{19}R^{20})_nNR^{16}C(=Y')OR^{17}$, $-(CR^{19}R^{20})_nNR^{18}C(=Y')NR^{16}R^{17}$, $-(CR^{19}R^{20})_nNR^{17}SO_2R^{16}$, $-(CR^{19}R^{20})_nOC(=Y')R^{16}$, $-(CR^{19}R^{20})_nOC(=Y')OR^{16}$, $-(CR^{19}R^{20})_nOC(=Y')NR^{16}R^{17}$, $-(CR^{19}R^{20})_nOS(O)_2(OR^{16})$, $-(CR^{19}R^{20})_nOP(=Y')(OR^{16})(OR^{17})$, $-(CR^{19}R^{20})_nOP(OR^1)$, $-(CR^{19}R^{20})_nS(O)R^{16}$, $-(CR^{19}R^{20})_nS(O)_2R^{16}$, $-(CR^{19}R^{20})_nS(O)_2NR^{16}R^{17}$, $-(CR^{19}R^{20})_nS(O)(OR^{16})$, $-(CR^{19}R^{20})_nS(O)_2(OR^{16})$, $-(CR^{19}R^{20})_nSC(=Y')R^{16}$, $-(CR^{19}R^{20})_nSC(=Y')OR^{16}$, $-(CR^{19}R^{20})_nSC(=Y')NR^{16}R^{17}$, and $R^{21}$; and all other variables are as defined in formula I, I-a or I-b, or as defined in any one of the embodiments above.

In another embodiment of the present invention, $X^1$ is $OR^{11'}$ wherein $R^{11'}$ is heterocyclyl (e.g., 4- to 6-membered heterocyclyl) optionally substituted with one or more groups independently selected from halo, CN, $CF_3$, $-OCF_3$, $-NO_2$, oxo, $-(CR^{19}R^{20})_nC(=Y')R^{16}$, $-(CR^{19}R^{20})_nC(=Y')OR^{16}$, $-(CR^{19}R^{20})_nC(=Y')NR^{16}R^{17}$, $-(CR^{19}R^{20})_nNR^{16}R^{17}$, $-(CR^{19}R^{20})_nOR^{16}$, $-(CR^{19}R^{20})_nSR^{16}$, $-(CR^{19}R^{20})_nNR^{16}C(=Y')R^{17}$, $-(CR^{19}R^{20})_nNR^{16}C(=Y')OR^{17}$, $-(CR^{19}R^{20})_nNR^{18}C(=Y')NR^{16}R^{17}$, $-(CR^{19}R^{20})_nNR^{17}SO_2R^{16}$, $-(CR^{19}R^{20})_nOC(=Y')R^{16}$, $-(CR^{19}R^{20})_nOC(=Y')OR^{16}$, $-(CR^{19}R^{20})_nOC(=Y')NR^{16}R^{17}$, $-(CR^{19}R^{20})_nOS(O)_2(OR^{16})$, $-(CR^{19}R^{20})_nOP(=Y')(OR^{16})(OR^{17})$, $-(CR^{19}R^{20})_nOP(OR^{16})(OR^{17})$, $-(CR^{19}R^{20})_nS(O)R^{16}$, $-(CR^{19}R^{20})_nS(O)_2R^{16}$, $-(CR^{19}R^{20})_nS(O)_2NR^{16}R^{17}$, $-(CR^{19}R^{20})_nS(O)(OR^{16})$, $-(CR^{19}R^{20})_nS(O)_2(OR^{16})$, $-(CR^{19}R^{20})_nSC(=Y')R^{16}$, $-(CR^{19}R^{20})_nSC(=Y')OR^{16}$, $-(CR^{19}R^{20})_nSC(=Y')NR^{16}R^{17}$, and $R^{21}$; and all other variables are as defined in formula I, I-a or I-b, or as defined in any one of the embodiments above.

In another embodiment of the present invention, $X^1$ is $OR^{11'}$ wherein $R^{11'}$ is 4- to 6-membered heterocyclyl having 1 nitrogen ring atom wherein said heterocyclyl is optionally substituted with one or more groups independently selected from halo, CN, $CF_3$, $-OCF_3$, $-NO_2$, oxo, $-(CR^{19}R^{20})_nC(=Y')R^{16}$, $-(CR^{19}R^{20})_nC(=Y')OR^{16}$, $-(CR^{19}R^{20})_nC(=Y')NR^{16}R^{17}$, $-(CR^{19}R^{20})_nNR^{16}R^{17}$, $-(CR^{19}R^{20})_nOR^{16}$, $-(CR^{19}R^{20})_nSR^{16}$, $-(CR^{19}R^{20})_nNR^{16}C(=Y')R^{17}$, $-(CR^{19}R^{20})_nNR^{16}C(=Y')OR^{17}$, $-(CR^{19}R^{20})_nNR^{18}C(=Y')NR^{16}R^{17}$, $-(CR^{19}R^{20})_nNR^{17}SO_2R^{16}$, $-(CR^{19}R^{20})_nOC(=Y')R^{16}$, $-(CR^{19}R^{20})_nOC(=Y')OR^{16}$, $-(CR^{19}R^{20})_nOC(=Y)NR^{16}R^{17}$, $-(CR^{19}R^{20})_nOS(O)_2(OR^{16})$, $-(CR^{19}R^{20})_nOP(=Y')(OR^{16})(OR^{17})$, $-(CR^{19}R^{20})_nOP(OR^{16})(OR^{17})$, $-(CR^{19}R^{20})_nS(O)R^{16}$, $-(CR^{19}R^{20})_nS(O)_2R^{16}$, $-(CR^{19}R^{20})_nS(O)_2NR^{16}R^{17}$, $-(CR^{19}R^{20})_nS(O)(OR^{16})$, $-(CR^{19}R^{20})_nS(O)_2(OR^{16})$, $-(CR^{19}R^{20})_nSC(=Y')R^{16}$, $-(CR^{19}R^{20})_nSC(=Y')OR^{16}$, $-(CR^{19}R^{20})_nSC(=Y')NR^{16}R^{17}$, and $R^{21}$; and all other variables are as defined in formula I, I-a or I-b, or as defined in any one of the embodiments above.

In another embodiment of the present invention, X is:

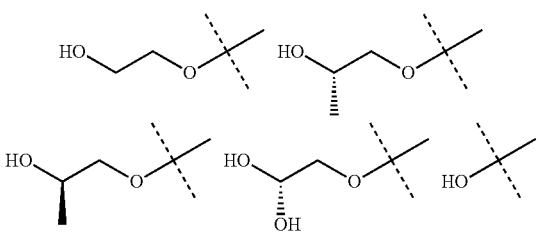

-continued

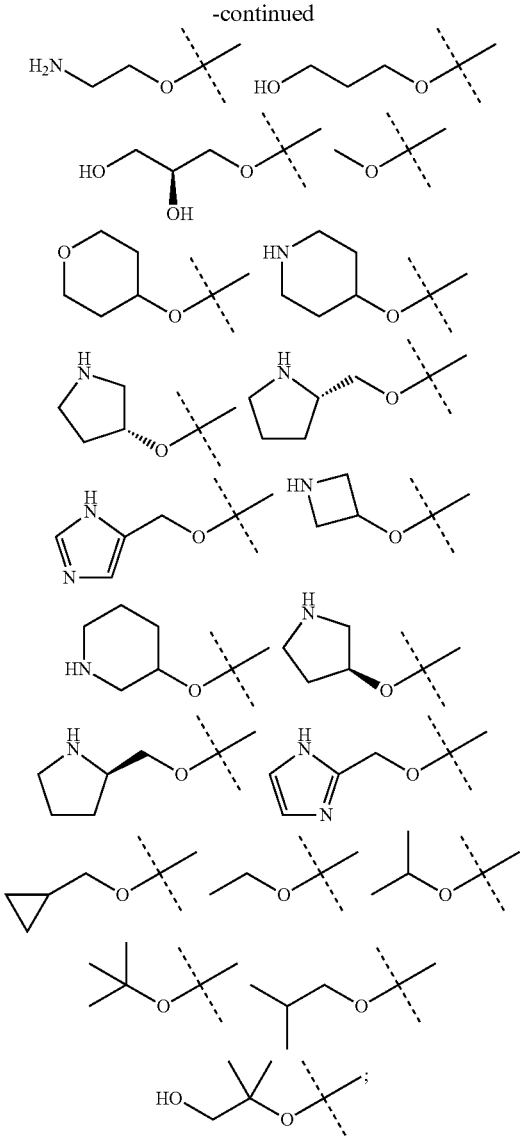

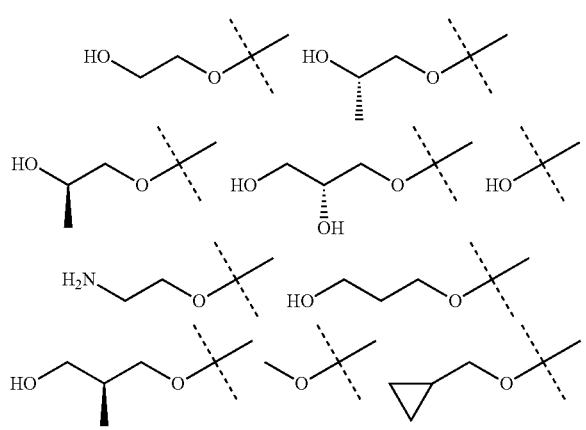

and all other variables are as defined in formula I, I-a or I-b, or as defined in any one of the embodiments above.

In another embodiment of the present invention, $X^1$ is

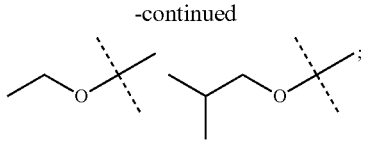

-continued and all other variables are as defined in formula I, I-a or I-b, or as defined in any one of the embodiments above.

In an embodiment of the present invention, $X^1$ is $R^{11'}$; and all other variables are as defined in formula I, I-a or I-b, or as defined in any one of the embodiments above.

In another embodiment of the present invention, $X^1$ is $R^{11'}$ wherein $R^{11'}$ is H or $C_1$-$C_{12}$ alkyl (e.g., $C_1$-$C_6$ alkyl) substituted with one or more groups independently selected from halo, CN, $CF_3$, —$OCF_3$, —$NO_2$, oxo, —Si($C_1$-$C_6$ alkyl), —$(CR^{19}R^{20})_nC(=Y')R^{16}$, —$(CR^{19}R^{20})_nC(=Y')OR^{16}$, —$(CR^{19}R^{20})_nC(=Y')NR^{16}R^{17}$, —$(CR^{19}R^{20})_nNR^{16}R^{17}$, —$(CR^{19}R^{20})_nOR^{16}$, —$(CR^{19}R^{20})_nSR^{16}$, —$(CR^{19}R^{20})_nNR^{16}C(=Y')R^{17}$—$(CR^{19}R^{20})_nNR^{16}C(=Y')OR^{17}$, —$(CR^{19}R^{20})_nNR^{18}C(=Y')NR^{16}R^{17}$, —$(CR^{19}R^{20})_nNR^{17}SO_2R^{16}$, —$(CR^{19}R^{20})_nOC(=Y')R^{16}$, —$(CR^{19}R^{20})_nOC(=Y')OR^{16}$, —$(CR^{19}R^{20})_nOC(=Y')NR^{16}R^{17}$, —$(CR^{19}R^{20})_nOS(O)_2(OR^{16})$, —$(CR^{19}R^{20})_nOP(=Y')(OR^{16})(OR^{17})$, —$(CR^{19}R^{20})_nOP(OR^{16})(OR^{17})$, —$(CR^{19}R^{20})_nS(O)R^{16}$, —$(CR^{19}R^{20})_nS(O)_2R^{16}$, —$(CR^{19}R^{20})_nS(O)_2NR^{16}R^{17}$, —$(CR^{19}R^{20})_nS(O)(OR^{16})$, —$(CR^{19}R^{20})_nS(O)_2(OR^{16})$, —$(CR^{19}R^{20})_nSC(=Y')R^{16}$, —$(CR^{19}R^{20})_nSC(=Y')OR^{16}$, —$(CR^{19}R^{20})_nSC(=Y')NR^{16}R^{17}$, and $R^{21}$; and all other variables are as defined in formula I, I-a or I-b, or as defined in any one of the embodiments above.

In another embodiment of the present invention, $X^1$ is

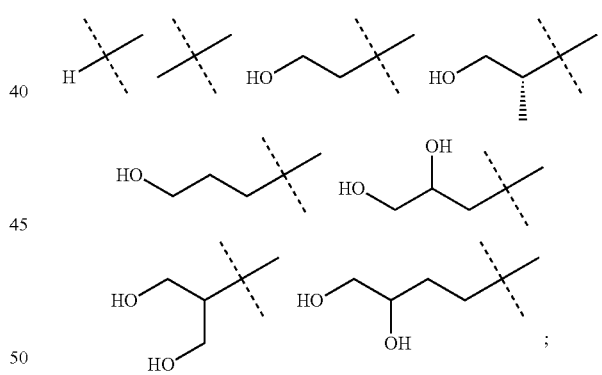

and all other variables are as defined in formula I, I-a or I-b, or as defined in any one of the embodiments above.

In another embodiment of the present invention, $R^5$ is H and $X^1$ is

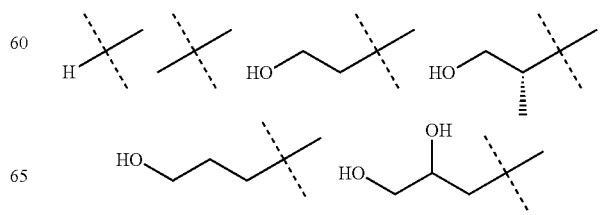

-continued

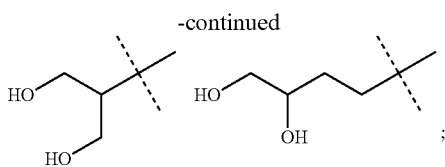

and all other variables are as defined in formula I, I-a or I-b, or as defined in any one of the embodiments above.

In another embodiment of the present invention, $X^1$ is

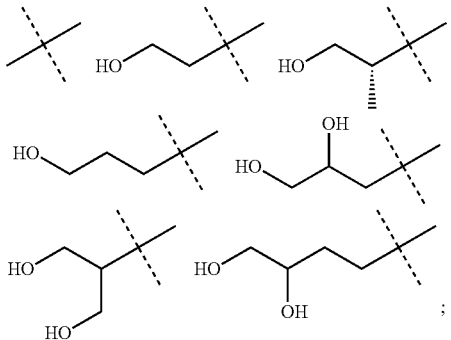

and all other variables are as defined in formula I, I-a or I-b, or as defined in any one of the embodiments above.

In another embodiment of the present invention, $R^5$ is methyl and $X^1$ is

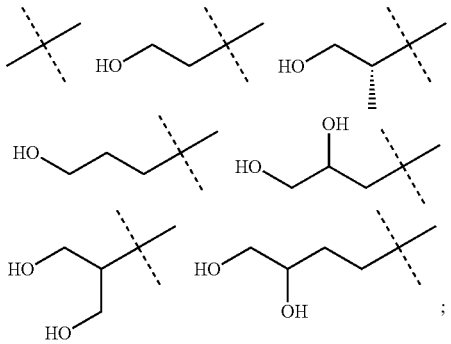

and all other variables are as defined in formula I, I-a or I-b, or as defined in any one of the embodiments above.

In an embodiment of the present invention, $X^1$ is $R^{11'}$ and $X^1$ is taken together with $R^5$ and the nitrogen atom to which they are bound to form a 4-5 membered saturated cyclic ring having 0-2 additional heteroatoms selected from O, S and N, wherein said cyclic ring is optionally substituted with one or more groups selected from halo, CN, $CF_3$, $-OCF_3$, $-NO_2$, oxo, $-(CR^{19}R^{20})_nC(=Y')R^{16}$, $-(CR^{19}R^{20})_nC(=Y')OR^{16}$, $-(CR^{19}R^{20})_nC(=Y')NR^{16}R^{17}$, $-(CR^{19}R^{20})_nNR^{16}R^{17}$, $-(CR^{19}R^{20})_nOR^{16}$, $-(CR^{19}R^{20})_nSR^{16}$, $-(CR^{19}R^{20})_nNR^{16}C(=Y')R^{17}$, $-(CR^{19}R^{20})_nNR^{16}C(=Y')OR^{17}$, $-(CR^{19}R^{20})_nNR^{18}C(=Y')NR^{16}R^{17}$, $-(CR^{19}R^{20})_nNR^{17}SO_2R^{16}$, $-(CR^{19}R^{20})_nOC(=Y')R^{16}$, $-(CR^{19}R^{20})_nOC(=Y')OR^{16}$, $-(CR^{19}R^{20})_nOC(=Y')NR^{16}R^{17}$, $-(CR^{19}R^{20})_nOS(O)_2(OR^{16})$, $-(CR^{19}R^{20})_nOP(=Y')(OR^{16})(OR^{17})$, $-(CR^{19}R^{20})_nOP(OR^{16})(OR^{17})$, $-(CR^{19}R^{20})_nS(O)R^{16}$, $-(CR^{19}R^{20})_nS(O)_2R^{16}$, $-(CR^{19}R^{20})_nS(O)_2NR^{16}R^{17}$, $-(CR^{19}R^{20})_nS(O)(OR^{16})$, $-(CR^{19}R^{20})_nS(O)_2(OR^{16})$, $-(CR^{19}R^{20})_nSC(=Y')R^{16}$, $-(CR^{19}R^{20})_nSC(=Y')OR^{16}$, $-(CR^{19}R^{20})_nSC(=Y')NR^{16}R^{17}$, and $R^{21}$; and all other variables are as defined in formula I, I-a or I-b, or as defined in any one of the embodiments above.

In another embodiment of the present invention, W is:

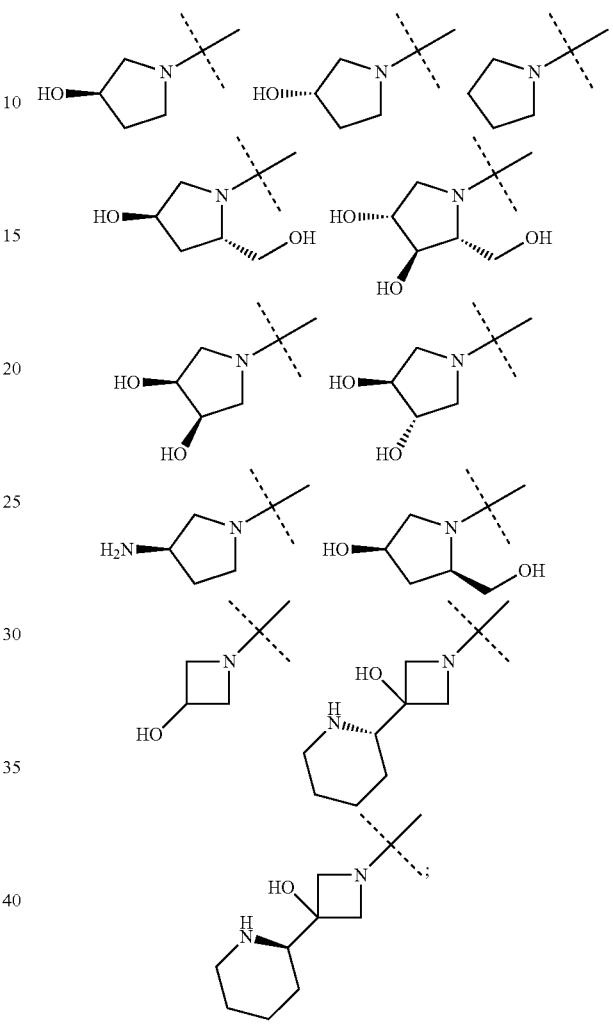

and all other variables are as defined in formula I, I-a or I-b, or as defined in any one of the embodiments above.

In an embodiment of the present invention, W is $-OR^{11'}$ wherein $R^{11'}$ is H or $C_1$-$C_{12}$ alkyl; and all other variables are as defined in formula I, I-a or I-b, or as defined in any one of the embodiments above.

In another embodiment of the present invention, W is $-OR^{11'}$ wherein $R^{11'}$ is H; and all other variables are as defined in formula I, I-a or I-b, or as defined in any one of the embodiments above.

In another embodiment of the present invention, W is $-OR^{11'}$ wherein $R^{11'}$ is $C_1$-$C_6$ alkyl; and all other variables are as defined in formula I, I-a or I-b, or as defined in any one of the embodiments above.

In an embodiment of the present invention, W' is $NHSO_2R^8$; and all other variables are as defined in formula I, I-a or I-b, or as defined in any one of the embodiments above.

In an embodiment of the present invention, $R^6$ is halo, $C_2$-$C_8$ alkynyl, carbocyclyl, or $-SR^{16}$; and all other variables are as defined in formula I, I-a or I-b, or as defined in any one of the embodiments above.

In another embodiment of the present invention, $R^6$ is halo, $C_2$-$C_3$ alkynyl, $C_3$-carbocyclyl, or —$SR^{16}$ wherein $R^{16}$ is $C_1$-$C_2$ alkyl; and all other variables are as defined in formula I, I-a or I-b, or as defined in any one of the embodiments above.

In an embodiment of the present invention, $R^{6'}$ is H, halo, or $C_1$-$C_3$ alkyl; and all other variables are as defined in formula I, I-a or I-b, or as defined in any one of the embodiments above.

In an embodiment of the present invention, p is 1 or 2; and all other variables are as defined in formula I, I-a or I-b, or as defined in any one of the embodiments above.

In another embodiment of the present invention, $X^4$ is

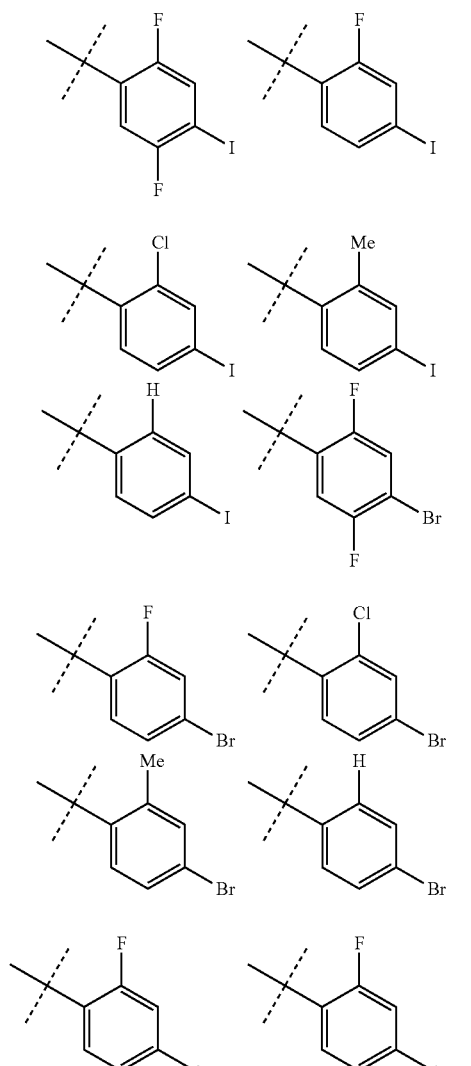

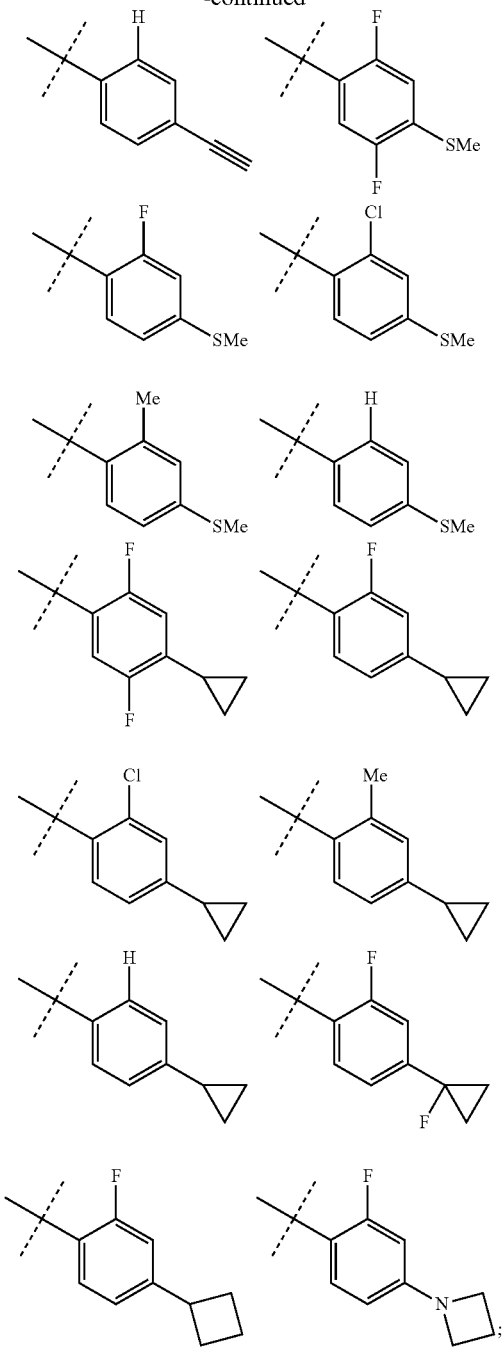

and all other variables are as defined in formula I, I-a or I-b, or as defined in any one of the embodiments above.

In another embodiment of the present invention, $X^4$ is

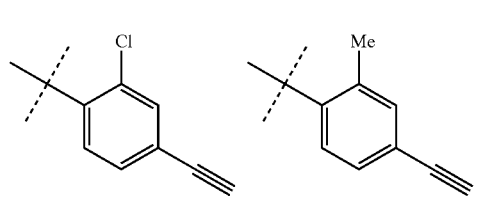

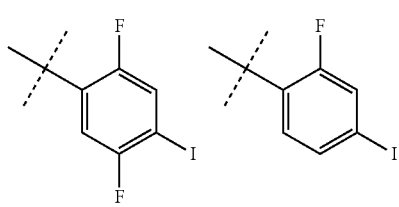

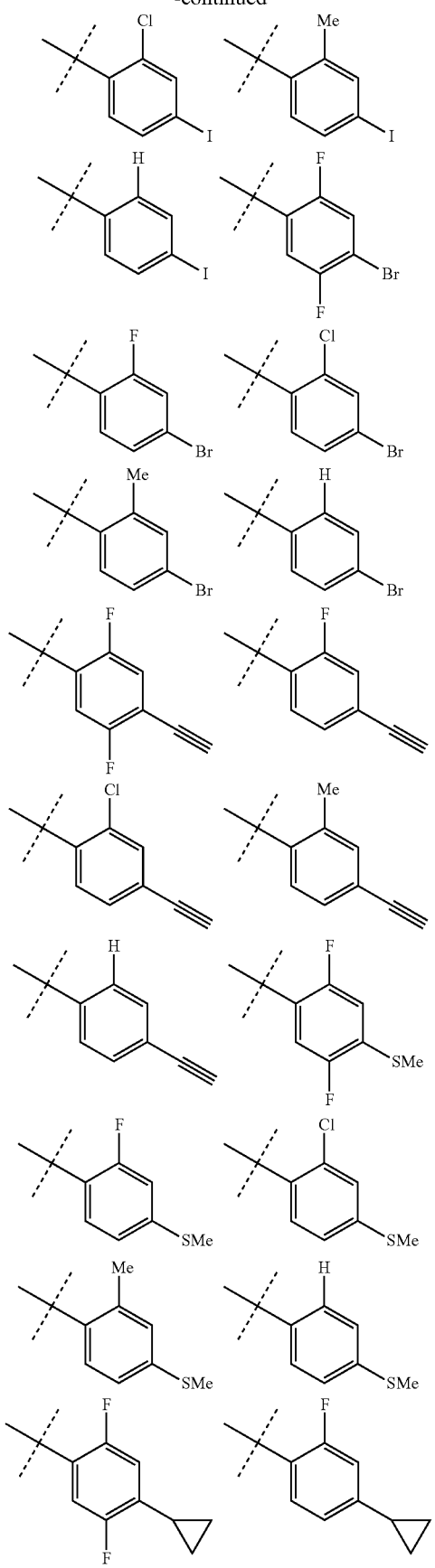
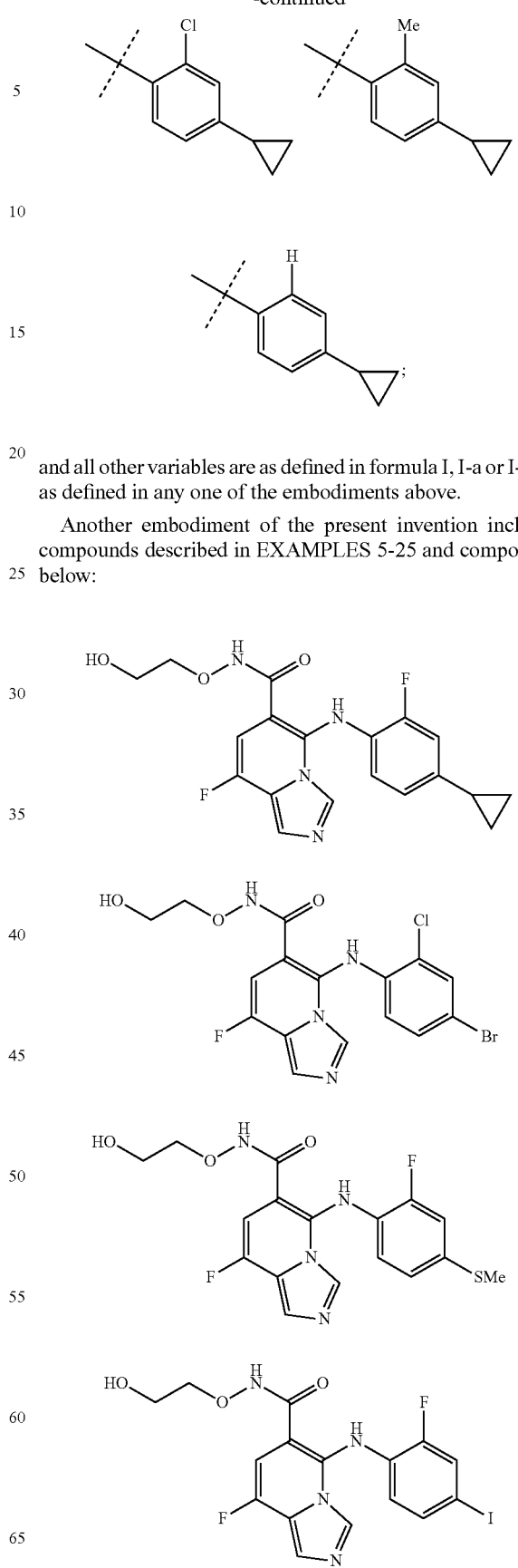
and all other variables are as defined in formula I, I-a or I-b, or as defined in any one of the embodiments above.
Another embodiment of the present invention includes compounds described in EXAMPLES 5-25 and compounds below:

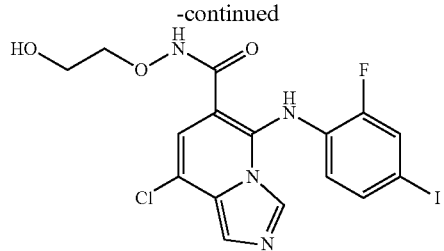
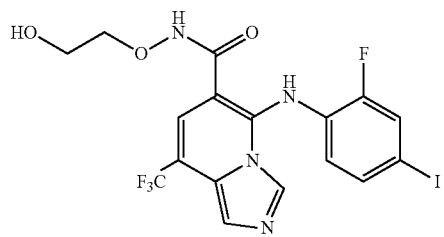
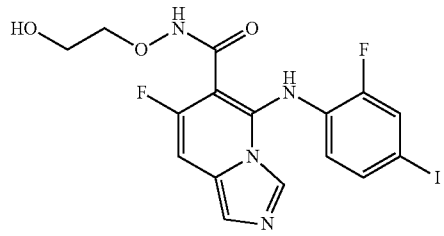
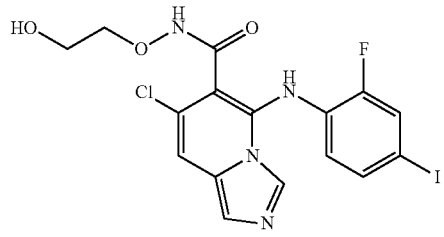
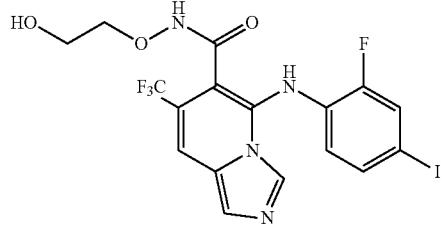
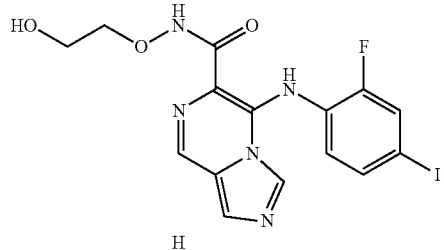
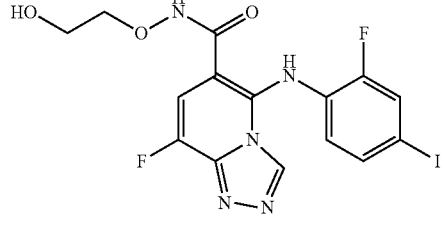
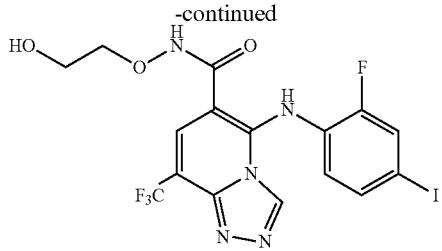
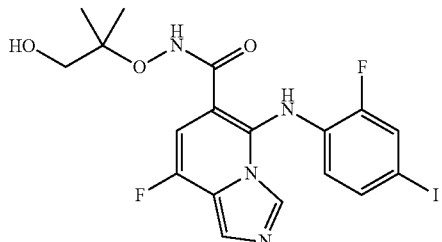
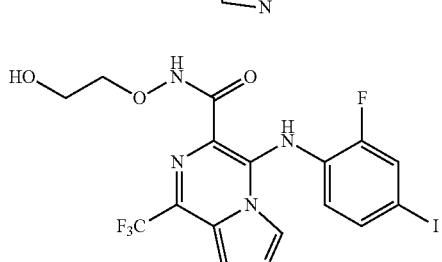
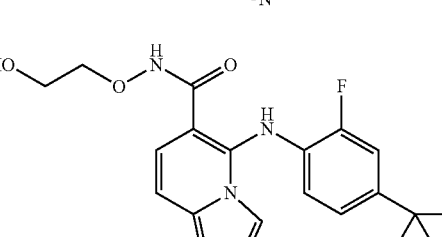
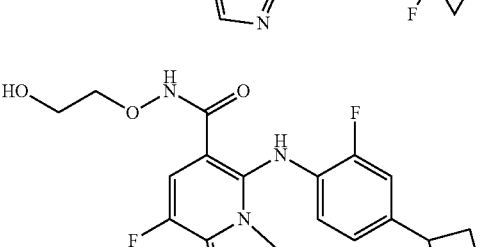
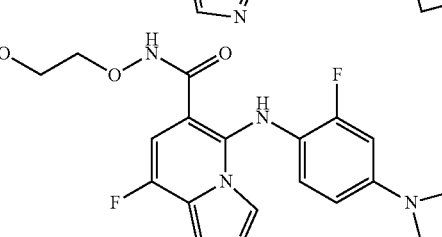
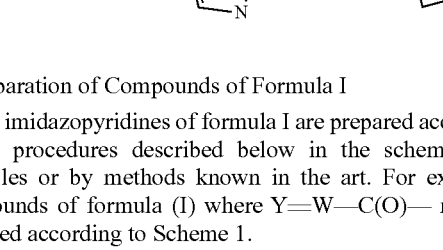
Preparation of Compounds of Formula I
The imidazopyridines of formula I are prepared according to the procedures described below in the schemes and examples or by methods known in the art. For example, compounds of formula (I) where Y=W—C(O)— may be prepared according to Scheme 1.

Scheme 1
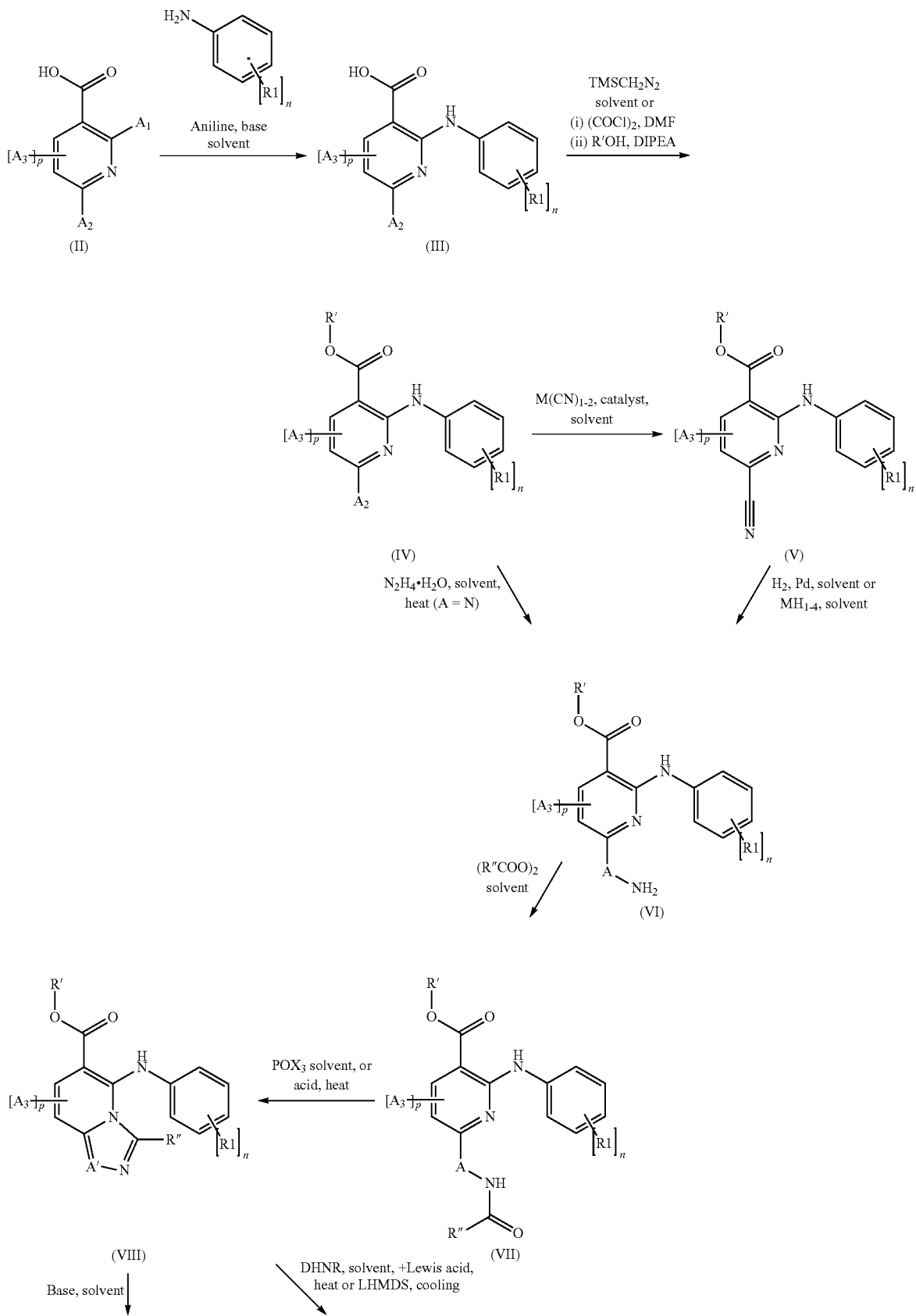

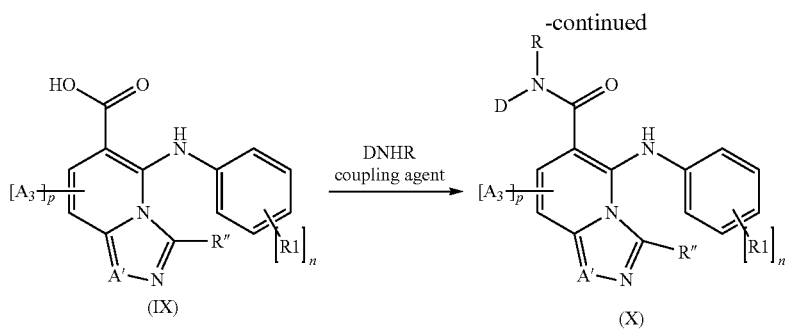

(IX) → (X)

DNHR coupling agent

R' = Methyl, ethyl or lower alkyl
R" = H, methyl, ethyl or lower alkyl, $CF_3$
R1 = appropriate substitutent n = 0-4
A = $CH_2$ or NH
A' = CH or N
X = Halogen
$A_1/A_2$ = halogen or other leaving group
$A_3$ = halogen or other appropriate substituent
p = 0, 1 or 2
M = metal
DNHR may be but is not limited to a broad
range of functionalised hydroxylamines [e.g. (XII)] and amines Nicotinic acids of formula (II) may be obtained commercially or prepared using methods described in the literature. The acids (II) may be reacted with anilines (incorporating appropriate substituents R1), in the presence of a base such as LiHMDS, in a solvent such as THF, at a temperature of from −78° C. to 25° C. to give acids of formula (III). Nicotinic esters (IV) may be prepared from nicotinic acids (III) by reaction with an alkylating agent such as trimethylsilyl diazomethane in a solvent such as toluene, at a temperature of from 0° C. to 50° C. 2-Anilino-6-cyanopyridines of formula (V) may be prepared from 6-halo pyridines (IV) by reaction with an inorganic cyanide such as zinc cyanide, in the presence of a transition metal catalyst such as $Pd(PPh_3)_4$, in a solvent such as DMF, at a temperature of from 50° C. to reflux temperature, or under microwave irradiation at a temperature of from 70° C. to 200° C. Cyanopyridines (V) may be reduced to give 2-aminomethylpyridines (VI), A=$CH_2$, by reduction with hydrogen at a pressure of from 1 to 5 atmospheres, in the presence of a catalyst such as palladium on carbon, in a solvent such as methanol or acetic acid, with or without added strong acid such as concentrated hydrochloric acid. Alternatively, the cyanopyridines (V) may be converted to 2-aminomethylpyridines by reacting with an inorganic metal hydride such as sodium borohydride, in the presence of a metal salt such as cobalt chloride, in a solvent such as methanol, at a temperature of from 0° C. to room temperature. Alternatively compounds of formula (VI), A=NH, may be prepared from compounds of formula (IV) by reaction with hydrazine hydrate, in a solvent such as ethanol, at a temperature of from 0° C. to reflux.

Compounds (VII) may be prepared from compounds (VI) by reaction with an anhydride such as acetic anhydride, or mixed anhydride such as formic-acetic anhydride, in a solvent such as tetrahydrofuran, at a temperature of from 0° C. to reflux. Compounds of formula (VIII) may be prepared from compounds (VII) by reaction with a chlorinating agent such as phosphorous oxychloride, in a solvent such as toluene, at a temperature of from 25° C. to reflux. Alternatively compounds of formula (VIII) may be prepared from compounds of formula (VII) by reaction with an acid such as formic acid, neat or in a solvent such as dioxane, at a temperature of from 50° C. to reflux. Compounds of formula (IX) can be obtained from compounds of formula (VIII) by reaction with a base such as sodium hydroxide, in a solvent such as ethanol or methanol, at a temperature of from room temperature up to reflux temperature.

Compounds of formula (IX) can be reacted with a functionalised hydroxylamine of formula (XII) (commercially available or prepared according to Scheme 5, 6 and 7) or an amine, and a suitable coupling agent, such as O-(7-aza-benzo-triazol-1-yl)-N,N,N',N'-tetra-methyluronium hexafluoro-phosphate, N-(3-dimethylaminopropyl)-N'-ethylcarbodiimide hydrochloride or N,N'-dicyclohexylcarbodiimide in the presence of N-hydroxy-1,2,3-benzotriazole, in the presence of a suitable base such as diisopropylethylamine or triethylamine in an inert solvent, such as tetrahydrofuran, N,N-dimethylformamide, or dichloromethane at a temperature of about room temperature, to obtain the compounds of formula (X). Compounds of formula (X) can be obtained directly from compounds of formula (VIII) by reaction with an amine or hydroxylamine DNHR in the presence of a Lewis acid such as trimethyl aluminium, in a solvent such as DCM, at a temperature of from room temperature up to reflux temperature. Alternatively, compounds of formula (X) may be prepared from compounds of formula (VIII) by treatment with a functionalized hydroxylamine in the presence of a base such as lithium bis(trimethylsilyl)amide in a solvent such as THF at a temperature of from −78° C. to 25° C.

Additionally, compounds of formula (I) where Y is W—C(O)— may be prepared according to Scheme 2.

Scheme 2

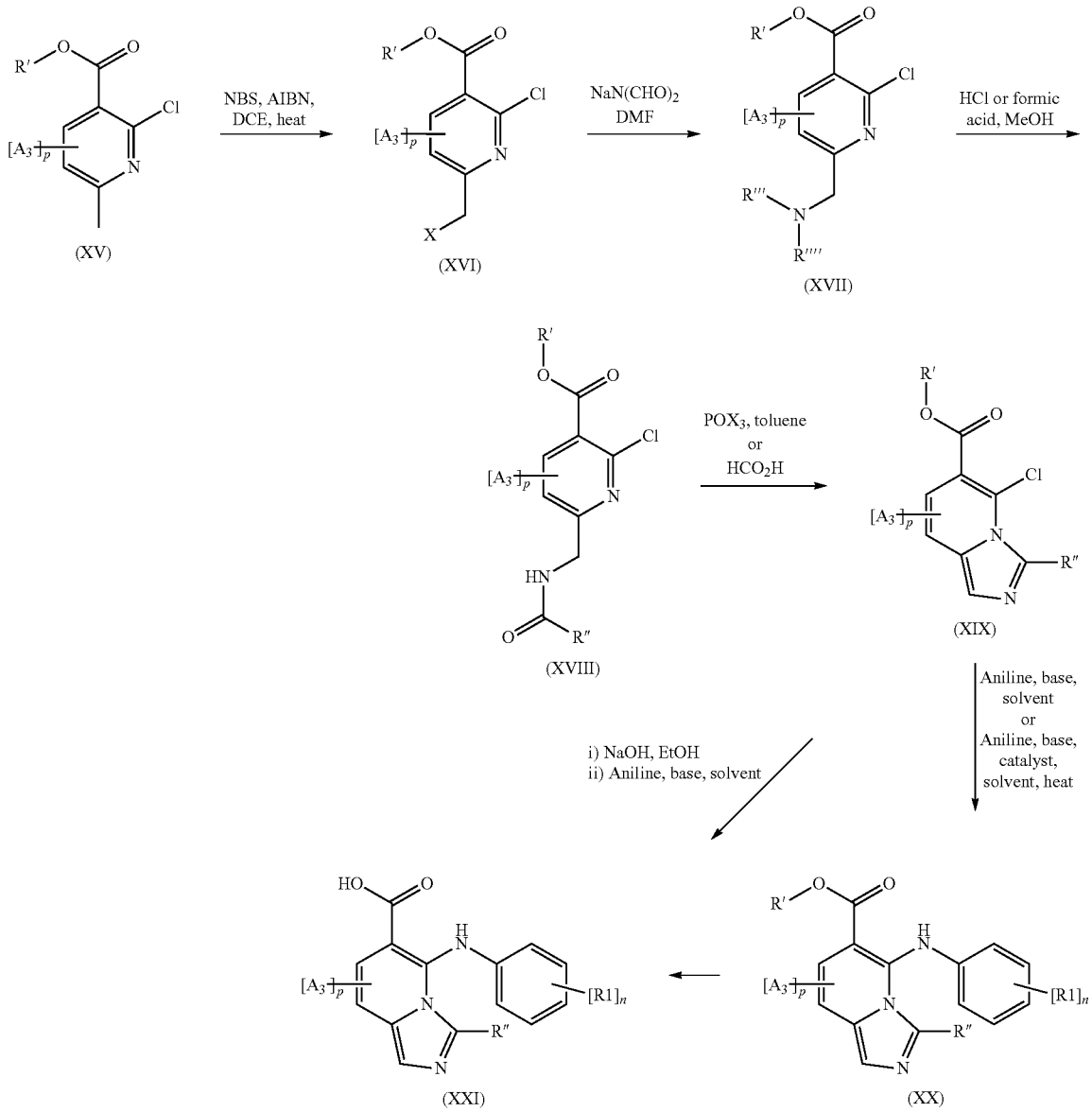

$A_3$ = halogen or other appropriate substituent
p = 1 or 2
R" = H, methyl, ethyl or lower alkyl, CF$_3$
R1 = appropriate substituent
n = 0-4
X = halogen
R' = Me, Et, tBu, lower alkyl
R''' = H, CHO, COR"
R'''' = H, CHO, CO$_2$R'
R''' = R'''' = N$_2$ Compounds of formula (XV) may be obtained commercially or prepared using methods described in the literature. Compounds of formula (XVI) may be prepared from compounds of formula (XV) by reaction with a halogenating agent such as N-bromo succinimide or 1,3-dibromo-5,5-dimethylhydantoin in the presence of a catalyst such as AIBN or benzoyl peroxide in a solvent such as dichloroethane or carbon tetrachloride using activation by light or heat at a temperature of from room temperature to reflux. Alternatively, compounds of formula (XVI) may be obtained from compounds of formula (XV) in a two step procedure by first formation of the pyridine N-oxide using an oxidizing agent such as 3-chloro-peroxy benzoic acid in a solvent such as DCM at a temperature of about room temperature. The intermediate N-oxides may be converted to halomethylpyridines of formula (XVI) by reaction with a chlorinating agent such as phosphorous oxychloride. Compounds of formula (XVII) may be prepared from compounds of formula (XVI) by reaction with a protected form of ammonia such as potassium phthalimide or sodium diformyl imide in a solvent such as DMF at a temperature of from −5° C. to 50° C. When R'''═H and R''''═C(═O)H compounds of formula (XVII) may be converted to formyl amino nicotinic esters of formula (XVIII) by treatment with an acid such as formic acid or hydrochloric acid in a solvent such as methanol at a temperature of from room temperature to reflux. Compounds of formula (XVIII) may be cyclised to imidazopyridines of formula (XIX) by reaction with a phosphorous oxyhalide such as phosphorous oxychloride in a solvent such as toluene at a temperature of from 50° C. to reflux. Alternatively, the cyclisation maybe effected using an acid such as formic acid or acetic acid, neat, at a temperature of from 25° C. to reflux. Imidazopyridine-5-anilino esters of formula (XX) may be prepared from halides of formula (XIX) by reaction with an aniline (incorporating appropriate substituents R1), in the presence of a base such as lithium bis(trimethylsilyl)amide in a solvent such as THF at a temperature of from −78° C. to room temperature. Alternatively, compounds of formula (XX) may be prepared from compounds of formula (XIX) by reaction with an aniline (incorporating appropriate substituents R1), in the presence of a catalyst such as tris(dibenzylideneacetone)dipalladium (0), a base such as potassium phosphate, a ligand such as 2-dicyclohexylphosphino-2',6'-(diisopropoxy)biphenyl, in a suitable solvent such as toluene, at a temperature of from room temperature to the reflux temperature of the solvent, or under microwave irradiation at a temperature of from 70° C. to 150° C. Acids of formula (XXI) may be prepared from esters of formula (XX) using the methods described for the conversion of compounds of formula (VIII) to compounds of formula (IX) in Scheme 1. Alternatively, acids of formula (XXI) may be prepared from compounds of formula (XIX) first by saponification using the methods described for the conversion of compounds of formula (VIII) to compounds of formula (IX) followed by treatment with an aniline (incorporating appropriate substituents R1), in the presence of a base such as lithium (bistrimethylsilyl)amide in a solvent such as THF at a temperature of from −78° C. to room temperature.

Anilino acids of formula (XXI) may be converted to compounds of formula (X) using the methods described for the conversion of compounds of formula (IX) to compounds of formula (X) in Scheme 1. In addition, esters of formula (XX) may be converted to compounds of formula (X) using the methods described for the conversion of compounds of formula (VIII) to compounds of formula (X) in Scheme 1.

Compounds of formula (XVI) and (XVII) may be prepared according to Scheme 3.

Scheme 3

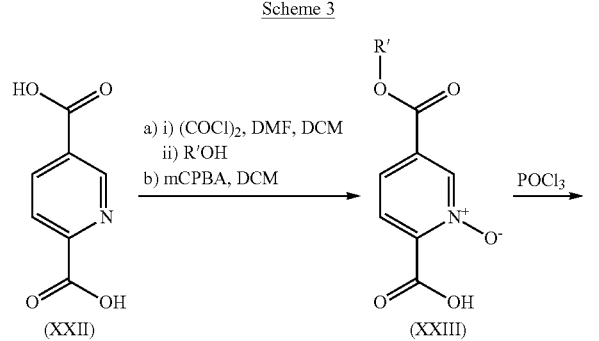

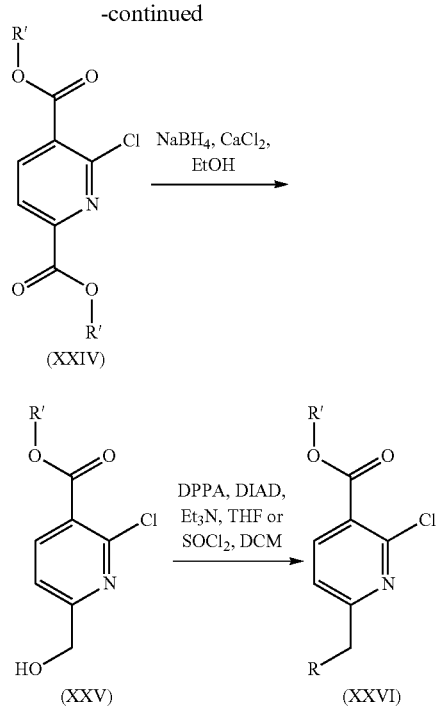

R' = Me, Et, lower alkyl
R = Cl, Br, (Formula (XVI) X = Cl or Br)
R = N₃, NH₂ (Formula (XVII) R''' = R'''' = N2 or H)

Compounds of formula (XXIII) may be prepared from compounds of formula (XXII). Compounds of formula (XXII) are first esterified by formation of the bis-acid chloride using oxalyl chloride with catalytic DMF, in a solvent such as DCM, at a temperature of about room temperature followed by quench with an alcohol such as methanol. The resultant bis-ester intermediate may then be oxidized to compounds of formula (XXIII) by reaction with an oxidizing agent such as meta-chloro peroxybenzoic acid in a solvent such as DCM at a temperature of from 0° C. to room temperature. Compounds of formula (XXV) may be prepared from compounds of formula (XXIV) by reduction with a metal hydride such as sodium borohydride in the presence of an additive such as calcium chloride, in a solvent such as ethanol, at a temperature of from 0° C. to room temperature. Compounds of formula (XXV) may be converted to compounds of formula (XXVI) where R═Cl by halogenation using a sulfonyl chloride such as thionyl chloride in a solvent such as dichloromethane, at a temperature of from −5° C. to room temperature. Compounds of formula (XXVI) where R═N₃ may be obtained from compounds of formula (XXV) by reaction with an azide such as diphenyl phosphoryl azide, in the presence of a diazocarboxylate such as diisopropyl azodicarboxylate, in the presence of a base such as triethylamine, in a solvent such as THF at a temperature of about room temperature. Compounds of formula (XXVI) where R═N₃ may be converted to compounds of formula (XXVI) where R═NH₂ by treatment with a reducing agent such as triphenyl phosphine in a solvent such as THF at a temperature of from room temperature to reflux.

Compounds of formula (I) where Y is R⁸SO₂NH— may be prepared according to Scheme 4.

Scheme 4

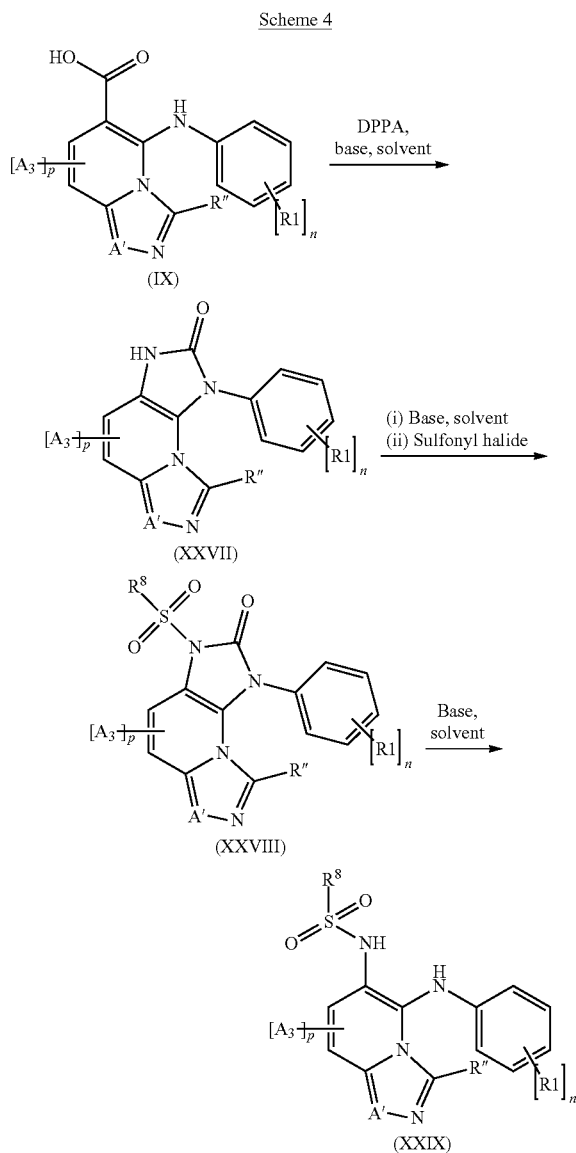

R″ = H, methyl, ethyl or lower alkyl, CF$_3$
R1 = appropriate substituent n = 0-4
A′ = CH or N
A$_3$ = halogen or other appropriate substituent
p = 0, 1 or 2

Compounds of formula (XXVII) may be prepared from compounds of formula (IX) by treatment with diphenylphosphoryl azide in a solvent such as toluene, in the presence of a base such as triethylamine. Compounds of formula (XXVIII) may be prepared from compounds of formula (XXVII) by treatment with a base such as sodium hydride, in a solvent such as DMF, followed by reaction with a sulfonyl chloride (appropriately substituted). Compounds of formula (XXIX) may be prepared from compounds of formula (XXVIII) by deprotection using a base such as sodium hydroxide, in a solvent such as DMF, at a temperature of from 50° C. to 150° C.

Hydroxylamines of formula (XII) may be prepared using methods described in the literature or the synthetic route outlined in Scheme 5.

Scheme 5

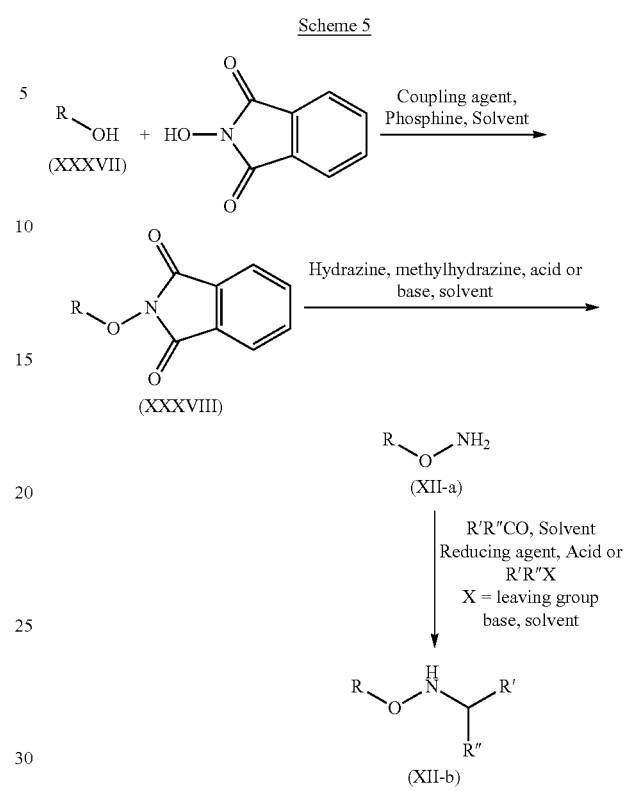

Primary or secondary alcohols of general formula (XXXVII) may be prepared using methods described in the literature. The alcohols may be reacted with N-hydroxy phthalimide using a phosphine and coupling reagent such as diethyl azodicarboxylate to provide compounds of general formula (XXXVIII). Compounds of general formula (XXXVIII) may be deprotected using hydrazine, methyl hydrazine, an acid such as hydrochloric acid or a base such as aqueous ammonia to provide hydroxylamines of general formula (XII-a).

Compounds of formula (XII-a) may be further modified by reductive amination with aldehydes or ketones using a reducing agent such as sodium triacetoxy borohydride, sodium cyanoborohydride, or borane-pyridine in a solvent such as dichloroethane at a temperature of from ambient temperature to reflux to provide hydroxylamines of general formula (XII-b). In addition, compounds of formula (XII-a) may be further modified by alkylation with an alkyl halide in the presence of a base such as triethylamine, in a solvent such as dichloromethane, to provide hydroxylamines of general formula (XII-b).

Alternatively, hydroxylamines of formula (XII-a) may be prepared according to Scheme 6.

Scheme 6

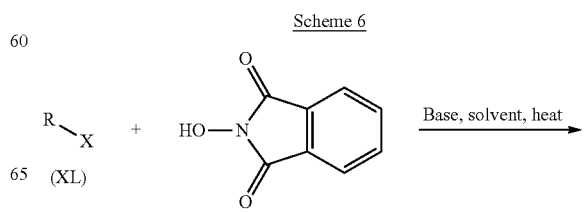

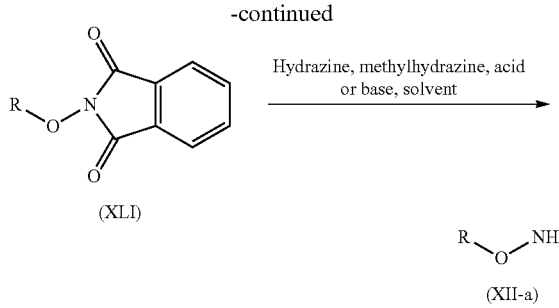

(XLI)

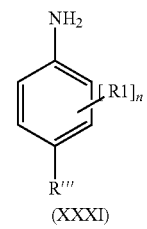

(XXXI)

Where R1 is an optional substituent group,
n = 0-4
M = Metal
X = halogen
R''' = alkyl, cycloalkyl, vinyl, SiMe₃

Alkyl halides of formula (XL) may be reacted with N-hydroxy phthalimide in the presence of a base such as potassium carbonate in a solvent such as dimethyl sulfoxide at a temperature of from 10° C. to 50° C. Compounds of formula (XLI) may be converted to compounds of formula (XII) using the methods described for the conversion of compounds of formula (XXXVIII) to compounds of formula (XII) in Scheme 5.

Alternatively, compounds of formula (XII-a) may be prepared according to Scheme 7.

Substituted 1-chloro-4-nitro benzene may be reacted with a metal R'''MXn, such as cyclopropyl boronic acid or hexamethyldisilazane, in a solvent such as xylene, using a catalyst such as tetrakis(triphenylphosphine)palladium, at a temperature of from room temperature to reflux to give compounds of formula (XXX). The nitro group may be reduced using methods described in the literature such as reaction under an atmosphere of hydrogen, at a pressure of from 1 to 5 atmospheres, in the presence of a catalyst such as palladium on carbon, and in a solvent such as ethanol or ethyl acetate, at room temperature to give compounds of formula (XXXI).

Alternatively, anilines of formula (LV) may be prepared according to Scheme 9.

Scheme 7

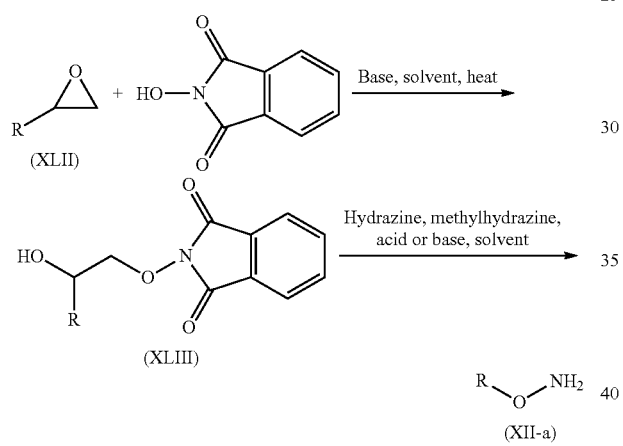

Scheme 9

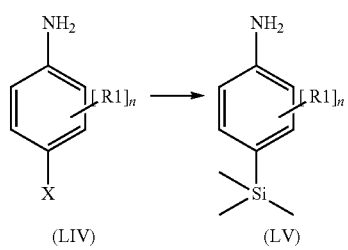

X = Br, I

Compounds of formula (XLII) may be reacted with N-hydroxy phthalimide in the presence of a catalytic amount of a base such as DIPEA and a co-catalyst such as tetra-butyl ammonium bromide in a solvent such as toluene at a temperature of form 50° C. to reflux. Compounds of formula (XLIII) may be converted to compounds of formula (XII) using the methods described for the conversion of compounds of formula (XXXVIII) to compounds of formula (XII) in Scheme 5.

Anilines of general formula (XXXI) used in condensations and cross-coupling reactions described above may be prepared by using methods described in the literature or according to Scheme 8.

Scheme 8

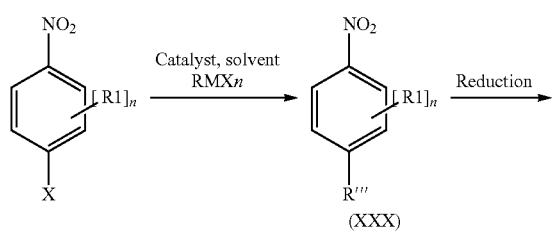

4-Bromo or iodo anilines of formula (LIV) may be reacted with at least 2 equivalents of a strong organometallic base such as n-butyllithium in a solvent such as THF at a temperature of from −100° C. to −20° C. followed by quench of the intermediate aryl lithium species with an electrophile such as trimethyl silyl chloride to give compounds of formula (LV).

It will be appreciated that where appropriate functional groups exist, compounds of formula (I) or any intermediates used in their preparation may be further derivatised by one or more standard synthetic methods employing substitution, oxidation, reduction, or cleavage reactions. Particular substitution approaches include conventional alkylation, arylation, heteroarylation, acylation, sulfonylation, halogenation, nitration, formylation and coupling procedures.

For example, aryl bromide or chloride groups may be converted to aryl iodides using a Finkelstein reaction employing an iodide source such as sodium iodide, a catalyst such as copper iodide and a ligand such as trans-N,N-dimethyl-1,2-cyclohexane diamine in a solvent such as 1,4-dioxane and heating the reaction mixture at reflux temperature. Aryl trialkylsilanes may be converted to aryl iodides by treating the silane with an iodide source such as iodine monochloride in a solvent such as dichloromethane with or without Lewis acid such as silver tetrafluoroborate at a temperature from −40° C. to reflux.

In a further example primary amine (—NH$_2$) groups may be alkylated using a reductive alkylation process employing an aldehyde or a ketone and a borohydride, for example sodium triacetoxyborohydride or sodium cyanoborohydride, in a solvent such as a halogenated hydrocarbon, for example 1,2-dichloroethane, or an alcohol such as ethanol, where necessary in the presence of an acid such as acetic acid at around ambient temperature. Secondary amine (—NH—) groups may be similarly alkylated employing an aldehyde.

In a further example, primary amine or secondary amine groups may be converted into amide groups (—NHCOR' or NRCOR') by acylation. Acylation may be achieved by reaction with an appropriate acid chloride in the presence of a base, such as triethylamine, in a suitable solvent, such as dichloromethane, or by reaction with an appropriate carboxylic acid in the presence of a suitable coupling agent such HATU (O-(7-azabenzotriazol-1-ye-N,N,N',N'-tetramethyluronium hexafluorophosphate) in a suitable solvent such as dichloromethane. Similarly, amine groups may be converted into sulfonamide groups (—NHSO$_2$R' or NR"SO$_2$R') by reaction with an appropriate sulfonyl chloride in the presence of a suitable base, such as triethylamine, in a suitable solvent such as dichloromethane. Primary or secondary amine groups can be converted into urea groups (—NHCONR'R" or NRCONR'R") by reaction with an appropriate isocyanate in the presence of a suitable base such as triethylamine, in a suitable solvent, such as dichloromethane.

An amine (—NH$_2$) may be obtained by reduction of a nitro (—NO$_2$) group, for example by catalytic hydrogenation, using for example hydrogen in the presence of a metal catalyst, for example palladium on a support such as carbon in a solvent such as ethyl acetate or an alcohol e.g. methanol. Alternatively, the transformation may be carried out by chemical reduction using for example a metal, e.g. tin or iron, in the presence of an acid such as hydrochloric acid.

In a further example, amine (—CH$_2$NH$_2$) groups may be obtained by reduction of nitriles (—CN), for example by catalytic hydrogenation using for example hydrogen in the presence of a metal catalyst, for example palladium on a support such as carbon, or Raney nickel, in a solvent such as an ether e.g. a cyclic ether such as tetrahydrofuran, at a temperature from 78° C. to the reflux temperature of the solvent.

In a further example, amine (—NH$_2$) groups may be obtained from carboxylic acid groups (—CO$_2$H) by conversion to the corresponding acyl azide (—CON$_3$), Curtius rearrangement and hydrolysis of the resultant isocyanate (—N=C=O).

Aldehyde groups (—CHO) may be converted to amine groups (—CH$_2$NR'R")) by reductive amination employing an amine and a borohydride, for example sodium triacetoxyborohydride or sodium cyanoborohydride, in a solvent such as a halogenated hydrocarbon, for example dichloromethane, or an alcohol such as ethanol, where necessary in the presence of an acid such as acetic acid at around ambient temperature.

In a further example, aldehyde groups may be converted into alkenyl groups (—CH=CHR') by the use of a Wittig or Wadsworth-Emmons reaction using an appropriate phosphorane or phosphonate under standard conditions known to those skilled in the art.

Aldehyde groups may be obtained by reduction of ester groups (such as —CO$_2$Et) or nitriles (—CN) using diisobutylaluminium hydride in a suitable solvent such as toluene. Alternatively, aldehyde groups may be obtained by the oxidation of alcohol groups using any suitable oxidising agent known to those skilled in the art.

Ester groups (—CO$_2$R') may be converted into the corresponding acid group (—CO$_2$H) by acid- or base-catalused hydrolysis, depending on the nature of R. If R is t-butyl, acid-catalysed hydrolysis can be achieved for example by treatment with an organic acid such as trifluoroacetic acid in an aqueous solvent, or by treatment with an inorganic acid such as hydrochloric acid in an aqueous solvent.

Carboxylic acid groups (—CO$_2$H) may be converted into amides (CONHR' or CONR'R") by reaction with an appropriate amine in the presence of a suitable coupling agent, such as HATU, in a suitable solvent such as dichloromethane.

In a further example, carboxylic acids may be homologated by one carbon (i.e CO$_2$H to CH$_2$CO$_2$H) by conversion to the corresponding acid chloride (—COCl) followed by Arndt-Eistert synthesis.

In a further example, —OH groups may be generated from the corresponding ester (e.g. —CO$_2$R'), or aldehyde (—CHO) by reduction, using for example a complex metal hydride such as lithium aluminium hydride in diethyl ether or tetrahydrofuran, or sodium borohydride in a solvent such as methanol. Alternatively, an alcohol may be prepared by reduction of the corresponding acid (—CO$_2$H), using for example lithium aluminium hydride in a solvent such as tetrahydrofuran, or by using borane in a solvent such as tetrahydrofuran.

Alcohol groups may be converted into leaving groups, such as halogen atoms or sulfonyloxy groups such as an alkylsulfonyloxy, e.g. trifluoromethylsulfonyloxy or arylsulfonyloxy, e.g. p-toluenesulfonyloxy group using conditions known to those skilled in the art. For example, an alcohol may be reacted with thioyl chloride in a halogenated hydrocarbon (e.g. dichloromethane) to yield the corresponding chloride. A base (e.g. triethylamine) may also be used in the reaction.

In another example, alcohol, phenol or amide groups may be alkylated by coupling a phenol or amide with an alcohol in a solvent such as tetrahydrofuran in the presence of a phosphine, e.g. triphenylphosphine and an activator such as diethyl-, diisopropyl, or dimethylazodicarboxylate. Alternatively alkylation may be achieved by deprotonation using a suitable base e.g. sodium hydride followed by subsequent addition of an alkylating agent, such as an alkyl halide.

Aromatic halogen substituents in the compounds may be subjected to halogen-metal exchange by treatment with a base, for example a lithium base such as n-butyl or t-butyl lithium, optionally at a low temperature, e.g. around −78° C., in a solvent such as tetrahydrofuran, and then quenched with an electrophile to introduce a desired substituent. Thus, for example, a formyl group may be introduced by using N,N-dimethylformamide as the electrophile. Aromatic halogen substituents may alternatively be subjected to metal (e.g. palladium or copper) catalysed reactions, to introduce, for example, acid, ester, cyano, amide, aryl, heteraryl, alkenyl, alkynyl, thio- or amino substituents. Suitable procedures which may be employed include those described by Heck, Suzuki, Stille, Buchwald or Hartwig.

Aromatic halogen substituents may also undergo nucleophilic displacement following reaction with an appropriate nucleophile such as an amine or an alcohol. Advantageously, such a reaction may be carried out at elevated temperature in the presence of microwave irradiation.

The compounds of the present invention are tested for their capacity to inhibit MEK activity and activation (primary assays) and for their biological effects on growing cells (secondary assays) as described below. The compounds of the present invention having IC$_{50}$ of less than 5 μM (more preferably less than 0.1 μM, most preferably less than 0.01 μM) in the MEK activity assay of Example 1, IC$_{50}$ of less than 5 (more preferably less than 1 μM, even more preferably less than 0.1 μM, most preferably less than 0.01 μM) in the MEK activation assay of Example 2, $EC_{50}$ of less than 10 µM (more preferably less than 1 µM, even more preferably less than 0.5 µM, most preferably less than 0.1 µM) in the cell proliferation assay of Example 3, and/or $EC_{50}$ of less than 10 µM (more preferably less than 1 µM, even more preferably less than 0.5 most preferably less than 0.1 µM) in the ERK phosphorylation assay of Example 4, are useful as MEK inhibitors.

The present invention includes a composition (e.g., a pharmaceutical composition) comprising a compound of formula I (and/or solvates and/or salts thereof) and a carrier (a pharmaceutically acceptable carrier). The present invention also includes a composition (e.g., a pharmaceutical composition) comprising a compound of formula I (and/or solvates and/or salts thereof) and a carrier (a pharmaceutically acceptable carrier), further comprising a second chemotherapeutic and/or a second anti-inflammatory agent such as those described herein. The present compositions are useful for inhibiting abnormal cell growth or treating a hyperproliferative disorder in a mammal (e.g., human). The present compositions are also useful for treating inflammatory diseases in a mammal (e.g., human).

The present compounds (such as any one of the title compounds of EXAMPLES 5-25) and compositions are also useful for treating an autoimmune disease, destructive bone disorder, proliferative disorders, infectious disease, viral disease, fibrotic disease or neurodegenerative disease in a mammal (e.g., human). Examples of such diseases/disorders include, but are not limited to, diabetes and diabetic complications, diabetic retinopathy, retinopathy of prematurity, age-related macular degeneration, hemangioma, idiopathic pulmonary fibrosis, rhinitis and atopic dermatitis, renal disease and renal failure, polycystic kidney disease, congestive heart failure, neurofibromatosis, organ transplant rejection, cachexia, stroke, septic shock, heart failure, organ transplant rejection, Alzheimer's disease, chronic or neuropathic pain, and viral infections such as HIV, hepatitis (B) virus (HBV), human papilloma virus (HPV), cytomegalovirus (CMV), and Epstein-Barr virus (EBV). Chronic pain, for purposes of the present invention includes, but is not limited to, idiopathic pain, and pain associated with chronic alcoholism, vitamin deficiency, uremia, hypothyroidism, inflammation, arthritis, and post-operative pain. Neuropathic pain is associated with numerous conditions which include, but are not limited to, inflammation, postoperative pain, phantom limb pain, burn pain, gout, trigeminal neuralgia, acute herpetic and postherpetic pain, causalgia, diabetic neuropathy, plexus avulsion, neuroma, vasculitis, viral infection, crush injury, constriction injury, tissue injury, limb amputation, arthritis pain, and nerve injury between the peripheral nervous system and the central nervous system.

The present compounds (such as any one of the title compounds of EXAMPLES 5-25) and compositions are also useful for treating pancreatitis or kidney disease (including proliferative glomerulonephritis and diabetes-induced renal disease) in a mammal (e.g., human).

The present compounds (such as any one of the title compounds of EXAMPLES 5-25) and compositions are also useful for the prevention of blastocyte implantation in a mammal (e.g., human).

The present invention includes a method of inhibiting abnormal cell growth or treating a hyperproliferative disorder in a mammal (e.g., human) comprising administering to said mammal a therapeutically effective amount of a compound of formula I (and/or solvates and/or salts thereof) or a composition thereof. Also included in the present invention is a method of treating an inflammatory disease in a mammal (e.g., human) comprising administering to said mammal a therapeutically effective amount of a compound of formula I (and/or solvates and/or salts thereof) or a composition thereof.

The present invention includes a method of inhibiting abnormal cell growth or treating a hyperproliferative disorder in a mammal (e.g., human) comprising administering to said mammal a therapeutically effective amount of a compound of formula I (and/or solvates and/or salts thereof) or a composition thereof, in combination with a second chemotherapeutic agent such as those described herein. The present invention also includes a method of treating an inflammatory disease in a mammal (e.g., human) comprising administering to said mammal a therapeutically effective amount of a compound of formula I (and/or solvates and/or salts thereof) or a composition thereof, in combination with a second anti-inflammatory agent such as those described herein.

The present invention includes a method of treating an autoimmune disease, destructive bone disorder, proliferative disorders, infectious disease, viral disease, fibrotic disease or neurodegenerative disease in a mammal (e.g., human) comprising administering to said mammal a therapeutically effective amount of a compound of formula I (and/or solvates and salts thereof) or a composition thereof, and optionally further comprising a second therapeutic agent. Examples of such diseases/disorders include, but are not limited to, diabetes and diabetic complications, diabetic retinopathy, retinopathy of prematurity, age-related macular degeneration, hemangioma, idiopathic pulmonary fibrosis, rhinitis and atopic dermatitis, renal disease and renal failure, polycystic kidney disease, congestive heart failure, neurofibromatosis, organ transplant rejection, cachexia, stroke, septic shock, heart failure, organ transplant rejection, Alzheimer's disease, chronic or neuropathic pain, and viral infections such as HIV, hepatitis (B) virus (HBV), human papilloma virus (HPV), cytomegalovirus (CMV), and Epstein-Barr virus (EBV).

The present invention includes a method of treating pancreatitis or kidney disease (including proliferative glomerulonephritis and diabetes-induced renal disease) in a mammal (e.g., human) comprising administering to said mammal a therapeutically effective amount of a compound of formula I (and/or solvates and salts thereof) or a composition thereof, and optionally further comprising a second therapeutic agent.

The present invention includes a method for preventing of blastocyte implantation in a mammal (e.g., human) comprising administering to said mammal a therapeutically effective amount of a compound of formula I (and/or solvates and salts thereof) or a composition thereof, and optionally further comprising a second therapeutic agent.

The present invention includes a method of using the present compounds for in vitro, in situ, and in vivo diagnosis or treatment of mammalian cells, organisms, or associated pathological conditions.

It is also believed that the compounds of the present invention can render abnormal cells more sensitive to treatment with radiation for purposes of killing and/or inhibiting the growth of such cells. Accordingly, this invention further relates to a method for sensitizing abnormal cells in a mammal (e.g., human) to treatment with radiation which comprises administering to said mammal an amount of a compound of formula I (and/or solvates and salts thereof) or a composition thereof, which amount is effective is sensitizing abnormal cells to treatment with radiation.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, inhalation and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or in combination with one or more chemotherapeutic or anti-inflammatory agents, for example those described herein. Such conjoint treatment may be achieved by way of the simultaneous, sequential or separate dosing of the individual components of treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Ester, Pa., 15.sup.th Edition (1975).

EXAMPLES

| Abbreviations | |
| --- | --- |
| nBuLi | n-Butyllithium |
| $CDCl_3$ | Deuterated chloroform |
| $CD_3OD$ | Deuterated methanol |
| $CH_2Cl_2$ | Dichloromethane |
| DCM | Dichloromethane |
| DIPEA | Diisopropylethylamine |
| DMF | Dimethylformamide |
| DMSO | Dimethylsulfoxide |
| Dppf | 1,1'-Bis(diphenylphosphino)ferrocene |
| EDCI | 1-Ethyl-3-(3'-dimethylaminopropyl)carbodiimide hydrochloride |
| $Et_3N$ | Triethylamine |
| $Et_2O$ | Diethyl ether |
| HATU | O-(7-Azabenzotriazol-1-yl)-N,N,N',N'-tetramethyluronium hexafluorophosphate |
| HCl | Hydrochloric acid |
| HMN | Diatomaceous earth |
| HOBt | 1-Hydroxybenzotriazole |
| $H_2SO_4$ | Sulfuric acid |
| ICl | Iodine monochloride |
| IMS | Industrial methylated spirits |
| LHMDS | Lithium bis(trimethylsilyl)amide |
| MeOH | Methanol |
| $MgSO_4$ | Magnesium sulfate |
| $NaHCO_3$ | Sodium hydrogen carbonate |
| $Na_2SO_4$ | Sodium sulfate |
| NBS | N-Bromosuccinimide |
| $Pd(PPh_3)_4$ | Tetrakis(triphenylphosphine)palladium(0) |
| $Pd_2dba_3$ | Tris-(dibenzylideneacetone)dipalladium(0) |
| $Pd(dppf)Cl_2$ | [1,1'-Bis(diphenylphosphino)ferrocene]dichloropalladium(II) |
| Si-PPC | Pre-packed silica flash chromatography cartridge: Isolute ® SPE, Biotage SNAP ® or ISCO Redisep ® |
| SCX-2 | Isolute ® silica-based sorbent with a chemically bonded propylsulfonic acid functional group. |
| THF | Tetrahydrofuran |

General Experimental Conditions $^1$H NMR spectra were recorded at ambient temperature using a Varian Unity Inova (400 MHz) spectrometer with a triple resonance 5 mm probe. Chemical shifts are expressed in ppm relative to tetramethylsilane. The following abbreviations have been used: br=broad signal, s=singlet, d=doublet, dd=double doublet, t=triplet, q=quartet, m=multiplet.

High Pressure Liquid Chromatography—Mass Spectrometry (LCMS) experiments to determine retention times ($R_T$) and associated mass ions were performed using one of the following methods.

Method A: Experiments performed on a Waters Micromass ZQ quadrupole mass spectrometer linked to a Hewlett Packard HP 1100 LC system with diode array detector. This system uses a Higgins Clipeus 5 micron C18 100×3.0 mm column and a 1 ml/minute flow rate. The initial solvent system was 95% water containing 0.1% formic acid (solvent A) and 5% acetonitrile containing 0.1% formic acid (solvent B) for the first minute followed by a gradient up to 5% solvent A and 95% solvent B over the next 14 minutes. The final solvent system was held constant for a further 5 minutes.

Method B: Experiments performed on a Waters Platform LC quadrupole mass spectrometer linked to a Hewlett Packard HP1100 LC system with diode array detector and 100 position autosampler using a Phenomenex Luna C18(2) 30×4.6 mm column and a 2 ml/minute flow rate. The solvent system was 95% water containing 0.1% formic acid (solvent A) and 5% acetonitrile containing 0.1% formic acid (solvent B) for the first 0.50 minutes followed by a gradient up to 5% solvent A and 95% solvent B over the next 4 minutes. The final solvent system was held constant for a further 0.50 minutes.

Method C: Experiments performed on a PE Sciex API 150 EX quadrupole mass spectrometer linked to a Shimadzu LC-10AD LC system with diode array detector and 225 position autosampler using a Kromasil C18 50×4.6 mm column and a 3 ml/minute flow rate. The solvent system was a gradient starting with 100% water with 0.05% TFA (solvent A) and 0% acetonitrile with 0.0375% TFA (solvent B), ramping up to 10% solvent A and 90% solvent B over 4 minutes. The final solvent system was held constant for a further 0.50 minutes.

Method D: Experiments performed on an Agilent Technologies liquid chromatography mass spectrometer linked to an Agilent Technologies Series 1200 LC system with diode array detector using a Zorbax 1.8 micron SB-C18 30×2.1 mm column with a 1.5 ml/minute flow rate. Method D1: The initial solvent system was 95% water containing 0.05% trifluoroacetic acid (solvent A) and 5% acetonitrile containing 0.05% trifluoroacetic acid (solvent B), followed by a gradient up to 5% solvent A and 95% solvent B over 1.5 minutes. The final solvent system was held constant for a further 1 minute. Method D2: The initial solvent system was 95% water containing 0.05% trifluoroacetic acid (solvent A) and 5% acetonitrile containing 0.05% trifluoroacetic acid (solvent B), followed by a gradient up to 5% solvent A and 95% solvent B over 3.0 minutes. The final solvent system was held constant for a further 1 minute.

Method E: Experiments performed on an Agilent Technologies liquid chromatography mass spectrometer linked to an Agilent Technologies Series 1200 LC system with diode array detector using a Zorbax 1.8 micron SB-C18 30×2.1 mm column with a 0.6 ml/minute flow rate. Method E1: The initial solvent system was 95% water containing 0.05% trifluoroacetic acid (solvent A) and 5% acetonitrile containing 0.05% trifluoroacetic acid (solvent B), followed by a gradient up to 5% solvent A and 95% solvent B over 9.0 minutes. The final solvent system was held constant for a further 1 minute. Method E2: The initial solvent system was 95% water containing 0.05% trifluoroacetic acid (solvent A) and 5% acetonitrile containing 0.05% trifluoroacetic acid (solvent B), followed by a gradient up to 5% solvent A and 95% solvent B over 20.0 minutes. The final solvent system was held constant for a further 1 minute.

Microwave experiments were carried out using a Personal Chemistry Ernrys Iniatiator™ or Optimizer™, which uses a single-mode resonator and dynamic field tuning, both of which give reproducibility and control. Temperature from 40-250° C. can be achieved, and pressures of up to 20 bar can be reached.

Example 1

MEK Assay (MEK Activity Assay)

Constitutively activated human mutant MEK1 expressed in insect cells is used as source of enzymatic activity at a final concentration in the kinase assay of 15 nM.

The assay is carried out for 30 minutes in the presence of 50 μM ATP using recombinant GST-ERK1 produced in *E. Coli* as substrate. Phosphorylation of the substrate is detected and quantified using HTRF reagents supplied by Cisbio. These consist of an anti-GST antibody conjugated to allophycocyanin (XL665) and an anti-phospho (Thr202/Tyr204) ERK antibody conjugated to europium-cryptate. These are used at a final concentration of 4 μg/ml and 0.8 μg/ml respectively. The anti-phospho antibody recognises ERK1 dually phosphorylated on Thr202 and Tyr204. When both antibodies are bound to ERK1 (i.e. when the substrate is phosphorylated), energy transfer from the cryptate to the allophycocyanin occurs following excitation at 340 nm, resulting in fluorescence being emitted that is proportional to the amount of phosphorylated substrate produced. Fluorescence is detected using a multiwell fluorimeter.

Compounds are diluted in DMSO prior to addition to assay buffer and the final DMSO concentration in the assay is 1%.

The $IC_{50}$ is defined as the concentration at which a given compound achieves 50% inhibition of control. $IC_{50}$ values are calculated using the XLfit software package (version 2.0.5).

Title compounds of Examples 5-20 and 22-24 exhibited an $IC_{50}$ of less than 0.5 μM in the assay described in Example 1. Some of these compounds exhibited an $IC_{50}$ of less than 0.1 μM in the assay described in Example 1. Title compounds of Examples 21 and 25 exhibited an $IC_{50}$ of less than 10 μM in the assay described in Example 1.

Example 2 bRaf Assay (MEK Activation Assay)

Constitutively activated bRaf mutant expressed in insect cells is used as source of enzymatic activity.

The assay is carried out for 30 minutes in the presence of 200 μM ATP using recombinant GST-MEK1 produced in *E. Coli* as substrate. Phosphorylation of the substrate is detected and quantified using HTRF, and reagents are supplied by Cisbio. These consist of an anti-GST antibody conjugated to allophycocyanin (XL665) and an anti-phospho (Ser217/Ser221) MEK antibody conjugated to europium-cryptate. The anti-phospho antibody recognises MEK dually phosphorylated on Ser217 and Ser221 or singly phosphorylated on Ser217. When both antibodies are bound to MEK (i.e. when the substrate is phosphorylated), energy transfer from the cryptate to the allophycocyanin occurs following excitation at 340 nm, resulting in fluorescence being emitted that is proportional to the amount of phosphorylated substrate produced. Fluorescence is detected using a multi-well fluorimeter.

Compounds are diluted in DMSO prior to addition to assay buffer and the final DMSO concentration in the assay is 1%.

The $IC_{50}$ is defined as the concentration at which a given compound achieves 50% inhibition of control. $IC_{50}$ values are calculated using the XLfit software package (version 2.0.5).

Example 3

Cell Proliferation Assay

Compounds are tested in a cell proliferation assay using the following cell lines:
HCT 116 human colorectal carcinoma (ATCC)
A375 human malignant melanoma (ATCC)

Both cell lines are maintained in DMEM/F12 (1:1) media (Gibco) supplemented with 10% FCS at 37° C. in a 5% $CO_2$ humidified incubator.

Cells are seeded in 96-well plates at 2,000 cells/well and after 24 hours they are exposed to different concentrations of compounds in 0.83% DMSO. Cells are grown for a further 72 h, and an equal volume of CellTiter-Glo reagent (Promega) is added to each well. This lyses the cells and generates a luminescent signal proportional to the amount of ATP released (and therefore proportional to the number of cells in the well) that can be detected using a multi-well luminometer.

The EC$_{50}$ is defined as the concentration at which a given compound achieves 50% inhibition of control. IC$_{50}$ values are calculated using the XLfit software package (version 2.0.5).

In this assay, title compounds of Example 5-8, 11-13 and 18-20 exhibited an EC$_{50}$ of less than 0.5 μM in both cell lines. Some of the title compounds of Examples 5-8, 11-13 and 18-20 exhibited an EC$_{50}$ of less than 0.1 μM in both cell lines. Title compounds of Examples 9-10 and 14-17 exhibited an EC$_{50}$ of less than 0.8 μM in the HCT116 cell line.

Example 4

Phospho-ERK Cell-Based Assay

Compounds are tested in a cell-based phospho-ERK ELISA using the following cell lines:

HCT116 human colorectal carcinoma (ATCC)

A375 human malignant melanoma (ATCC)

Both cell lines are maintained in DMEM/F12 (1:1) media (Gibco) supplemented with 10% FCS at 37° C. in a 5% CO$_2$ humidified incubator.

Cells are seeded in 96-well plates at 2,000 cells/well and after 24 h they are exposed to different concentrations of compounds in 0.83% DMSO. Cells are grown for a further 2 h or 24 h, fixed with formaldehyde (2% final) and permeabilised with methanol. Following blocking with TBST-3% BSA, fixed cells are incubated with primary antibody (anti-phospho ERK from rabbit) over-night at 4° C. Cells are incubated with Propidium Iodide (DNA fluorescent dye) and detection of cellular p-ERK is performed using an anti-rabbit secondary antibody conjugated to the fluorescent Alexa Fluor 488 dye (Molecular probes). The fluorescence is analysed using the Acumen Explorer (TTP Labtech), a laser-scanning microplate cytometer, and the Alexa Fluor 488 signal is normalised to the PI signal (proportional to cell number).

The EC$_{50}$ is defined as the concentration at which a given compound achieves a signal half way between the baseline and the maximum response. EC$_{50}$ values are calculated using the XLfit software package (version 2.0.5).

In this assay, title compounds of Examples 5-8, 11-12 and 18-20 exhibited an EC$_{50}$ of less than 0.02 μM in both cell lines. Some of the title compounds of Examples 5-8, 11-12 and 18-20 exhibited an EC$_{50}$ of less than 0.01 μM in both cell lines. Title compounds of Examples 9-10 and 13-17 exhibited an EC$_{50}$ of less than 0.05 μM in the HCT116 cell line.

Synthesis of Imidazo[1,5-a]Pyridines

2-Fluoro-4-trimethylsilanyl-phenylamine

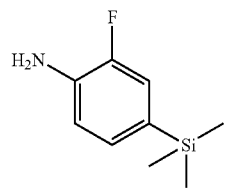

Method A, Step 1:
(3-Fluoro-4-nitro-phenyl)-trimethylsilane

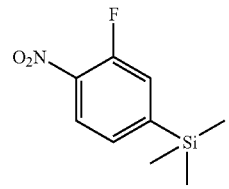

4-Chloro-2-fluoronitrobenzene (97.2 g, 0.55 mol) was dissolved in xylenes (208 ml) and hexamethyldisilane (306 g, 2.78 mol) was added. Argon was bubbled through the mixture for 20 min, then Pd(PPh$_3$)$_4$ (16.2 g, 14 mmol) was added and the mixture was heated under continuous flow of argon at 150° C. for 1 hour. A balloon of argon was then fitted and the mixture was heated at 150° C. for a further 60 hours. After cooling the mixture was diluted with diethyl ether and filtered through a pad of silica. The filter cake was washed with further diethyl ether, and the combined filtrates were concentrated in vacuo. Purification of the resultant residue by flash chromatography (SiO$_2$, 98:1:1 pentane:CH$_2$Cl$_2$:Et$_2$O eluent) gave the title compound as an orange oil (76.7 g). Impure chromatography fractions were combined and concentrated, and then subjected to vacuum distillation (b.p. 110° C., 6 mbar) to give a further portion of the title compound as an orange oil (7.2 g, overall 83.9 g, 71%). $^1$H NMR δ (DMSO-d$_6$): 0.30 (9 H, s), 7.56 (1 H, d, J=8.02 Hz), 7.67 (1 H, dd, J=11.49, 1.14 Hz), 8.10 (1 H, t, J=7.66 Hz).

Method A, Step 2:
2-Fluoro-4-trimethylsilanyl-phenylamine

A slurry of 10% wt. palladium on carbon (4.0 g) in IMS (25 mL) was added to a solution of (3-fluoro-4-nitro-phenyl)-trimethylsilane (62.0 g, 0.29 mol) in IMS (250 mL) and the reaction mixture flushed with nitrogen five times then hydrogen three times. The reaction mixture was then stirred under 3 bar pressure of hydrogen at room temperature for 4 hours. The reaction mixture was then purged with nitrogen again before filtering through a pad of Celite® with ethyl acetate washings. The filtrate was concentrated under reduced pressure to give the title compound as a light brown oil (53.0 g, quantitative). $^1$H NMR (CDCl$_3$) 7.16-7.09 (1H, m), 7.10 (1 H, d, J=7.75 Hz), 6.81 (1 H, t, J=8.16 Hz), 3.78 (2 H, s), 0.26 (9 H, s).

Method B, Step 2:
2-Fluoro-4-trimethylsilanyl-phenylamine

To a solution of 4-bromo-2-fluoro-phenylamine (114 g, 0.6 mol) in anhydrous THF (750 mL) at −78° C. was added a 1.6M solution of nBuLi in hexanes (1500 mL, 2.4 mol) dropwise keeping the internal temperature below −60° C., under an inert atmosphere. The reaction mixture was treated dropwise with TMSCl (256 mL, 2.0 mol), keeping the internal temperature below −60° C. The reaction mixture was allowed to warm to 0° C. over a 1 hour period and poured into ice-cold 2M HCl (ca. 1 L). The mixture was vigorously stirred for 10 min, then the organic layer was separated, and washed with water and a saturated solution of potassium carbonate, dried (Na$_2$SO$_4$), filtered and concentrated to give the title compound as a light brown oil (89 g, 81%).

4-Cyclopropyl-2-fluoro-phenylamine

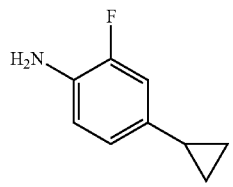

Step 1: Trifluoro-methanesulfonic acid 3-fluoro-4-nitro-phenyl ester

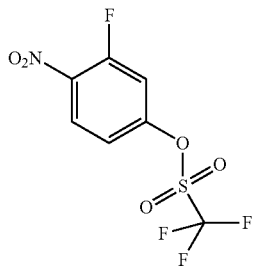 [SMILES: O=[N+]([O-])c1ccc(OS(=O)(=O)C(F)(F)F)cc1F]

To a solution of 3-fluoro-4-nitrophenol (12.5 g, 80 mmol) and trifluoromethane sulfonic anhydride (26.8 mL, 160 mmol) in DCM (300 mL) at 0° C. was added triethylamine (44.6 mL, 320 mmol) dropwise. The reaction mixture was stirred at 0° C. for 2 hours then allowed to warm to room temperature and stirred for 18 hours. The reaction was quenched by the addition of water and the mixture extracted with DCM. The organic layer was separated, washed with water and then dried (MgSO$_4$), filtered and concentrated in vacuo. The resultant residue was subjected to flash chromatography (Si-PPC, gradient 0 to 40% ethyl acetate in cylcohexane) to give the title compound as a yellow oil (12.8 g, 56% yield). $^1$H NMR (DMSO-d$_6$, 400 MHz) 8.39 (1 H, t, J=8.83 Hz), 8.12 (1 H, dd, J=11.09, 2.65 Hz), 7.67 (1 H, ddd, J=9.20, 2.62, 1.52 Hz).

Step 2: 4-Cyclopropyl-2-fluoro-1-nitro-benzene

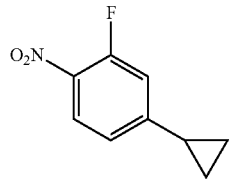 [SMILES: O=[N+]([O-])c1ccc(C2CC2)cc1F]

A stirred suspension of trifluoro-methanesulfonic acid 3-fluoro-4-nitro-phenyl ester (5.6 g, 19 mmol), cyclopropyl boronic acid (2.09 g, 23.3 mmol) Pd(dppf)Cl$_2$ (1.24 g, 1.5 mmol) and 2M aqueous cesium carbonate (30 mL, 60 mmol) in toluene (20 mL) was degassed before being heated at 90° C. under an argon atmosphere for 2.5 hours. The reaction mixture was allowed to cool to room temperature before filtering through a pad of Celite®, washing with ethyl acetate. The filtrate was washed (water, brine), and then dried (MgSO$_4$), filtered and concentrated in vacuo. The resultant residue was subjected to flash chromatography (Si-PPC, gradient 0-30% ethyl acetate in pentane) to give the title compound as a yellow solid (2.79 g, 81%). $^1$H NMR (DMSO-d$_6$, 400 MHz) 8.03 (1 H, t, J=8.39 Hz), 7.28 (1 H, dd, J=13.19, 1.91 Hz), 7.16 (1 H, dd, J=8.61, 1.90 Hz), 2.14-2.05 (1 H, m), 1.21-1.05 (2 H, m), 0.92-0.82 (2 H, m).

Step 3: 4-Cyclopropyl-2-fluoro-phenylamine

A slurry of palladium on carbon (200 mg, 10% wt.) in IMS was added to a degassed solution of 4-cyclopropyl-2-fluoro-1-nitro-benzene (1.45 g, 8 mmol) in IMS (50 mL), the atmosphere was evacuated and back-filled with nitrogen then re-evacuated and back-filled with hydrogen. The reaction mixture was stirred under 1 atmosphere pressure of hydrogen at room temperature for 24 hours before filtering through a pad of Celite® then washing with ethyl acetate. The filtrate was concentrated in vacuo to give the title compound as a pale purple residue (1.19 g, 98%). $^1$H NMR (CDCl$_3$, 400 MHz) 6.72-6.63 (3 H, m), 3.56 (2 H, s), 1.83-1.75 (1 H, m), 0.93-0.82 (2 H, m), 0.59-0.54 (2 H, m).

2-(2-Fluoro-4-trimethylsilanyl-phenylamino)-6-formylaminomethyl-nicotinic acid methyl ester

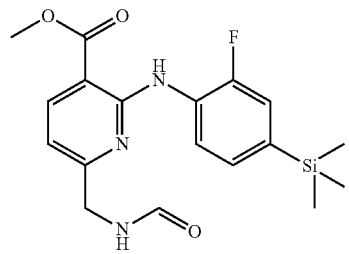

Step 1: 6-Chloro-2-(2-fluoro-4-trimethylsilanyl-phenylamino)nicotinic acid

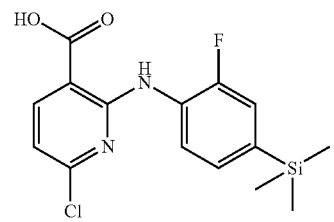

To a cold (−78° C.) solution of 2-fluoro-4-trimethylsilanyl-phenylamine (64.7 g, 353 mmol) in anhydrous THF (170 mL) was added a solution of LHMDS (555 mL, 1 M in hexanes, 555 mmol) dropwise over 45 minutes under a nitrogen atmosphere. After 2.5 hours at 78° C., a solution of 2,6-dichloro-nicotinic acid (33.8 g, 177 mmol) in anhydrous THF (100 mL) was added. The reaction mixture was stirred at −78° C. for 30 minutes then allowed to warm to room temperature. After 18 hours stirring at room temperature the reaction was quenched with crushed ice and the pH adjusted to pH 1 by the addition of concentrated HCl (ca. 90 mL). The resultant solution was extracted with ethyl acetate and the organic layer washed with water followed by brine, dried (Na$_2$SO$_4$), filtered and evaporated in vacuo. The resultant residue was triturated three times successively with methanol and filtered to afford the title compound as a yellow solid (46.7 g, 78%). LCMS (method B): R$_T$=4.83 min, M+H$^+$=339.

Step 2: 6-Chloro-2-(2-fluoro-4-trimethylsilanyl-phenylamino)-nicotinic acid methyl ester

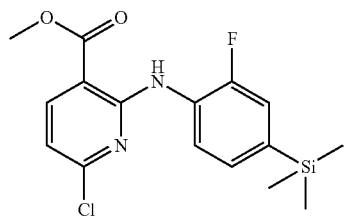

To a suspension of 6-chloro-2-(2-fluoro-4-trimethylsilanyl-phenylamino)-nicotinic acid (33.7 g, 99.5 mmol) in dichloromethane (500 mL) at 0° C. was added DIPEA (17.1 mL, 99.5 mmol). The reaction mixture was stirred for 10 minutes, then DMF (2 mL) and oxalyl chloride (8.7 mL, 99.5 mmol) were added dropwise (CAUTION: EFFERVESCENCE). The reaction mixture was stirred at room temperature for 2 hours and then added dropwise to a solution of DIPEA (17.1 mL, 99.5 mmol) in MeOH (500 mL) at 0° C. over a 45 minutes period. The reaction mixture was stirred at room temperature for 18 hours before being concentrated in vacuo. The resultant residue was dissolved in ethyl acetate and washed with a saturated aqueous solution of sodium hydrogen carbonate, followed by water, then brine, dried (Na$_2$SO$_4$), filtered and evaporated in vacuo to afford the title compound as a brown foam which was used without purification into the next step (36.4 g). LCMS (method B) R$_T$=5.35 min, M+H$^+$=353.

Step 3: 6-Cyano-2-(2-fluoro-4-trimethylsilanyl-phenylamino)-nicotinic acid methyl ester

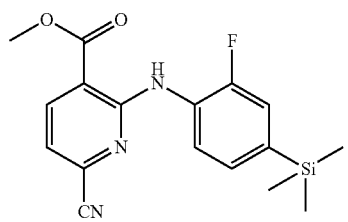

A degassed suspension of 6-chloro-2-(2-fluoro-4-trimethylsilanyl-phenylamino)-nicotinic acid methyl ester (4.8 g, 12.4 mmol), zinc cyanide (1.2 g, 10.2 mmol), and Pd(PPh$_3$)$_4$ (1.6 g, 1.36 mmol) in dimethylformamide (14 mL) was subjected to microwave irradiation at 190° C. for 20 minutes. This procedure was repeated seven times and all the reaction mixtures were combined and concentrated in vacuo. The resultant residue was dissolved in ethyl acetate and washed with a saturated aqueous solution of sodium hydrogen carbonate. The aqueous layer was separated and extracted with ethyl acetate three times. The combined organic extracts were washed with water and then brine, dried (Na$_2$SO$_4$), filtered and evaporated in vacuo. The resultant residue was subjected to flash chromatography (silica, gradient 0% to 100%, diethyl ether in pentane) to afford the title compound as a yellow solid (18.2 g). LCMS (method B): R$_T$=4.74 min, M+H$^+$=344.

Step 4: 6-Aminomethyl-2-(2-fluoro-4-trimethylsilanyl-phenylamino)nicotinic acid methyl ester

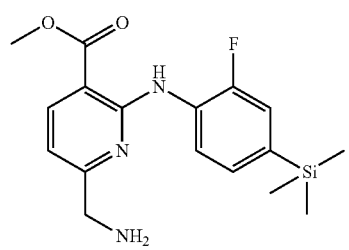

To a suspension of 6-cyano-2-(2-fluoro-4-trimethylsilanyl-phenylamino)-nicotinic acid methyl ester (13.1 g, 38.2 mmol) in methanol (285 mL) was added cobalt (II) chloride (18.2 g, 76.4 mmol). The reaction mixture was cooled to 0° C. and sodium borohydride (14.5 g, 382 mmol) was added in small portions over 20 minutes (CAUTION: EFFERVESCENCE). The reaction mixture was stirred at 0° C. for 1 hour. The reaction was quenched by the addition of concentrated hydrochloric acid (50 mL) and the mixture stirred at 0° C. for 10 minutes and at room temperature for 45 minutes. Diethylenetriamine (9 mL) was then added and the mixture stirred for a further 15 minutes. The reaction mixture was filtered to remove a white solid, which was washed with dichloromethane. The filtrate was concentrated in vacuo and the resultant residue was dissolved in ethyl acetate and washed with a saturated solution of sodium hydrogen carbonate, followed by water then brine. The organic phase was isolated, dried (Na$_2$SO$_4$), filtered and concentrated in vacuo to afford the title compound as a brown solid (13.2 g, 100%). LCMS (method B): R$_T$=2.82 min, M+H$^+$=348.

Step 5: 2-(2-Fluoro-4-trimethylsilanyl-phenylamino)-6-formylaminomethyl-nicotinic acid methyl ester A solution of 6-aminomethyl-2-(2-fluoro-4-trimethylsilanyl-phenylamino)-nicotinic acid methyl ester (13.2 g, 38.2 mmol) in formic acid (200 mL) and acetic anhydride (40 mL) was stirred at ambient temperature for 1 hour. The reaction mixture was concentrated in vacuo and the residue azeotroped with toluene. The resultant residue was dissolved in dichloromethane and washed with a saturated aqueous solution of sodium hydrogen carbonate, followed by brine. The organic phase was isolated, dried (Na$_2$SO$_4$), filtered and concentrated in vacuo to afford the title compound as a yellow solid (12.7 g, 89%). LCMS (method B): R$_T$=4.17 min, M+H$^+$=376.

5-Chloro-imidazo[1,5-a]pyridine-6-carboxylic acid methyl ester

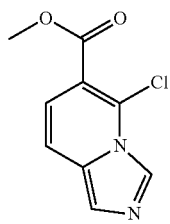

Step 1, Method A: 6-Bromomethyl-2-chloronicotinic acid methyl ester

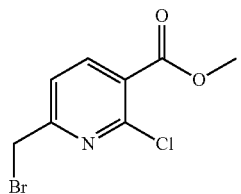

To a solution of 2-chloro-6-methylnicotinic acid methyl ester (100 g, 0.54 mol) in DCE (1.0 L) was added re-crystallised N-bromosuccinimide (124.7 g, 0.70 mol) and benzoylperoxide (13.1 g, 0.05 mol). The reaction mixture was heated at 70° C. for 16 hours, during which the reagents dissolved to give a dark red solution. The reaction mixture was diluted with saturated aqueous sodium hydrogen carbonate solution (200 mL) causing the red colour to fade to yellow. The aqueous layer was extracted with DCM (2×100 mL). The combined organic fractions were washed with brine (100 mL), dried (MgSO$_4$) and concentrated in vacuo to give the crude product (<138 g, <0.54 mol) as a yellow oil containing approximately 40% desired product. $^1$H NMR (CDCl$_3$, 400 MHz) 8.18 (1H, d, J=8.0 Hz), 7.48 (1H, d, J=7.9 Hz), 4.51 (2H, s), 3.94 (3H, s).

Step 1, Method B: Alternative method 6-Bromomethyl-2-chloronicotinic acid methyl ester

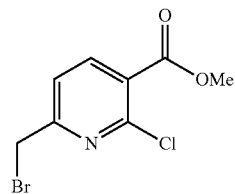 [SMILES: COC(=O)c1ccc(CBr)nc1Cl]

To a mechanically stirred solution of 2-chloro-6-methylnicotinic acid methyl ester (147 g, 0.79 mol) in DCE (1.5 L) was added 1,3-dibromo-5,5-dimethylhydantoin (181.8 g, 0.635 mol) and MEN (6.35 g, 0.04 mol). The reaction mixture was heated at 65° C. for 72 hours, during which the reagents dissolved to give a dark red/brown solution. The reaction mixture was cooled and diluted with saturated aqueous sodium hydrogen carbonate solution (1 L) causing the red colour to fade to yellow. The layers were separated, and the aqueous layer was extracted with DCM (2×750 mL). The combined organic fractions were washed with water (1 L), sat. saline (1 L), dried (MgSO$_4$) and concentrated in vacuo. The resultant yellow oil (235 g), containing approximately 46% desired product, was used crude in the next step without further purification. $^1$H NMR (CDCl$_3$, 400 MHz) 8.18 (1H, d, J=8.0 Hz), 7.48 (1H, d, J=7.9 Hz), 4.51 (2H, s), 3.94 (3H, s).

Step 2, Method A: 2-Chloro-6-diformylaminomethylnicotinic acid methyl ester

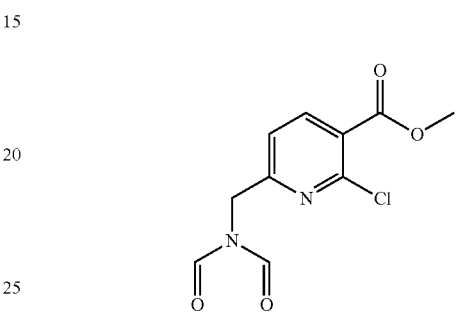

To a solution of crude 6-bromomethyl-2-chloronicotinic acid methyl ester (<138 g, <0.54 mol) in DMF (400 mL) was added sodium diformamide (56.3 g, 0.59 mol) and the reaction mixture stirred at room temperature for 16 hours. The reaction mixture rapidly darkened and a small exotherm was observed. The reaction mixture was concentrated in vacuo and the residue dissolved in ethyl acetate (200 mL). The resultant solution was washed with water (400 mL) and the aqueous layer extracted with ethyl acetate (2×200 mL). The combined organic extracts were washed with brine (100 mL), dried (MgSO$_4$) and concentrated in vacuo. The resultant residue was dry-loaded onto silica (150 g) and the residue subjected to flash chromatography (SiO$_2$ 400 g, 40% ethyl acetate in cyclohexane) to yield the title compound as a yellow solid (46 g, 33% over two steps). $^1$H NMR (CDCl$_3$, 400 MHz) 8.46 (2H, br s), 7.56 (1H, d, J=7.7 Hz), 6.66 (1H, d, J=7.9 Hz), 4.39 (2H, br s), 3.36 (3H, s).

Step 2, Method B: 2-Chloro-6-diformylaminomethylnicotinic acid methyl ester

To a solution of crude 6-bromomethyl-2-chloronicotinic acid methyl ester (235 g) in DMF (500 mL) was added sodium diformamide (82 g, 0.878 mol) portion wise, maintaining the temperature below 30° C., and the reaction mixture stirred at room temperature for 16 hours (N.B. the reaction mixture rapidly darkened and a small exotherm was observed). The reaction mixture was concentrated in vacuo and the residue dissolved in ethyl acetate (400 mL). The resultant solution was washed with water (2×400 mL) and the aqueous layer extracted with ethyl acetate (2×300 mL). The combined organic extracts were washed with brine (200 mL), dried (MgSO$_4$) and concentrated in vacuo. The resultant residue was dry-loaded onto silica (200 g) and the residue subjected to flash chromatography (SiO$_2$ 300 g, 10-30% ethyl acetate in cyclohexane) to yield the title compound as a yellow solid (90.2 g, 44% over two steps). $^1$H NMR (CDCl$_3$, 400

MHz) 8.46 (2H, br s), 7.56 (1H, d, J=7.7 Hz), 6.66 (1H, d, J=7.9 Hz), 4.39 (2H, br s), 3.36 (3H, s).

Step 3, Method A:
2-Chloro-6-formylaminomethylnicotinic acid methyl ester

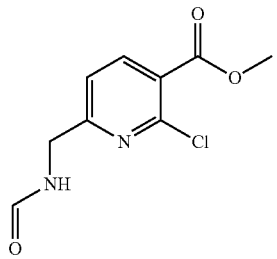

To a solution of 2-chloro-6-diformylaminomethylnicotinic acid methyl ester (53.0 g, 0.21 mol) in methanol (300 mL) was added water (3.72 mL, 0.21 mol) and formic acid (15.6 mL, 0.42 mol) before the reaction mixture was heated at reflux for 16 hours. The reaction mixture was concentrated in vacuo and the residue dissolved in ethyl acetate (200 mL). The resultant solution was washed with water (200 mL) and the aqueous layer extracted with ethyl acetate (2×100 mL). The combined organic extracts were washed with brine (100 mL), dried (MgSO$_4$) and concentrated in vacuo to yield the title compound as an orange oil which solidified on standing (42.6 g, 90%). $^1$H NMR (CDCl$_3$, 400 MHz) 8.34 (1H, s), 8.17 (1H, d, J=8.0 Hz), 7.31 (1H, d, J=7.8 Hz), 6.63 (1H, br s), 4.63 (2H, d, J=5.6 Hz), 3.96 (3H, s).

Step 3, Method B:
2-Chloro-6-formylaminomethylnicotinic acid methyl ester

To a solution of 2-chloro-6-diformylaminomethylnicotinic acid methyl ester (90.2 g, 0.352 mol) in methanol (530 mL) was added water (8 mL, 0.44 mol) and formic acid (27.6 mL, 0.73 mol) before the reaction mixture was heated at gentle reflux for 16 hours. The reaction mixture was concentrated in vacuo and the residue dissolved in ethyl acetate (400 mL). The resultant solution was washed with water (400 mL) and the aqueous layer extracted with ethyl acetate (2×200 mL). The combined organic extracts were washed with brine (300 mL), dried (MgSO$_4$) and concentrated in vacuo to yield the title compound as an orange oil which solidified on standing (79.78 g, 99%). $^1$H NMR (CDCl$_3$, 400 MHz) 8.34 (1H, s), 8.17 (1H, d, J=8.0 Hz), 7.31 (1H, d, J=7.8 Hz), 6.63 (1H, br s), 4.63 (2H, d, J=5.6 Hz), 3.96 (3H, s).

Step 4: 5-Chloroimidazo[1,5-a]pyridine-6-carboxylic acid methyl ester

To a suspension of 2-chloro-6-formylaminomethylnicotinic acid methyl ester (42.6 g, 0.19 mol) in toluene (400 mL) was added phosphorous (V) oxychloride (18.2 mL, 0.20 mol) and the reaction mixture heated at 65° C. for 1.5 hours. The reaction mixture was cooled to room temperature and diluted with ethyl acetate (200 mL) before treating with sodium hydroxide solution (2 M) to adjust pH~8. The layers were separated and the aqueous layer extracted with ethyl acetate (2×100 mL). The combined organic extracts were washed with brine (100 mL), dried (MgSO$_4$) then charcoal (~5 g) was added and the solution mixed for 5 minutes before being filtered and concentrated in vacuo to yield the title compound as a tan solid (34.4 g, 88%) $^1$H NMR (CDCl$_3$, 400 MHz) 8.52 (1H, s), 7.57 (1H, s), 7.45 (1H, d, J=9.3 Hz), 7.25 (1H, d, J=9.1 Hz), 3.97 (3H, s).

5-(2-Fluoro-4-iodophenylamino)-imidazo[1,5-a]pyridine-6-carboxylic acid

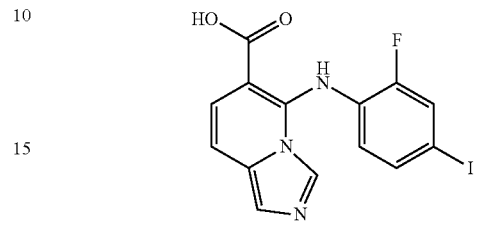

Step 1: 2-(2-Fluoro-4-iodophenylamino)-6-formylaminomethylnicotinic acid methyl ester

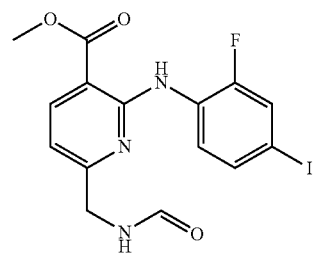 [SMILES: COC(=O)c1ccc(CNC=O)nc1Nc1ccc(I)cc1F]

To a solution of 2-(2-fluoro-4-trimethylsilanylphenylamino)-6-formylamino methyl-nicotinic acid methyl ester (10.3 g, 27.4 mmol) in DCM (275 mL) at 0° C. was added dropwise iodine monochloride as a solution in DCM (54.9 mL, 1M, 54.9 mmol). The reaction mixture was stirred at 0° C. for 1 hour. The reaction mixture was washed with aqueous sodium metabisulfite (100 mL, 0.5 M) and the aqueous layer extracted twice with ethyl acetate (2×50 mL). The combined organic extracts were washed with brine (50 mL), dried (MgSO$_4$), filtered and concentrated in vacuo to give the title compound as an orange gum (11.6 g, 100%). LCMS (Method B): R$_T$=3.72 min, M+H$^+$=430.

Step 2: 5-(2-Fluoro-4-iodophenylamino)-imidazo[1,5-a]pyridine-6-carboxylic acid methyl ester

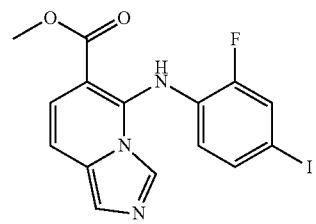 [SMILES: COC(=O)c1ccc2cncn2c1Nc1ccc(I)cc1F]

To a suspension of 2-(2-fluoro-4-iodophenylamino)-6-formylaminomethylnicotinic acid methyl ester (11.6 g, 27.4 mmol) in toluene (160 mL) was added phosphorous (V) oxychloride (5.1 mL, 54.8 mmol) and the reaction mixture heated at 95° C. for 1 hour. The reaction mixture was concentrated in vacuo and the resultant residue poured onto ice. The mixture was washed with aqueous saturated sodium hydrogen carbonate solution (40 mL) and the aqueous layer extracted twice with ethyl acetate (2×30 mL). The combined organic extracts were washed with brine (30 mL), dried (MgSO$_4$), filtered and concentrated in vacuo. The resultant residue was subjected to flash chromatography (SiO$_2$, gradient 0-70% ethyl acetate in DCM) to yield the title compound as a brown oil (5.6 g, 50%). LCMS (Method B): R$_T$=3.62 min, M+H$^+$=412.

Step 3: 5-(2-Fluoro-4-iodophenylamino)-imidazo[1,5-a]pyridine-6-carboxylic acid

To a solution of 5-(2-fluoro-4-iodophenylamino)-imidazo[1,5-a]pyridine-6-carboxylic acid methyl ester (5.6 g, 13.6 mmol) in IMS (50 mL) was added aqueous sodium hydroxide (27.2 mL, 1M, 27.2 mmol) and the reaction mixture stirred at 65° C. for 2 hours. The reaction mixture was concentrated in vacuo to remove the IMS. The resultant solution was acidified to pH ~5 by addition of aqueous hydrochloric acid (1M) causing a precipitate to form. The product was collected by filtration and dried under vacuum at 45° C. to yield the title compound as a beige solid (5.4 g, 100%). LCMS (Method B): R$_T$=2.79 min, M+H$^+$=398.

5-(2-Fluoro-4-iodophenylamino)-imidazo[1,5-a]pyridine-6-carboxylic acid methyl ester, Method A

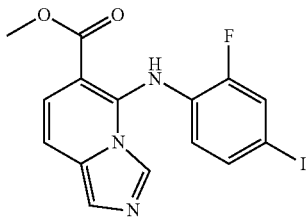 [SMILES: COC(=O)c1ccc2cncn2c1Nc1ccc(I)cc1F]

To a solution of lithium bis(trimethylsilyl)amide (9.98 mL, 1M solution, 9.98 mmol) in THF (20 mL) under nitrogen at −70° C. was added dropwise, over 15 minutes, a solution of 2-fluoro-4-iodo aniline (1.01 g, 4.28 mmol) and 5-chloro-imidazo[1,5-a]pyridine-6-carboxylic acid methyl ester (1.0 g, 4.75 mmol) in THF (20 mL) giving a bright red solution. After stirring for 30 minutes at −78° C. the reaction mixture was allowed to warm and then quenched with saturated aqueous ammonium chloride (200 mL). The mixture was extracted twice with ethyl acetate, before the combined organic extracts were dried (MgSO$_4$), filtered and concentrated in vacuo. The resultant residue was subjected to flash chromatography (Si-PPC, gradient 0-40% ethyl acetate in cyclohexane) to yield the title compound as a yellow solid (1.15 g, 65%). LCMS (Method B): R$_T$=3.54 min, M+H$^+$=412.

5-(2-Fluoro-4-iodophenylamino)-imidazo[1,5-a]pyridine-6-carboxylic acid methyl ester, Method B To a stirred suspension 2-fluoro-4-iodo aniline (53.95 g, 0.256 mol) and 5-chloro-imidazo[1,5-a]pyridine-6-carboxylic acid methyl ester (62.0 g, 0.253 mol) in THF (500 mL) under nitrogen at −78° C., a solution of lithium bis(trimethylsilyl)amide (544 mL, 1M solution, 0.544 mol) was added dropwise over 1 hr, maintaining the temperature below −65° C., giving a red/brown solution. After stirring for 30 minutes at −78° C. the reaction mixture was allowed to warm to −30° C. and then quenched with addition water (100 mL). The solvent was removed in vacuo, before diluting with water (500 ml) and the mixture was extracted with 2-methyltetrahydrofuran (2×500 mL). The combined organic extracts were washed with water, then brine, dried (MgSO$_4$), filtered and concentrated in vacuo. The resultant residue was triturated tert-butyl methyl ether (600 mL) to yield product as yellow/brown solid (87.2 g 83%). LCMS (Method B): R$_T$=3.54 min, [M+H]$^+$=412.

5-(4-Bromo-2-fluorophenylamino)-imidazo[1,5-a]pyridine-6-carboxylic acid

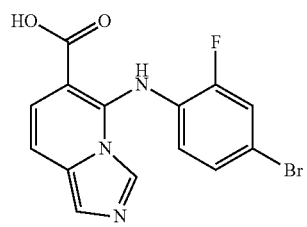

Step 1: 2-(4-Bromo-2-fluorophenylamino)-6-formylaminomethylnicotinic acid methyl ester

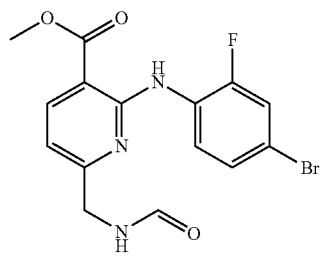 [SMILES: COC(=O)c1ccc(CNC=O)nc1Nc1ccc(Br)cc1F]

To a solution of 2-(2-fluoro-4-trimethylsilanylphenylamino)-6-formylamino methyl-nicotinic acid methyl ester (11.6 g, 30.9 mmol) in DCM (300 mL) at −30° C. was added N-bromo succinimide (5.56 g, 30.9 mmol) portionwise. The reaction mixture was stirred at −30° C. for 30 minutes. The reaction mixture was concentrated in vacuo and the residue partitioned between saturated aqueous sodium hydrogen carbonate and ethyl acetate. The organic layer was separated and washed with water, dried (Na$_2$SO$_4$), filtered and concentrated in vacuo to give the title compound as an orange gum (11.8 g, 100%). LCMS (Method B): R$_T$=3.67 min, M+H$^+$=382/384.

Step 2: 5-(4-Bromo-2-fluorophenylamino)-imidazo[1,5-a]pyridine-6-carboxylic acid methyl ester

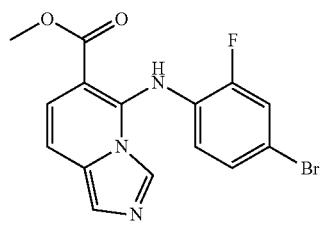

To a solution of 2-(4-Bromo-2-fluorophenylamino)-6-formylaminomethylnicotinic acid methyl ester (11.8 g, 30.9 mmol) in toluene (550 mL) was added phosphorous (V) oxychloride (3.16 mL, 34 mmol) and the reaction mixture heated at 95° C. for 1 hour. The reaction mixture was concentrated in vacuo and treated with aqueous saturated sodium hydrogen carbonate solution then extracted twice with ethyl acetate. The combined organic fractions were washed with brine, dried ($Na_2SO_4$) and concentrated in vacuo. The resultant residue was subjected to flash chromatography (Si-PPC, gradient 0-30% ethyl acetate in DCM) to yield the title compound as a brown oil (5.4 g, 49%). LCMS (Method B): $R_T$=3.56 min, M+H$^+$=364/366.

Step 3: 5-(4-Bromo-2-fluorophenylamino)-imidazo carboxylic acid

To a solution of 5-(4-Bromo-2-fluorophenylamino)-imidazo[1,5-a]pyridine-6-carboxylic acid methyl ester (5.4 g, 15 mmol) in IMS (110 mL) was added aqueous sodium hydroxide (30 mL, 1M, 30 mmol) and the reaction mixture stirred at 65° C. for 1.5 hours. The reaction mixture was concentrated in vacuo to 50 mL volume and the resultant solution was acidified to pH ~2 by addition of aqueous hydrochloric acid (1M) causing a precipitate to form. The precipitate was collected by filtration and dried under vacuum at 35° C. to yield the title compound as a dark tan solid (4.48 g, 85%). LCMS (Method B): $R_T$=2.81 min, M+H$^+$=350/352.

5-(2-Fluoro-4-cyclopropylphenylamino)-imidazo[1,5-a]pyridine-6-carboxylic acid

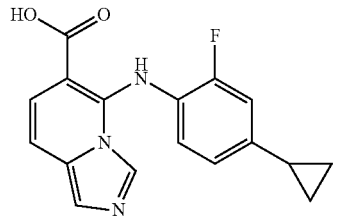 [SMILES: O=C(O)c1ccc2cncn2c1Nc1ccc(C2CC2)cc1F]

Step 1: 5-(2-Fluoro-4-cyclopropylphenylamino)-imidazo[1,5-a]pyridine-6-carboxylic acid methyl ester

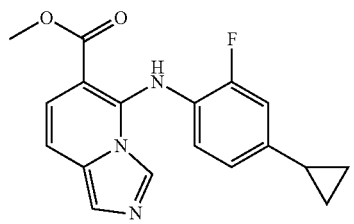 [SMILES: COC(=O)c1ccc2cncn2c1Nc1ccc(C2CC2)cc1F]

To a solution of 2-fluoro-4-cyclopropyl aniline (395 mg, 2.61 mmol) and 5-chloro-imidazo[1,5-a]pyridine-6-carboxylic acid methyl ester (500 mg, 2.37 mmol) in THF under nitrogen at −70° C. (20 mL) was added lithium bis(trimethylsilyl)amide (4.98 mL, 1M solution, 4.98 mmol) dropwise. After stirring for 1 hour at −70° C. the reaction mixture was allowed to warm and then quenched with saturated aqueous ammonium chloride. The mixture was extracted with ethyl acetate (150 mL), the organic extract dried ($Na_2SO_4$), filtered and concentrated in vacuo. The resultant residue was subjected to flash chromatography (Si-PPC, gradient 0-50% ethyl acetate in cyclohexane) to yield the title compound (573 mg, 60%). LCMS (Method B): $R_T$=3.60 min, MA-H$^+$=326.

Step 2: 5-(2-Fluoro-4-cyclopropylphenylamino)-imidazo[1,5-a]pyridine-6-carboxylic acid To a solution of 5-(2-fluoro-4-cyclopropylphenylamino)-imidazo[1,5-a]pyridine-6-carboxylic acid methyl ester (573 mg, 1.73 mmol) in methanol (20 mL) was added aqueous sodium hydroxide (10 mL, 1M, 10 mmol) and the reaction mixture stirred at 70° C. for 30 minutes. The reaction mixture was concentrated in vacuo to ~20 mL volume and the resultant solution diluted with water (20 mL) and filtered. The filtrate was acidified to pH 1 by addition of aqueous hydrochloric acid (1M) causing a precipitate to form. The precipitate was collected by filtration and dried under vacuum at 45° C. to yield the title compound as a dark tan solid (476 mg, 87%). LCMS (Method B): $R_T$=2.81 min, M+H$^+$=318.

5-(2-Fluoro-4-methansulfanyl-phenylamino)-imidazo[1,5-a]pyridine-6-carboxylic acid, Method A

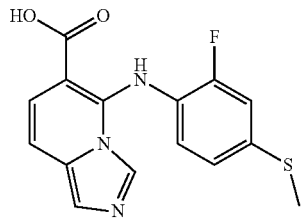 [SMILES: CSc1ccc(Nc2c(C(=O)O)ccc3cncn23)c(F)c1]

Step 1: 5-(2-Fluoro-4-methylsulfanyl-phenylamino)-imidazo[1,5-a]pyridine-6-carboxylic acid methyl ester

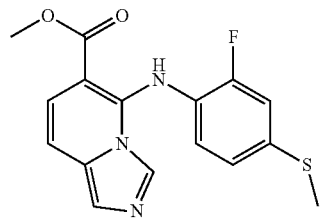

To a solution of 2-fluoro-4-methanesulfanyl phenyl amine (410 mg, 2.61 mmol) and 5-chloro-imidazo[1,5-a]pyridine-6-carboxylic acid methyl ester (500 mg, 2.37 mmol) in THF under nitrogen at −70° C. (20 mL) was added lithium bis(trimethylsilyl)amide (4.98 mL, 1M solution, 4.98 mmol) dropwise. After stirring for 30 minutes at −70° C. the reaction mixture was allowed to warm and then quenched with saturated aqueous ammonium chloride. The mixture was extracted with ethyl acetate (150 mL), the organic extract washed with brine, dried ($Na_2SO_4$), filtered and concentrated in vacuo. The resultant residue was subjected to flash chromatography (Si-PPC, gradient 0-50% ethyl acetate in cyclohexane) to yield the title compound (471 mg, 73%). LCMS (Method B): $R_T$=3.39 min, M+H$^+$=332.

Step 2: 5-(2-Fluoro-4-methansulfanyl-phenylamino)-imidazo[1,5-a]pyridine-6-carboxylic acid To a solution of 5-(2-fluoro-4-methanesulfanyl-phenylamino)-imidazo[1,5-a]pyridine-6-carboxylic acid methyl ester (471 mg, 1.45 mmol) in methanol (20 mL) was added aqueous sodium hydroxide (10 mL, 1M, 10 mmol) and the reaction mixture stirred at 70° C. for 30 minutes. The reaction mixture was concentrated in vacuo to ~20 mL volume and the resultant solution diluted with water (20 mL) before being acidified to pH ~1 by addition of aqueous hydrochloric acid (1M) causing a precipitate to form. The precipitate was collected by filtration and dried under vacuum at 45° C. to yield the title compound as a dark tan solid (413 mg, 87%). LCMS (Method B): $R_T$=2.98 min, $[M+H]^+$=312.

5-(2-Fluoro-4-methylsulfanyl-phenylamino)-imidazo[1,5-a]pyridine-6-carboxylic acid, Method B

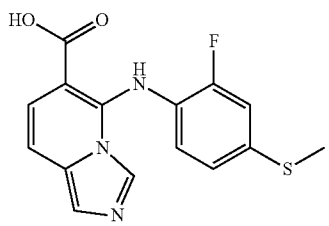 [SMILES: CSc1ccc(Nc2c(C(=O)O)ccc3cncn23)c(F)c1]

Step 1: Pyridine-2,5-dicarboxylic acid dimethyl ester

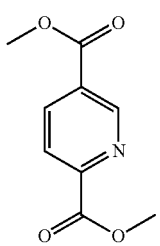

To a suspension of pyridine-2,5-dicarboxylic acid (20 g, 120 mmol) in dichloromethane (396 mL) and DMF (6.6 mL) was added oxalyl chloride (60.96 g, 480 mmol) dropwise over 20 minutes. After 16 hours at ambient temperature, the reaction mixture was concentrated in vacuo and the residue azeotroped with toluene. The residue was taken up in cold (0° C.) methanol (276 mL) and stirred for 15 minutes. The resultant solution was concentrated in vacuo and the residue taken up in ethyl acetate. The mixture was washed with a saturated aqueous solution of sodium bicarbonate, water and brine. A portion of the product was collected as a white precipitate. The organic phase was isolated, dried ($Na_2SO_4$), filtered and concentrated in vacuo to afford the title compound as a white solid (combined material obtained: 22.93 g, 98%). LCMS (method B): $R_T$=2.48 min, $[M+H]^+$=196.

Step 2: 1-Oxy-pyridine-2,5-dicarboxylic acid dimethyl ester

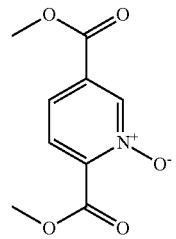

To a cold (0° C.) solution of pyridine-2,5-dicarboxylic acid dimethyl ester (22.93 g, 118 mmol) in dichloromethane (472 mL) was added 3-chloroperbenzoic acid (62.5 g, 278 mmol) portionwise. The reaction mixture was allowed to warm to ambient temperature. After stirring for 18 hours, the reaction mixture was concentrated in vacuo, and the resultant residue was adsorbed onto HMN and subjected to flash chromatography (Si-PPC, gradient 0% to 100%, ethyl acetate in hexane) to afford the title compound as a pale yellow oil (17.08 g, 69%). LCMS (method B): $R_T$=1.64 min, $[M+H]^+$=212.

Step 3: 6-Chloro-pyridine-2,5-dicarboxylic acid dimethyl ester

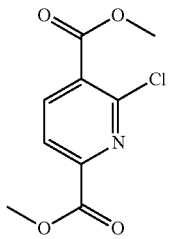

To a solution of 1-oxy-pyridine-2,5-dicarboxylic acid dimethyl ester (17.08 g, 81 mmol) in toluene (450 mL) was added phosphorous oxychloride (8.3 mL, 89 mmol). The reaction mixture was heated to 95° C. and stirred for 1.5 hours. The reaction was quenched by the addition of water and the mixture diluted with ethyl acetate. The solution was washed with a saturated aqueous solution of sodium bicarbonate, water and brine. The organic phase was isolated, dried ($Na_2SO_4$), filtered and concentrated in vacuo to afford the title compound as a pale yellow solid (11.97 g, 65%) which was used without purification in the next step. LCMS (method B): $R_T$=2.77 min, $[M+H]^+$=230.

Step 4: 2-Chloro-6-hydroxymethyl-nicotinic acid methyl ester

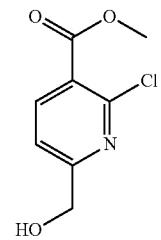

A cold (0° C.) suspension of calcium chloride (19.54 g, 176 mmol) and sodium borohydride (4.18 g, 110 mmol) in anhydrous ethanol (176 mL) and anhydrous THF (88 mL) was stirred for 1 hour, after which 6-chloro-pyridine-2,5-dicarboxylic acid dimethyl ester (9.97 g, 44 mmol) was added. After stirring at 0° C. for a further 6 hours, the reaction was quenched by the addition of $H_2SO_4$ (35 mL, 5M). The reaction mixture was diluted with ethyl acetate and filtered through Celite®. The filtrate was washed with 1M NaOH, water and brine, the organic phase was isolated, dried ($Na_2SO_4$), filtered and concentrated in vacuo. The resultant residue was subjected to flash chromatography (Si-PPC, gradient 0% to 100%, ethyl acetate in hexane) to afford the title compound as a yellow oil (6.14 g, 69%). LCMS (method B): $R_T$=2.34 min, $[M+H]^+$=202.

Step 5: 6-Azidomethyl-2-chloro-nicotinic acid methyl ester

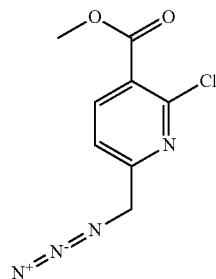

To a cold (0° C.) solution of 2-chloro-6-hydroxymethyl-nicotinic acid methyl ester (4.98 g, 24.8 mmol) in dichloromethane (161 mL) was added mesyl chloride (2.5 mL, 29.8 mmol). The reaction mixture was allowed to warm to room temperature and stirred for 30 minutes. The mixture was diluted with ethyl acetate and washed with a saturated aqueous solution of sodium bicarbonate, water and brine. The organic phase was isolated, dried ($Na_2SO_4$), filtered and concentrated in vacuo. The resultant residue was taken up in dimethylformamide (62 mL) and sodium azide (4.03 g, 62 mmol) added. After stirring at room temperature for 16 hours, the reaction mixture was cooled to 0° C., quenched with water (ca. 50 mL), and extracted three times with ethyl acetate. The combined organic extracts were washed with water and brine, dried ($Na_2SO_4$), filtered and concentrated in vacuo. The residue was subjected to flash chromatography (Si-PPC, gradient 0% to 50%, ethyl acetate in hexane) to afford the title compound as a pale yellow oil (4.76 g, 85%). LCMS (method B): $R_T$=3.22 min, $[M+H]^+$=227.

Step 6: 6-Aminomethyl-2-chloro-nicotinic acid methyl ester

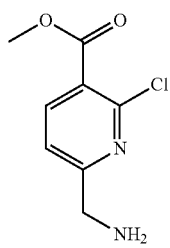

To a solution of 6-azidomethyl-2-chloro-nicotinic acid methyl ester (4.75 g, 21 mmol) in THF (189 mL) and water (3.6 mL) was added triphenylphosphine (11 g, 42 mmol), the reaction mixture was heated at 45° C. for 16 hours. The reaction mixture was concentrated under reduced pressure and the residue azeotroped with methanol. The resultant residue was subjected to flash chromatography (Si-PPC, gradient 0% to 10%, methanol in dichloromethane) to afford the title compound as a yellow solid. LCMS (method B): $R_T$=2.65 min, $[M+H]^+$=201.

Step 7: 2-Chloro-6-formylaminomethyl-nicotinic acid methyl ester

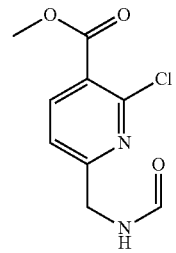

To a solution of 6-aminomethyl-2-chloro-nicotinic acid methyl ester (740 mg, 3.7 mmol) in formic acid (18.5 mL) was added acetic anhydride (3.7 mL). The reaction mixture was stirred at room temperature for 1.5 hours. The reaction mixture was concentrated in vacuo and azeotroped three times with toluene to afford the title compound as a yellow oil (757 mg, 90%) which was used without purification in the next step. LCMS (method B): $R_T$=2.20 min, $[M+H]^+$=229.

Step 8: 2-(2-Fluoro-4-methylsulfanyl-phenylamino)-6-formylaminomethyl-nicotinic acid methyl ester

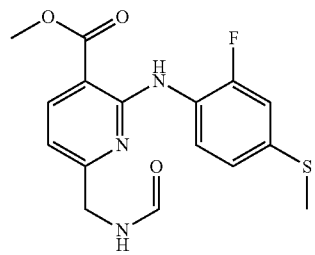

To a solution of 2-chloro-6-formylaminomethyl-nicotinic acid methyl ester (123 mg, 0.54 mmol) in toluene (1.6 mL) was added potassium phosphate (119 mg, 0.76 mmol), 2-fluoro-4-methylsulfanyl-phenylamine (102 mg, 0.65 mmol), tris(dibenzylideneacetone)dipalladium (12.8 mg, 0.014 mmol) and dicyclohexyl-(2',6'-diisopropoxy-biphenyl-2-yl)-phosphane (25 mg, 0.054 mmol). The reaction mixture was degassed with argon then heated at 100° C. After 25 hours, the reaction mixture was cooled, diluted with ethyl acetate and washed with a saturated aqueous solution of ammonium chloride, water then brine. The organic phase was isolated, dried ($Na_2SO_4$), filtered and concentrated in vacuo. The residue was triturated with ethyl acetate to afford the title compound as a bright yellow solid (43 mg, 23%). LCMS (method B): $R_T$=3.53 min, $[M+H]^+$=350.

Step 9: 5-(2-Fluoro-4-methylsulfanyl-phenylamino)-imidazo[1,5-a]pyridine-6-carboxylic acid methyl ester

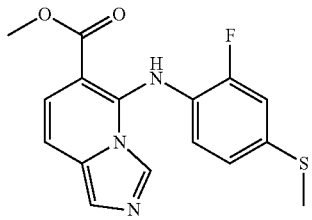

To a suspension of 2-(2-fluoro-4-methylsulfanyl-phenylamino)-6-formylaminomethyl-nicotinic acid methyl ester (309 mg, 0.89 mmol) in toluene (15.6 mL) was added phosphorous oxychloride (91 µl, 0.98 mmol) and the reaction mixture heated to 95° C. and stirred for 1 hour. The cooled reaction mixture was quenched by the addition of water (ca. 2 mL) then concentrated in vacuo. The resultant residue was taken up in ethyl acetate and washed with water followed by a saturated aqueous solution of sodium bicarbonate and brine. The organic phase was isolated, dried ($Na_2SO_4$), filtered, concentrated in vacuo, and the residue subjected to flash chromatography (Si-PPC, gradient 0% to 40%, ethyl acetate in hexane) to afford the title compound as a yellow solid (150 mg, 51%). LCMS (method B): $R_T$=3.44 min, $[M+H]^+$=332.

Step 10: 5-(2-Fluoro-4-methylsulfanyl-phenylamino)-imidazo[1,5-a]pyridine-6-carboxylic acid To a solution of 5-(2-fluoro-4-methylsulfanyl-phenylamino)-imidazo[1,5-a]pyridine-6-carboxylic acid methyl ester (150 mg, 0.45 mmol) in IMS (10 mL) was added sodium hydroxide (0.5 mL, 1M aqueous solution, 0.5 mmol), the reaction mixture heated at 65° C. for 1.5 hours. The reaction mixture was concentrated in vacuo then taken up in water (ca. 15 mL), the aqueous solution was washed with diethyl ether before the pH was adjusted to pH 3 using 1M HCl, resulting in precipitation of a brown solid. The precipitate was extracted using ethyl acetate, the organic phase was isolated and washed with water followed by brine, dried ($Na_2SO_4$), filtered and concentrated under reduced pressure to afford the title compound as a brown solid (109 mg, 76%). $^1$H NMR (CD$_3$OD): 7.67 (1 H, s), 7.44 (1 H, d, J=9.53 Hz), 7.39 (1 H, d, J=0.83 Hz), 7.24 (1 H, dd, J=9.57, 0.80 Hz), 7.15 (1 H, dd, J=11.47, 2.12 Hz), 7.02-7.01 (1 H, m), 6.76 (1 H, t, J=8.49 Hz), 2.49 (3 H, s).

5-Fluoro-2-(2-fluoro-4-trimethylsilanyl-phenylamino)-6-formylaminomethyl-nicotinic acid methyl ester

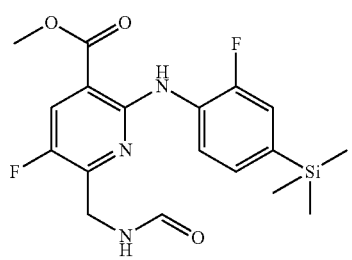

Step 1: 6-Chloro-5-fluoro-2-(2-fluoro-4-trimethylsilanyl-phenylamino)-nicotinic acid

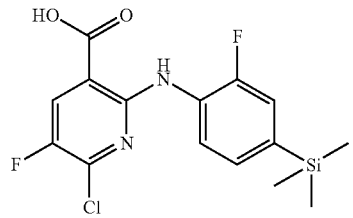 [SMILES: C[Si](C)(C)c1ccc(Nc2nc(Cl)c(F)cc2C(=O)O)c(F)c1]

To a cold (−78° C.) solution of 2-fluoro-4-trimethylsilanyl-phenylamine (19.2 g, 105 mmol) in anhydrous THF (50 mL) was added a solution of LHMDS (160 mL, 1 M in hexanes, 160 mmol) dropwise over 45 minutes under a nitrogen atmosphere. After 2 hours at −78° C., a solution of 2,6-dichloro-5-fluoro-nicotinic acid (10.5 g, 50 mmol) in anhydrous THF (30 mL) was added. The mixture was stirred at −78° C. for 1 hour then allowed to warm to ambient temperature. After 18 hours stirring at ambient temperature the reaction was quenched with water and adjusted to pH 2 by the addition of concentrated HCl. The solution was extracted with ethyl acetate and the organic layer was isolated, washed with water followed by brine, dried ($Na_2SO_4$), filtered and evaporated in vacuo. The resultant residue was triturated with methanol and filtered to afford the title compound as a yellow solid (8.7 g, 49%). LCMS (method B): $R_T$=4.92 min, $[M+H]^+$=357.

Step 2: 6-Chloro-5-fluoro-2-(2-fluoro-4-trimethylsilanyl-phenylamino)-nicotinic acid methyl ester

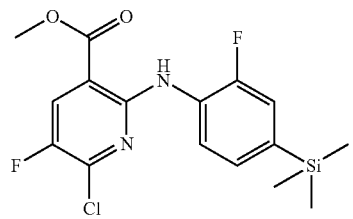 [SMILES: COC(=O)c1cc(F)c(Cl)nc1Nc1ccc([Si](C)(C)C)cc1F]

To a suspension of 6-chloro-5-fluoro-2-(2-fluoro-4-trimethylsilanyl-phenylamino)-nicotinic acid (7.6 g, 21.3 mmol) in dichloromethane (100 mL) and DMF (1 mL) was added oxalyl chloride (9.1 mL, 106.4 mmol) dropwise over 20 minutes. The reaction mixture was stirred at reflux for 18 hours and then concentrated in vacuo and the residue azeotroped with toluene. The resultant residue was taken up in cold (0° C.) methanol (100 mL). The resultant solution was heated at reflux for 1 hour, then cooled to room temperature and filtered. The precipitate was washed with cold methanol and dried under vacuum at 45° C. to give the title compound as a yellow solid (7.3 g, 92%). LCMS (method B): $R_T$=5.38 min, $[M+H]^+$=371.

Step 3: 6-Cyano-5-fluoro-2-(2-fluoro-4-trimethylsilanyl-phenylamino)-nicotinic acid methyl ester

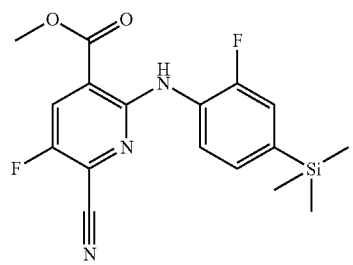 [SMILES: COC(=O)c1cc(F)c(C#N)nc1Nc1ccc([Si](C)(C)C)cc1F]

A degassed suspension of 6-chloro-5-fluoro-2-(2-fluoro-4-trimethylsilanyl-phenylamino)-nicotinic acid methyl ester (7.8 g, 21.2 mmol), zinc (II) cyanide (1.84 g, 15.6 mmol), and Pd(PPh$_3$)$_4$ (2.43 g, 2.12 mmol) in DMF (40 mL) was subjected to microwave irradiation at 150° C. for 15 minutes. The reaction mixture was filtered through Celite® and the filtrate diluted with ethyl acetate. The organic phase was washed twice with water and once with brine, dried (Na$_2$SO$_4$), filtered and concentrated in vacuo. The resultant residue was triturated with diethyl ether and pentane, and then dried under vacuum to afford the title compound as a yellow solid (6.9 g, 91%). LCMS (method B): R$_T$=4.99 min, [M+H]$^+$=362.

Step 4: 6-Aminomethyl-5-fluoro-2-(2-fluoro-4-trimethylsilanyl-phenylamino)-nicotinic acid methyl ester

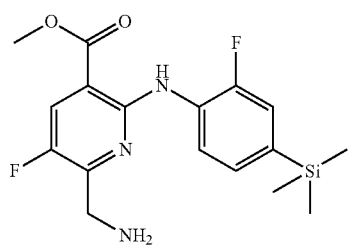 [SMILES: COC(=O)c1cc(F)c(CN)nc1Nc1ccc([Si](C)(C)C)cc1F]

To a suspension of 6-cyano-5-fluoro-2-(2-fluoro-4-trimethylsilanyl-phenylamino)-nicotinic acid methyl ester (5.7 g, 15.8 mmol) in methanol (130 mL) was added cobalt (II) chloride (7.5 g, 31.6 mmol). The reaction mixture was stirred for 10 minutes, then cooled to 0° C. and sodium borohydride (6.0 g, 158 mmol) was added in small portions over 30 minutes. The reaction mixture was stirred at 0° C. for 15 minutes and then at room temperature for 1 hour. The reaction was quenched by addition of concentrated hydrochloric acid (20 mL) and the mixture stirred for 15 minutes. The reaction mixture was filtered to remove a white solid, which was washed with dichloromethane, and the filtrate was concentrated under reduced pressure. The resultant residue was dissolved in ethyl acetate and washed with a saturated solution of sodium bicarbonate, followed by water then brine. The organic phase was isolated, dried (Na$_2$SO$_4$), filtered and concentrated in vacuo to afford the title compound as a brown solid (2.0 g, 34%). LCMS (method B): R$_T$=2.77 min, [M+H]$^+$=366.

Step 5: 5-Fluoro-2-(2-fluoro-4-trimethylsilanyl-phenylamino)-6-formylaminomethyl-nicotinic acid methyl ester To a solution of 6-aminomethyl-5-fluoro-2-(2-fluoro-4-trimethylsilanyl-phenylamino)-nicotinic acid methyl ester (2.0 g, 5.5 mmol) in formic acid (30 mL) at 0° C. was added acetic anhydride (6 mL). The reaction mixture was stirred at ambient temperature for 2 hours. The reaction mixture was concentrated in vacuo and the resultant residue azeotroped with toluene, then dissolved in dichloromethane. This organic layer was washed with a saturated aqueous solution of sodium bicarbonate, followed by brine, dried (Na$_2$SO$_4$), filtered and concentrated in vacuo to afford the title compound as a dark brown solid (2.1 g, 100%). LCMS (method B): R$_T$=4.36 min, [M+H]$^+$=394.

5-(4-Bromo-2-fluoro-phenylamino)-8-fluoro-imidazo[1,5-a]pyridine-6-carboxylic acid methyl ester

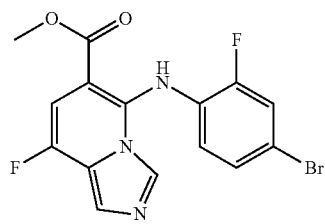 [SMILES: COC(=O)c1cc(F)c2cncn2c1Nc1ccc(Br)cc1F]

Step 1: 2-(4-Bromo-2-fluoro-phenylamino)-5-fluoro-6-formylaminomethyl-nicotinic acid methyl ester

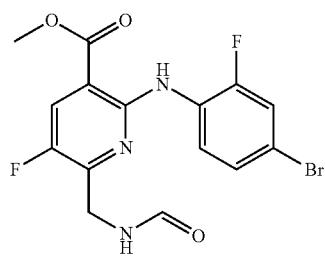 [SMILES: COC(=O)c1cc(F)c(CNC=O)nc1Nc1ccc(Br)cc1F]

To a solution of 5-fluoro-2-(2-fluoro-4-trimethylsilanyl-phenylamino)-6-formylaminomethyl-nicotinic acid methyl ester (2.6 g, 6.6 mmol) in dichloromethane (65 mL) at −30° C. was added NBS (1.2 g, 6.6 mmol). The reaction mixture was stirred at −30° C. for 1.5 hours, and then concentrated under reduced pressure The resultant residue was taken up in ethyl acetate and this organic solution was washed with a saturated aqueous solution of sodium bicarbonate, followed by brine, dried (Na$_2$SO$_4$), filtered and evaporated in vacuo to afford the title compound as a brown solid (2.49 g, 95%). LCMS (method B): R$_T$=3.79 min, [M+H]$^+$=400/402.

Step 2: 5-(4-Bromo-2-fluoro-phenylamino)-8-fluoro-imidazo[1,5-a]pyridine-6-carboxylic acid methyl ester To a suspension of 2-(4-bromo-2-fluoro-phenylamino)-5-fluoro-6-formylaminomethyl-nicotinic acid methyl ester (2.49 g, 6.2 mmol) in toluene (60 mL) was added phosphorous oxychloride (0.65 mL, 7.0 mmol). The reaction mixture was heated to 90° C. and stirred for 1.5 hour before cooling to room temperature and concentrating in vacuo. The resultant residue was dissolved in ethyl acetate and washed with water followed by a saturated aqueous solution of sodium bicarbonate and then brine. The organic phase was isolated, dried (MgSO$_4$), filtered and concentrated in vacuo. The resultant residue was subjected to flash chromatography (Si-PPC, gradient 0% to 100%, ether in hexane) to afford the title compound as a yellow solid (692 mg, 29%). LCMS (method B): R$_T$=3.97 min, [M+H]$^+$=382/384.

8-Fluoro-5-(2-fluoro-4-iodo-phenylamino)-imidazo[1,5-a]pyridine-6-carboxylic acid

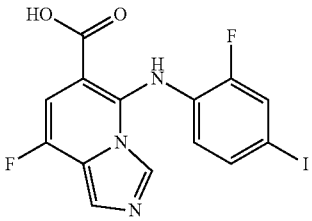 [SMILES: O=C(O)c1cc(F)c2cncn2c1Nc1ccc(I)cc1F]

Step 1: 5-Fluoro-2-(2-fluoro-4-iodo-phenylamino)-6-formylaminomethyl-nicotinic acid methyl ester

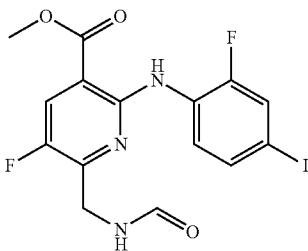 [SMILES: COC(=O)c1cc(F)c(CNC=O)nc1Nc1ccc(I)cc1F]

To a solution of 5-fluoro-2-(2-fluoro-4-trimethylsilanyl-phenylamino)-6-formylaminomethyl-nicotinic acid methyl ester (2.4 g, 6.1 mmol) in dichloromethane (15 mL) at 0° C. was added ICl (2.0 g, 12.2 mmol). The mixture was stirred at 0° C. for 0.5 hour, then quenched with water, washed with a saturated solution of sodium sulphite followed by brine, dried (Na$_2$SO$_4$), filtered and evaporated in vacuo to afford the title compound as a brown solid (2.7 g, 98%). LCMS (method B): R$_T$=3.81 min, [M+H]$^+$=448.

Step 2: 8-Fluoro-5-(2-fluoro-4-iodo-phenylamino)-imidazo[1,5-a]pyridine-6-carboxylic acid methyl ester

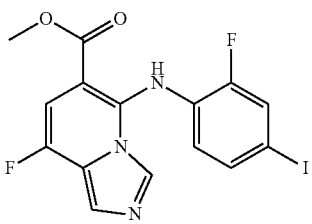 [SMILES: COC(=O)c1cc(F)c2cncn2c1Nc1ccc(I)cc1F]

To a suspension of 5-fluoro-2-(2-fluoro-4-iodo-phenylamino)-6-formylaminomethyl-nicotinic acid methyl ester (2.7 g, 6.2 mmol) in toluene (20 mL) was added phosphorous oxychloride (1.1 mL, 12.2 mmol). The reaction mixture was heated at 95° C. for 30 minutes. The reaction mixture was cooled to room temperature and then concentrated in vacuo. The resultant residue was dissolved in ethyl acetate and washed with water followed by a saturated aqueous solution of sodium bicarbonate, then brine. The organic phase was isolated, dried (MgSO$_4$), filtered and concentrated in vacuo. The resultant residue was subjected to flash chromatography (Si-PPC, gradient 0% to 50%, ethyl acetate in hexane) to afford the title compound as a yellow solid (1.0 g, 39%). LCMS (method B): R$_T$=3.97 min, [M+H]$^+$=430.

Step 3: 8-Fluoro-5-(2-fluoro-4-iodo-phenylamino)-imidazo[1,5-a]pyridine-6-carboxylic acid To a solution of 8-fluoro-5-(2-fluoro-4-iodo-phenylamino)-imidazo[1,5-a]pyridine-6-carboxylic acid methyl ester (500 mg, 1.17 mmol) in IMS (10 mL) was added sodium hydroxide (1.75 mL, 1M aqueous solution, 1.75 mmol), the reaction mixture heated at 65° C. for 45 min. The reaction mixture was concentrated in vacuo and the residue taken up in water. 1N HCl was added to adjust to pH 1. The precipitate formed was filtered off and dried in vacuo to give the title compound (435 mg, 90%). LCMS (method B): R$_T$=3.47 min, [M+H]$^+$=416.

Synthesis of Azaimidazo[1,5-a]Pyridines 5-(2-Fluoro-4-iodo-phenylamino)-imidazo[1,5-a]pyrazine-6-carboxylic acid methyl ester

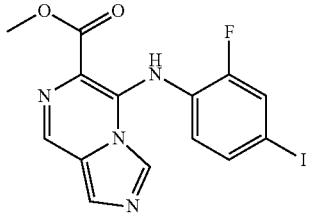 [SMILES: COC(=O)c1ncc2cncn2c1Nc1ccc(I)cc1F]

Step 1: 3,5-Dichloro-pyrazine-2-carboxylic acid

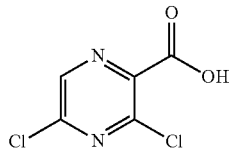 [SMILES: O=C(O)c1ncc(Cl)nc1Cl]

To a solution of diisopropylamine (13.0 mL, 92.6 mmol, 2.3 eq.) in anhydrous THF (300 mL) at −78° C. under N$_2$ was added dropwise a solution of 1.6 M nBuLi in hexanes (57.9 mL, 92.6 mmol, 2.3 eq.). After 1 hour a solution of 2,6-dichloropyrazine in anhydrous THF (6.0 g, 40.3 mmol) was added dropwise over 30 minutes. After stirring at −78° C. for 1 hour, the reaction mixture was poured onto crushed dry ice (solid carbon dioxide), and the reaction mixture was stirred at ambient temperature for 16 hours. The mixture was then diluted with water (100 mL) and washed with ethyl acetate (3×100 mL). The aqueous layer was cooled to 0° C., acidified with 2N HCl until pH ~2, and extracted with ethyl acetate (3×100 mL). The combined organic extracts were dried (Na$_2$SO$_4$), filtered and evaporated in vacuo. The resultant crude was purified by column chromatography (Si-PPC, gradient 0% to 50%, methanol in dichloromethane) to give the desired product as a beige solid (3.16 g, 40.6%). ¹H NMR (CDCl₃, 400 MHz) δ ppm 8.60 (s, 1H).

Step 2: 5-Chloro-3-(2-fluoro-4-trimethylsilanyl-phenylamino)-pyrazine-2-carboxylic acid

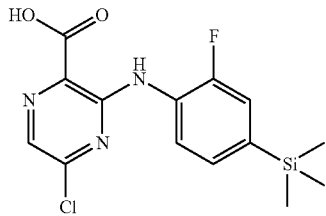 [SMILES: C[Si](C)(C)c1ccc(Nc2nc(Cl)cnc2C(=O)O)c(F)c1]

To a solution of 2-fluoro-4-trimethylsilanyl-phenylamine (3.8 g, 20.7 mmol, 2.0 eq) in anhydrous THF (150 mL) at −78° C. under N₂ was added dropwise a solution of 1.0 M LHMDS in THF (33.2 mL, 30 mmol, 3.2 eq) over 20 minutes. After 1 hour at −78° C., a solution of 3,5-dichloro-pyrazine-2-carboxylic acid (2.0 g, 10.3 mmol) in anhydrous THF (30 mL) was added. The mixture was stirred at −78° C. for 30 minutes, and then stirred at ambient temperature for 18 hours. The mixture was quenched with water and the pH adjusted to pH 2 by the addition of 2 N HCl. The reaction mixture was extracted with ethyl acetate, and the organic layer washed with water and brine, then dried (Na₂SO₄), filtered and evaporated in vacuo. The resultant residue was purified by column chromatography (Si-PPC, gradient 20 to 50% ethyl acetate in hexane, followed by 0% to 30%, methanol in dichloromethane) to give the desired compound as a yellow solid (2.95 g, 83.8%). ¹H NMR (CDCl₃, 400 MHz) δ ppm 10.41 (s, 1H), 8.28 (t, J=7.79 Hz, 1H), 7.93 (s, 1H), 7.40-7.23 (m, 2H), 0.27 (s, 9H).

Step. 3: 5-Chloro-3-(2-fluoro-4-trimethylsilanyl-phenylamino)-pyrazine-2-carboxylic acid methyl ester

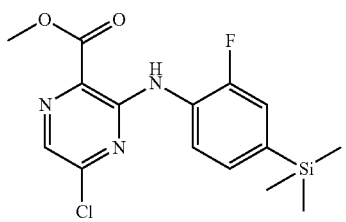

To a solution of 5-chloro-3-(2-fluoro-4-trimethylsilanyl-phenylamino)-pyrazine-2-carboxylic acid (2.95 g, 8.68 mmol) in methanol (50 mL) and toluene (100 mL) at 0° C. under N₂ was added a solution of 2M trimethylsilyldiazomethane in hexanes (9.55 mL, 19.0 mmol, 2.2 eq.), and the reaction mixture was stirred at ambient temperature for 30 minutes. The reaction mixture was diluted with ethyl acetate. The organic layer was washed with a saturated aqueous solution of sodium bicarbonate, water and brine, then dried (Na₂SO₄), filtered and evaporated in vacuo. The resultant residue was purified by column chromatography (Si-PPC, gradient 0 to 50% ethyl acetate in hexane) to give the desired compound as a yellow solid (2.18 g, 71.1%). ¹H NMR (CDCl₃, 400 MHz) δ ppm 10.54 (s, 1H), 8.36 (t, J=7.86 Hz, 1H), 8.06 (s, 1H), 7.34-7.26 (m, 2H), 4.05 (s, 3H), 0.28 (s, 9H); LCMS (method D1) R$_T$=1.38 min, [M+H]⁺=354.

Step 4: 5-Cyano-3-(2-fluoro-4-trimethylsilanyl-phenylamino)-pyrazine-2-carboxylic acid methyl ester

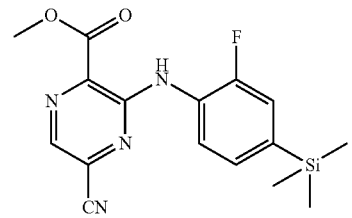

A degassed suspension of 5-chloro-3-(2-fluoro-4-trimethylsilanyl-phenylamino)-pyrazine-2-carboxylic acid methyl ester (1.35 g, 3.82 mmol), zinc (II) cyanide (492.8 mg, 4.2 mmol, 1.1 eq.), and Pd(PPh₃)₄ (551.0 mg, 0.48 mmol, 0.12 eq.) in anhydrous dimethylformamide (30 mL) was subjected to microwave irradiation at 150° C. for 18 minutes. The reaction mixture was poured into ethyl acetate and then filtered through a pad of Celite®. The pad was rinsed well with ethyl acetate (2×). The combined filtrates were washed with 50% brine (2×) and brine (1×), dried (Na₂SO₄), filtered and concentrated in vacuo. The crude residue was purified by column chromatography (Si-PPC, gradient 0 to 30% ethyl acetate in hexane) to give a brown oil. Trituration with MeOH afforded the desired compound as an orange solid (1.31 g, 99.8%). ¹H NMR (CDCl₃, 400 MHz) δ ppm 10.56 (s, 1H), 8.36 (s, 1H), 8.29 (t, J=7.82 Hz, 1H), 7.37-7.27 (m, 2H), 4.10 (s, 3H), 0.29 (s, 9H); LCMS (method D1): R$_T$=1.28 min, [M+H]⁺=345.

Step 5: 5-Aminomethyl-3-(2-fluoro-4-trimethylsilanyl-phenylamino)-pyrazine-2-carboxylic acid methyl ester

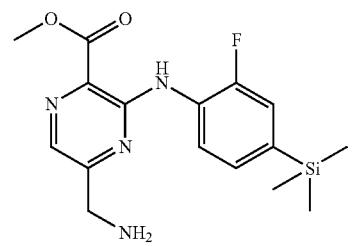

To a solution of 5-cyano-3-(2-fluoro-4-trimethylsilanyl-phenylamino)-pyrazine-2-carboxylic acid methyl ester (600 mg, 1.74 mmol) in concentrated glacial acetic acid (12 mL) was added 10% Pd on carbon (120 mg). The reaction mixture was evacuated with vacuum and purged with H₂ (3×), then stirred under an atmosphere of H₂ for 3.5 hours. The reaction mixture was then filtered through a pad of Celite®. The filtrate was concentrated in vacuo to give the desired product as the HOAc salt. LCMS (method C): R$_T$=2.51 min, [M+H]⁺=349.

Step 6: 3-(2-Fluoro-4-trimethylsilanyl-phenylamino)-5-formylaminomethyl-pyrazine-2-carboxylic acid methyl ester

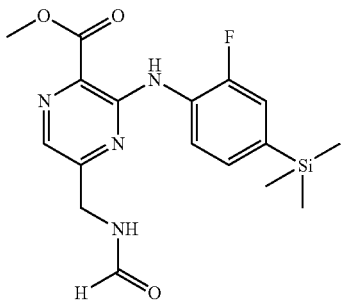

A solution of 5-aminomethyl-3-(2-fluoro-4-trimethylsilanyl-phenylamino)-pyrazine-2-carboxylic acid methyl ester (800 mg, 2.30 mmol) from above in formic acid (12 mL) and acetic anhydride (4 mL) was stirred at ambient temperature under $N_2$ for 1.5 hour. The reaction mixture was concentrated in vacuo, and the residue was azeotroped with toluene. The resultant residue was diluted with ethyl acetate. The organic layer was washed with saturated aqueous solution of sodium bicarbonate, water and brine, dried ($Na_2SO_4$), filtered and concentrated in vacuo to afford the title compound as a yellow foam (850 mg, 98.3%). LCMS (method D1): $R_T$=1.09 min, [M+H]$^+$=377.

Step 7: 3-(2-Fluoro-4-iodo-phenylamino)-5-formylaminomethyl-pyrazine-2-carboxylic acid methyl ester

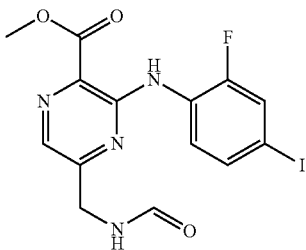 [SMILES: COC(=O)c1ncc(CNC=O)nc1Nc1ccc(I)cc1F]

To a cold (0° C.) solution of 3-(2-fluoro-4-trimethylsilanyl-phenylamino)-5-formylaminomethyl-pyrazine-2-carboxylic acid methyl ester (480 mg, 1.28 mmol) in dichloromethane (13 mL) under $N_2$ was added dropwise a solution of 1M iodine monochloride in dichloromethane (3.0 mL, 3.0 mmol, 2.4 eq), and the mixture was stirred at 0° C. for 1.5 hour. The reaction was quenched by addition of a saturated aqueous solution of sodium thiosulfate (3 mL). After stirring for 10 minutes the reaction mixture was poured into ethyl acetate. The organic layer was washed with a saturated aqueous solution of sodium bicarbonate, water and brine, dried ($Na_2SO_4$), filtered and evaporated in vacuo to afford the desired product as a yellow solid (548 mg, 99%). LCMS (method C): $R_T$=2.65 min, [M+H]$^+$=431.

Step 8: 5-(2-Fluoro-4-iodo-phenylamino)-imidazo[1,5-a]pyrazine-6-carboxylic acid methyl ester To a suspension of 3-(2-fluoro-4-iodo-phenylamino)-5-formylaminomethyl-pyrazine-2-carboxylic acid methyl ester (480 mg, 1.12 mmol) in toluene (18 mL) was added phosphorous oxychloride (0.42 mL, 4.4 mmol, 4.0 eq.), and the reaction mixture was heated at 95° C. for 1 hour. The reaction mixture was cooled to RT and then quenched with a saturated aqueous solution of sodium bicarbonate (2 mL). The resultant residue was dissolved in ethyl acetate and washed with water and brine. The organic phase was isolated, dried ($Na_2SO_4$), filtered and concentrated in vacuo. The resultant residue was subjected to flash chromatography (Si-PPC, gradient 0% to 20%, methanol in ethyl acetate) to give a yellow oil. Crystallization from dichloromethane ether hexane afforded the desired product as a yellow solid (190 mg, 41.3%). LCMS (method C): $R_T$=2.45 min, [M+H]$^+$=413.

5-(4-Bromo-2-fluoro-phenylamino)-imidazol[1,5-a]pyrazine-6-carboxylic acid methyl ester

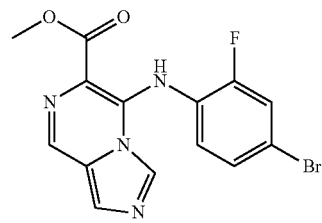 [SMILES: COC(=O)c1ncc2cncn2c1Nc1ccc(Br)cc1F]

Step 1: 3-(4-Bromo-2-fluoro-phenylamino)-5-formylaminomethyl-pyrazine-2-carboxylic acid methyl ester

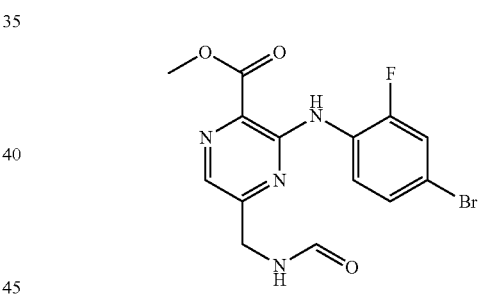

To a −30° C. solution of 3-(2-fluoro-4-trimethylsilanyl-phenylamino)-5-formylaminomethyl-pyrazine-2-carboxylic acid methyl ester (1.84 g, 4.89 mmol) in dichloromethane (50 mL) under $N_2$ was added NBS (0.96 g, 5.38 mmol, 1.1 eq.), and the reaction mixture was stirred at −30° C. for 3 h. More NBS (0.96 g, 5.38 mmol, 1.1 eq.) was added, and the reaction mixture was allowed to stand at 0° C. for 18 h. The reaction mixture was diluted with ethyl acetate (250 mL). The organic layer was washed with saturated aqueous solution of sodium bicarbonate, water and brine, dried ($Na_2SO_4$), filtered and concentrated in vacuo. The crude material was triturated with methanol to afford the desired product as a yellow solid (1.50 g, 80.1%). LCMS (method C): $R_T$=2.51 min, [M+H]$^+$=383/384.

Step 2: 5-(4-Bromo-2-fluoro-phenylamino)-imidazo[1,5-a]pyrazine-6-carboxylic acid methyl ester To a suspension of 3-(4-bromo-2-fluoro-phenylamino)-5-formylamino-methyl-pyrazine-2-carboxylic acid methyl ester (1.40 g, 3.65 mmol) in toluene (100 mL) was added phosphorous oxychloride (1.50 mL, 16.1 mmol, 4.4 eq.), and the reaction mixture was heated at 95° C. under N₂ for 1 hour. The reaction mixture was cooled to RT and then quenched with saturated aqueous solution of sodium bicarbonate (20 mL). The resultant residue was dissolved in ethyl acetate and washed with water and brine. The organic phase was isolated, dried (Na₂SO₄), filtered and concentrated in vacuo. The resultant residue was subjected to flash chromatography (Si-PPC, gradient 70 to 100% ethyl acetate in hexane, followed by 0% to 2% methanol in ethyl acetate) to give an orange oil. Crystallization from ethyl acetate hexane afforded the desired product as an orange solid (1.26 g, 94.3%). LCMS (method D1): $R_T$=0.86 min, [M+H]⁺=366/367.

5-(2-Fluoro-4-iodophenylamino)imidazo[1,5-a]pyrazine-6-carboxamide

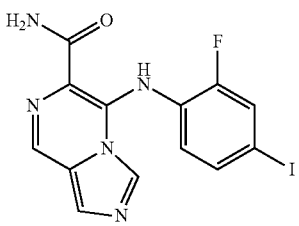 [SMILES: NC(=O)c1ncc2cncn2c1Nc1ccc(I)cc1F]

To a solution of 5-(2-fluoro-4-iodo-phenylamino)-imidazo[1,5-a]pyrazine-6-carboxylic acid (64.0 mg, 0.16 mmol) in anhydrous THF (3.6 mL) was added HOBt (56.5 mg, 0.42 mmol, 2.6 eq), DIPEA (0.073 mL, 0.42 mmol, 2.6 mmol), and EDCI (67.8 mg, 0.35 mmol, 2.2 eq), and the reaction mixture was stirred at room temperature under N₂ for 2 h. Concentrated aqueous ammonium hydroxide solution (0.50 mL) was added and the reaction mixture was stirred at room temperature for 20 h. The reaction mixture was diluted with ethyl acetate (50 mL) and washed with a saturated aqueous solution of ammonium chloride, water and brine. The organic layer was isolated and dried (Na₂SO₄), filtered, and concentrated in vacuo. The resultant residue was subjected to flash chromatography (Si-PPC, gradient 0 to 20% methanol in dichloromethane) to give an oil. Crystallization from DCM ether hexane afforded the title compound as a beige solid (9.9 mg, 16.0%). ¹H NMR (MeOD, 400 MHz) δppm 8.74 (s, 1H), 7.86 (s, 1H), 7.79 (s, 1H), 7.62 (dd, J=10.4 Hz, 2.0 Hz, 1H), 7.48 (d, J=8.4 Hz, 1H), 6.59 (t, J=8.4 Hz, 1H); LCMS (method D1): $R_T$=0.84 min, [M+H]⁺=398.

Example 5

5-(2-Fluoro-4-iodophenylamino)-imidazo[1,5-a]pyridine-6-carboxylic acid (2-hydroxyethoxy)-amide

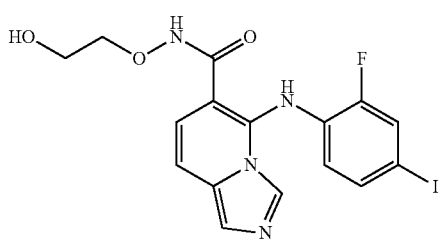 [SMILES: O=C(NOCCO)c1ccc2cncn2c1Nc1ccc(I)cc1F]

Step 1, Method A: 5-(2-Fluoro-4-iodophenylamino)-imidazo[1,5-a]pyridine-6-carboxylic acid (2-vinyloxyethoxy)-amide

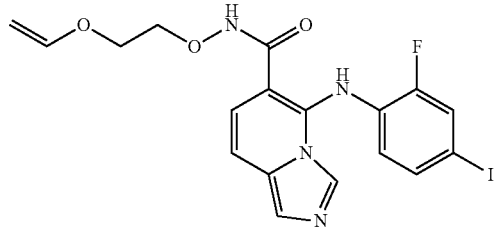 [SMILES: C=COCCONC(=O)c1ccc2cncn2c1Nc1ccc(I)cc1F]

To a solution of 5-(2-fluoro-4-iodophenylamino)-imidazo[1,5-a]pyridine-6-carboxylic acid (2.10 g, 5.29 mmol) and O-(2-vinyloxyethyl)-hydroxylamine (0.87 g, 8.46 mmol) in DMF (30 mL) was added EDCI hydrochloride (1.31 g, 6.90 mmol), HOBt (0.93 g, 6.90 mmol) and DIPEA (1.17 mL, 6.90 mmol). The reaction mixture was stirred at room temperature for 5 hours before being concentrated in vacuo. The resultant residue was dissolved in 1:1 tert-butylmethylether:ethyl acetate (20 mL) and aqueous saturated sodium hydrogen carbonate solution (20 mL) was added. The resultant mixture was sonicated until a precipitate formed, the precipitate was collected by filtration and dried in vacuo at 45° C. to yield the title compound as a tan solid (1.55 g, 60%). LCMS (Method B): $R_T$=2.80 min, M+H⁺=483.

Step 1, Method B: 5-(2-Fluoro-4-iodophenylamino)-imidazo[1,5-a]pyridine-6-carboxylic acid (2-vinyloxyethoxy)-amide To a solution of 5-(2-fluoro-4-iodophenylamino)imidazo[1,5-a]pyridine-6-carboxylic acid methyl ester (1.5 g, 3.64 mmol) and O-(2-vinyloxyethyl)hydroxylamine (749 mg, 7.28 mmol) in THF (30 mL) at 0° C. was added lithium bis(trimethylsilyl)amide as a solution in THF (18 mL, 1M, 18 mmol) over 5 minutes. The reaction mixture was stirred at -0° C. for 1 hour before being quenched with saturated aqueous ammonium chloride. Volatile solvents were removed in vacuo and then diethyl ether (10 mL) and ethyl acetate (20 mL) added. The resultant mixture was sonicated causing a precipitate to form which was filtered off to give the title compound as a yellow solid (1.07 g, 61%). LCMS (Method B): $R_T$=2.79 min, M+H⁺=483.

Step 1, Method C: 5-(2-Fluoro-4-iodophenylamino)-imidazo[1,5-a]pyridine-6-carboxylic acid (2-vinyloxyethoxy)-amide To a mechanically stirred solution of 5-(2-fluoro-4-iodophenylamino)imidazo[1,5-a]pyridine-6-carboxylic acid methyl ester (82.17 g, 0.2 mol) and O-(2-vinyloxyethyl)hydroxylamine (40.73 g, 0.382 mol) in dry THF (1.27 L) at 5° C. under N₂ atmosphere, was added lithium bis(trimethylsilyl) amide as a solution in THF (1 L, 1 M, 1 mol) over 1 hr, maintaining the temperature below 10° C. The reaction mixture was stirred at 0-5° C. for 20 minutes before being quenched with addition water (200 ml) and saturated saline (350 mL). Volatile solvents were removed in vacuo and the residue diluted with water (1.5 L) and extracted 2-methyl tetrahydrofuran (3×1 L). The organic layers were washed water (500 mL), saturated saline (500 mL), dried (Na₂CO₃) and absorbed onto silica gel (200 g) and purified on silica gel (400 g) using ethyl acetate as eluent. The resultant crude product was triturated with tert-butyl methyl ether (400 mL) to yield the title compound as a brown solid (58.36 g, 60%). LCMS (Method B): $R_T$=2.79 min, [M+H]⁺=483.

Step 2, Method A: 5-(2-fluoro-4-iodophenylamino)-imidazo[1,5-a]pyridine-6-carboxylic acid (2-hydroxyethoxy)-amide To a suspension of 5-(2-fluoro-4-iodophenylamino)-imidazo[1,5-a]pyridine-6-carboxylic acid (2-vinyloxyethoxy)-amide (2.87 g, 5.95 mmol) in methanol (45 mL) was added aqueous hydrochloric acid (11.9 mL, 1M, 11.9 mmol). The reaction mixture was stirred at room temperature for 45 minutes during which time the solids dissolved. The reaction mixture was concentrated in vacuo to remove the methanol. The resultant solution was diluted with 1:1 tert-butylmethylether:ethyl acetate (20 mL) and aqueous saturated sodium hydrogen carbonate solution (20 mL) added. The resultant mixture was sonicated until a precipitate formed and the precipitate was collected by filtration and dried in vacuo at 45° C. to yield the title compound as a yellow solid (2.5 g, 92%). LCMS (Method A): $R_T$=5.58 min, M+H$^+$=457. $^1$H NMR (DMSO-d$_6$, 400 MHz) 8.05 (1 H, s), 7.58 (1 H, dd, J=10.69, 1.92 Hz), 7.43 (1 H, s), 7.39 (1 H, d, J=9.33 Hz), 7.31-7.28 (1 H, m), 6.89 (1 H, d, J=9.31 Hz), 6.34 (1 H, t, J=8.68 Hz), 4.64 (1 H, s), 3.64 (2 H, t, J=4.78 Hz), 3.46 (2 H, m).

Step 2, Method B: 5-(2-Fluoro-4-iodophenylamino)-imidazo[1,5-a]pyridine-6-carboxylic acid (2-hydroxyethoxy)-amide To a suspension of 5-(2-fluoro-4-iodophenylamino)-imidazo[1,5-a]pyridine-6-carboxylic acid (2-vinyloxyethoxy)-amide (58.36 g, 0.12 mol) in methanol (600 mL) was added aqueous hydrochloric acid (242 mL, 1M, 0.242 mol). The reaction mixture was stirred and warmed to 45° C. for 1 hr during which time the solids dissolved. The reaction mixture was then cooled to room temperature, and concentrated in vacuo to remove the methanol. The resultant residue was treated with aqueous saturated sodium hydrogen carbonate and stirred at room temperature for 1 hr before collecting crude product by filtration, and drying at 55° C. over phosphorus (V) oxide under vacuum for 24 hr. The crude product was crystallized from IPA:H$_2$O (1:1, v/v) (800 mL) with slow cooling and mechanical stirring. The product was collected by filtration and washed cold IPA:H$_2$O (1:1, v/v) (100 mL) before being dried in vacuo at 55° C. to yield the title compound as a light brown solid (50.2 g, 90%). LCMS (Method A): $R_T$=5.58 min, [M+H]$^+$=457. $^1$H NMR (DMSO-d$_6$, 400 MHz) 8.05 (1 H, s), 7.58 (1 H, dd, J=10.69, 1.92 Hz), 7.43 (1 H, s), 7.39 (1 H, d, J=9.33 Hz), 7.31-7.28 (1 H, m), 6.89 (1 H, d, J=9.31 Hz), 6.34 (1 H, t, J=8.68 Hz), 4.64 (1 H, s), 3.64 (2 H, t, J=4.78 Hz), 3.46 (2 H, m).

Example 6

5-(2-Fluoro-4-iodo-phenylamino)-imidazo[1,5-a]pyridine-6-carboxylic acid ((R)-2,3-dihydroxy-propoxy)-amide

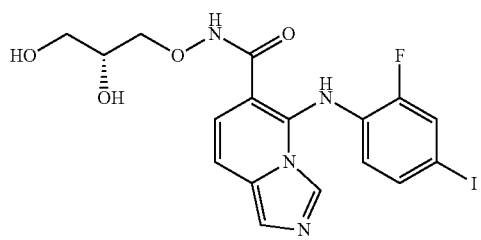 [SMILES: O=C(NOC[C@H](O)CO)c1ccc2cncn2c1Nc1ccc(I)cc1F]

Step 1: 5-(2-Fluoro-4-iodo-phenylamino)-imidazo[1,5-a]pyridine-6-carboxylic acid ((S)-2,2-dimethyl-[1,3]dioxolan-4-ylmethoxy)-amide

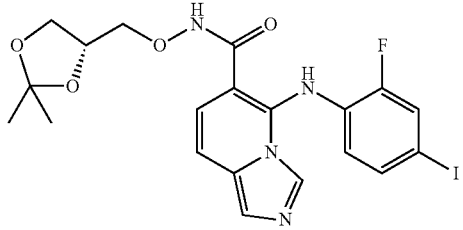 [SMILES: CC1(C)OC[C@H](CONC(=O)c2ccc3cncn3c2Nc2ccc(I)cc2F)O1]

To a solution of 5-(2-fluoro-4-iodo-phenylamino)-imidazo[1,5-a]pyridine-6-carboxylic acid (326 mg, 0.82 mmol) in THF (4.1 ml) was added O—((R)-2,2-dimethyl-[1,3]dioxolan-4-ylmethyl)-hydroxylamine (362 mg, 2.46 mmol), DIPEA (1.26 ml, 7.4 mmol), HOBt (327 mg, 2.46 mmol) and EDCI (471 mg, 2.46 mmol), the mixture stirred for 18 hours at ambient temperature. The reaction mixture was diluted with ethyl acetate and washed with a saturated aqueous solution of sodium bicarbonate followed by water and then brine. The organic phase was isolated, dried (Na$_2$SO$_4$), filtered and concentrated in vacuo. Purification of the resultant residue by flash chromatography (Si-PPC, gradient 0% to 10%, methanol in dichloromethane) afforded the title compound as a pale yellow solid (364 mg, 84%). LCMS (method B): $R_T$=2.58 min, [M+H]$^+$=527.

Step 2: 5-(2-Fluoro-4-iodo-phenylamino)-imidazo[1,5-a]pyridine-6-carboxylic acid ((R)-2,3-dihydroxypropoxy)-amide A solution of 5-(2-fluoro-4-iodo-phenylamino)-imidazo[1,5-a]pyridine-6-carboxylic acid ((S)-2,2-dimethyl-[1,3]dioxolan-4-ylmethoxy)-amide (364 mg, 0.7 mmol) in methanol (0.5 ml) and dichloromethane (0.5 ml) was loaded onto an SCX-2 cartridge. The cartridge was flushed with methanol and the desired product was eluted using a 2M solution of ammonia in methanol. The appropriate fractions were combined and concentrated under reduced pressure and the residue was azeotroped with dichloromethane. Purification of the resultant residue by flash chromatography (Si-PPC, gradient 0% to 10%, methanol in dichloromethane) followed by preparative HPLC (Gemini 5 micron C$_6$-Phenyl 250×21.20 mm column, 20 mmol Et$_3$N per litre solvent, gradient acetonitrile/water, 5 to 98%, ramp time 25 minutes) afforded the title compound as a yellow solid (77.6 mg, 23%). LCMS (method A): $R_T$=5.13 min, [M+H]$^+$=487. $^1$H NMR (DMSO-d$_6$): 8.01 (1 H, s), 7.58 (1 H, dd, J=10.68, 1.92 Hz), 7.42 (1 H, s), 7.38 (1 H, d, J=9.34 Hz), 7.30 (1 H, dd, J=8.43, 1.82 Hz), 6.91 (1H, d, J=9.32 Hz), 6.32 (1 H, t, J=8.68 Hz), 3.72-3.67 (1 H, m), 3.60-3.51 (2 H, m), 3.30 (2H, d, J=4.94 Hz).

Example 7

5-(2-fluoro-4-iodo-phenylamino)-imidazo[1,5-a]pyridine-6-carboxylic acid ((S)-2-hydroxy-propoxy)-amide

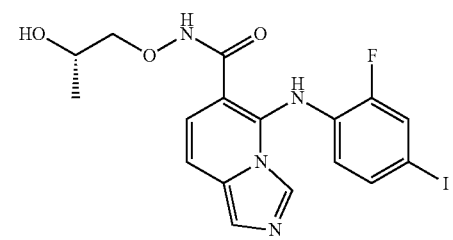 [SMILES: C[C@H](O)CONC(=O)c1ccc2cncn2c1Nc1ccc(I)cc1F]

To a solution of 5-(2-fluoro-4-iodo-phenylamino)-imidazo[1,5-a]pyridine-6-carboxylic acid (130 mg, 0.33 mmol) in THF (1.7 mL) was added (S)-1-aminooxy-propan-2-ol hydrochloride (84 mg, 0.66 mmol), DIPEA (0.23 mL, 1.32 mmol), HOBt (88 mg, 0.66 mmol) and EDCI (126 mg, 0.66 mmol). After 18 hours stirring at ambient temperature, further (S)-1-aminooxy-propan-2-ol hydrochloride (84 mg, 0.66 mmol), DIPEA (0.23 mL, 1.32 mmol), HOBt (88 mg, 0.66 mmol) and EDCI (126 mg, 0.66 mmol) and THF (1.7 mL) were added. The reaction mixture was stirred at ambient temperature for a further 5 hours. The reaction mixture was loaded onto an Isolute SCX-2 cartridge. The cartridge was then washed with methanol and the desired compound was eluted using a 2M solution of ammonia in methanol. Appropriate fractions were combined and concentrated under reduced pressure and the residue azeotroped with dichloromethane. The resultant residue was subjected to flash chromatography (Si-PPC, gradient 0 to 10%, methanol in dichloromethane) to afford the title compound as a yellow solid (17 mg, 11%). LCMS (method A): $R_T$=6.01 min, $[M+H]^+$=471. $^1$H NMR (DMSO-$d_6$): 8.07 (1 H, s), 7.58 (1 H, dd, J=10.71, 1.92 Hz), 7.43 (1 H, s), 7.38 (1 H, d, J=9.31 Hz), 7.31-7.28 (1 H, m), 6.89 (1 H, d, J=9.31 Hz), 6.35 (1 H, t, J=8.68 Hz), 3.69-3.60 (1 H, m), 3.45-3.38 (2 H, m), 0.96 (3 H, d, J=6.35 Hz).

Example 8

5-(4-Bromo-2-fluorophenylamino)-imidazo[1,5-a]pyridine-6-carboxylic acid (2-hydroxyethoxy)-amide

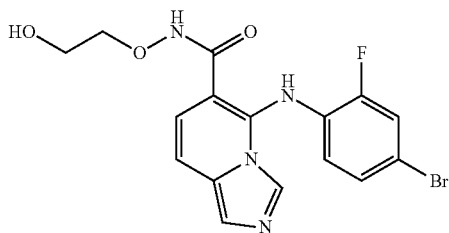

Step 1: 5-(4-Bromo-2-fluorophenylamino)-imidazo[1,5-a]pyridine-6-carboxylic acid (2-vinyloxyethoxy)-amide

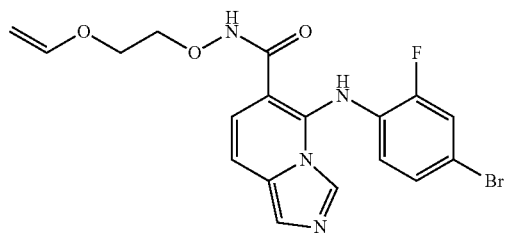 [SMILES: C=COCCONC(=O)c1ccc2cncn2c1Nc1ccc(Br)cc1F]

To a solution of 5-(4-Bromo-2-fluorophenylamino)-imidazo[1,5-a]pyridine-6-carboxylic acid (2.0 g, 5.7 mmol) and O-(2-vinyloxyethyl)-hydroxylamine (0.71 g, 6.8 mmol) in DMF (44 mL) was added EDCI hydrochloride (1.42 g, 7.41 mmol), HOBt (1.0 g, 7.41 mmol) and DIPEA (0.97 mL, 5.69 mmol). The reaction mixture was stirred at room temperature for 3 hours before being concentrated in vacuo. The resultant residue was dissolved in 1:1 diethylether:ethyl acetate (30 mL) and aqueous saturated sodium hydrogen carbonate solution (30 mL) was added. The resultant mixture was sonicated until a precipitate formed. The precipitate was collected by filtration and washed with 1:1 diethylether:ethyl acetate to yield the title compound as a tan solid (1.33 g, 53%). LCMS (Method B): $R_T$=2.78 min, $M+H^+$=435/437.

Step 2: 5-(4-Bromo-2-fluorophenylamino)-imidazo[1,5-a]pyridine-6-carboxylic acid (2-hydroxyethoxy)-amide To a suspension of 5-(4-Bromo-2-fluorophenylamino)-imidazo[1,5-a]pyridine-6-carboxylic acid (2-vinyloxyethoxy)-amide (1.33 g, 3.05 mmol) in methanol (40 mL) was added aqueous hydrochloric acid (6.7 mL, 1M, 6.7 mmol). The reaction mixture was stirred at room temperature for 30 minutes then concentrated in vacuo to remove the methanol. The resultant residue was dissolved in 1:1 diethylether:ethyl acetate (30 mL) and aqueous saturated sodium hydrogen carbonate solution (30 mL) added. The resultant mixture was sonicated until a precipitate formed, the precipitate collected by filtration and washed with water then diethyl ether to yield the title compound as a yellow solid (1.12 g, 90%). LCMS (method A): $R_T$=5.22 min, $[M+H]^+$=409/411. $^1$H NMR (DMSO-$d_6$, 400 MHz) 9.20 (1 H, s), 8.07 (1 H, s), 7.51 (1 H, dd, J=10.86, 2.22 Hz), 7.44 (1 H, s), 7.40 (1 H, d, J=9.33 Hz), 7.16 (1 H, ddd, J=8.61, 2.20, 1.07 Hz), 6.89 (1 H, d, J=9.31 Hz), 6.50 (1 H, t, J=8.84 Hz), 4.63 (1 H, s), 3.65 (2 H, t, J=4.79 Hz), 3.46 (3 H, s).

Example 9

5-(4-Bromo-2-fluoro-phenylamino)-imidazo[1,5-a]pyridine-6-carboxylic acid ((S)-2-hydroxy-propoxy)-amide

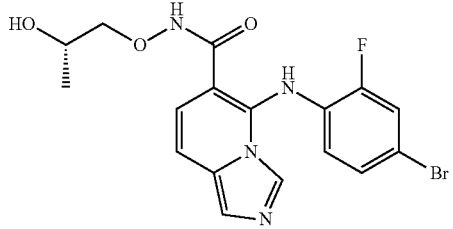 [SMILES: C[C@H](O)CONC(=O)c1ccc2cncn2c1Nc1ccc(Br)cc1F]

To a solution of 5-(4-bromo-2-fluoro-phenylamino)-imidazo[1,5-a]pyridine-6-carboxylic acid (271 mg, 0.77 mmol) in dioxane (3.9 mL) was added HOBT (306 mg, 2.3 mmol) and EDCI (442 mg, 2.3 mmol). The reaction mixture was stirred at ambient temperature for 30 minutes then (S)-1-aminooxy-propan-2-ol hydrochloride (294 mg, 2.3 mmol) and DIPEA (1.2 mL, 6.9 mmol) were added, the mixture was then stirred for 60 hours at ambient temperature. The reaction mixture was diluted with ethyl acetate then washed with a saturated aqueous solution of sodium bicarbonate followed by water and brine. The organic phase was isolated, dried ($Na_2SO_4$), filtered and concentrated in vacuo. The resultant residue was subjected to flash chromatography (Si-PPC, gradient 0 to 100%, ethyl acetate in dichloromethane, then gradient 0 to 10%, methanol in dichloromethane) to afford the title compound as a green/yellow solid (80 mg, 25%). LCMS (method A): $R_T$=5.71 min, $[M+H]^+$=423/425. $^1$H NMR (DMSO-$d_6$): 8.10 (1 H, s), 7.51 (1 H, dd, J=10.87, 2.22 Hz), 7.43 (1 H, s), 7.39 (1 H, d, J=9.31 Hz), 7.18-7.14 (1 H, m), 6.88 (1 H, d, J=9.31 Hz), 6.51 (1 H, t, J=8.85 Hz), 4.69 (1 H, s), 3.68-3.59 (1 H, m), 3.42 (2 H, d, J=5.81 Hz), 0.95 (3 H, d, J=6.35 Hz).

Example 10

5-(4-Bromo-2-fluoro-phenylamino)-8-fluoro-imidazo[1,5-a]pyridine-6-carboxylic acid ((S)-2-hydroxy-propoxy)-amide

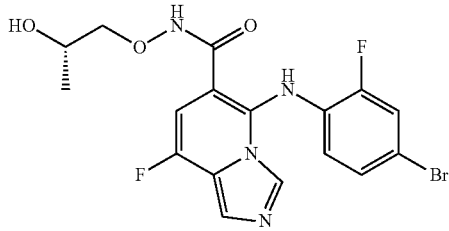 [SMILES: C[C@H](O)CONC(=O)c1cc(F)c2cncn2c1Nc1ccc(Br)cc1F]

To a solution of 5-(4-bromo-2-fluoro-phenylamino)-8-fluoro-imidazo[1,5-a]pyridine-6-carboxylic acid methyl ester (351 mg, 0.92 mmol) in IMS (10 mL) was added sodium hydroxide (1.0 mL, 1M aqueous solution, 1.0 mmol). The reaction mixture was heated at 65° C. for 1 hour, and then concentrated in vacuo. The resultant residue was azeotroped with toluene and then suspended in dioxane. EDCI (353 mg, 1.84 mmol) and HOBt (248 mg, 1.84 mmol) were added and the mixture was stirred at room temperature for 20 minutes. (S)-1-Aminooxy-propan-2-ol hydrochloride (235 mg, 1.84 mmol) and DIPEA (0.63 mL, 3.68 mmol) were added and the resultant mixture was stirred for 18 hours, before being concentrated under reduced pressure. The resultant residue was taken up in ethyl acetate then washed with a saturated aqueous solution of sodium bicarbonate followed by water and brine. The organic phase was isolated, dried ($Na_2SO_4$), filtered and concentrated in vacuo. The resultant residue was subjected to flash chromatography (Si-PPC, gradient 0 to 10%, methanol in dichloromethane) to give a pale yellow solid (124 mg), which was further purified by preparative HPLC (Gemini 5 micron $C_{18}$ 250×21.20 mm column, 0.1% formic acid, gradient acetonitrile/water, 5 to 85%, ramp time 15 minutes) to afford the title compound as an off-white solid (70 mg, 17%). LCMS (method A): $R_T$=7.83 min, [M+H]$^+$=441/443. $^1$H NMR (CDCl$_3$): 9.45 (1 H, s), 8.99 (1 H, s), 7.76 (1 H, d, J=2.95 Hz), 7.59 (1 H, s), 7.29 (1 H, dd, J=10.10, 2.16 Hz), 7.12 (1 H, d, J=8.52 Hz), 6.50 (1 H, d, J=10.18 Hz), 6.41 (1 H, t, J=8.54 Hz), 4.03 (1 H, t, J=7.52 Hz), 3.94 (1 H, d, J=11.57 Hz), 3.70 (1 H, t, J=10.24 Hz), 1.14 (3 H, d, J=6.46 Hz).

Example 11

8-Fluoro-5-(2-fluoro-4-iodo-phenylamino)-imidazo[1,5-a]pyridine-6-carboxylic acid (2-hydroxy-ethoxy)-amide

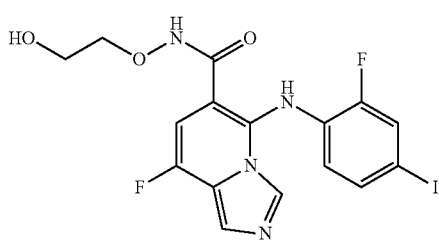 [SMILES: O=C(NOCCO)c1cc(F)c2cncn2c1Nc1ccc(I)cc1F]

Step 1: 8-Fluoro-5-(2-fluoro-4-iodo-phenylamino)-imidazo[1,5-a]pyridine-6-carboxylic acid (2-vinyloxy-ethoxy)-amide

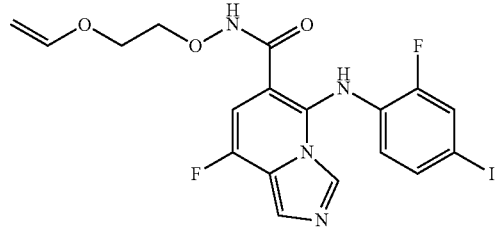 [SMILES: C=COCCONC(=O)c1cc(F)c2cncn2c1Nc1ccc(I)cc1F]

8-Fluoro-5-(2-fluoro-4-iodo-phenylamino)-imidazo[1,5-a]pyridine-6-carboxylic acid (0.20 g, 0.48 mmol), O-(2-vinyloxyethyl)-hydroxylamine (55 mg, 0.53 mmol), EDCI (102 mg, 0.53 mmol), HOBt (72 mg, 0.53 mmol) and DIPEA (90 µL, 0.53 mmol) were dissolved in DMF (10 mL) and the reaction mixture stirred at room temperature for 16 hours before being concentrated in vacuo. The resultant residue was dissolved in ethyl acetate (10 mL), washed with aqueous saturated sodium bicarbonate solution (10 mL) and the aqueous fraction extracted twice with ethyl acetate (2×10 mL). The combined organic fractions were washed with brine (20 mL), dried (MgSO$_4$) and concentrated in vacuo. The resultant residue was subjected to flash chromatography (SiO$_2$, gradient 0-10% methanol in DCM) to yield the title compound as a pale yellow solid (200 mg, 83%). LCMS (Method B): $R_T$=3.41 min, [M+H]$^+$=501.

Step 2: 8-Fluoro-5-(2-fluoro-4-iodo-phenylamino)-imidazo[1,5-a]pyridine-6-carboxylic acid (2-hydroxy-ethoxy)-amide A solution of 8-fluoro-5-(2-fluoro-4-iodo-phenylamino)-imidazo[1,5-a]pyridine-6-carboxylic acid (2-vinyloxy-ethoxy)-amide (200 mg, 0.39 mmol) in methanol (1 mL) was loaded onto an SCX-2 column. The column was washed with methanol (10 mL) then the product was then eluted with ammonia in methanol (20 mL, 2M), the appropriate fractions were concentrated in vacuo. The resultant residue was subjected to reverse phase preperative HPLC (10-90% acetonitrile/water 0.1% formic acid, Phenominex gemini PhC6, 5 micron, 250×20 mm). The resultant product was dissolved in ethyl acetate (5 mL) and washed with aqueous saturated sodium bicarbonate solution (10 mL). The aqueous fraction was extracted twice with ethyl acetate (2×10 mL) and the combined organics were washed with brine (20 mL), dried (MgSO$_4$) and concentrated in vacuo to yield the title compound as a white solid (88 mg, 39%). LCMS (Method A): $R_T$=7.71 min, [M+H]$^+$=475. $^1$H NMR (DMSO-d$_6$): 8.20 (1 H, s), 7.60 (1 H, s), 7.57 (1 H, dd, J=10.73, 1.96 Hz), 7.26 (1 H, dd, J=8.43, 1.82 Hz), 6.82 (1 H, d, J=11.14 Hz), 6.30 (1 H, t, J=8.71 Hz), 3.65 (2 H, t, J=4.77 Hz), 3.45 (2 H, t, J=4.68 Hz).

Example 12

8-Fluoro-5-(2-fluoro-4-iodo-phenylamino)-imidazo[1,5-a]pyridine-6-carboxylic acid ((R)-2,3-dihydroxy-propoxy)-amide

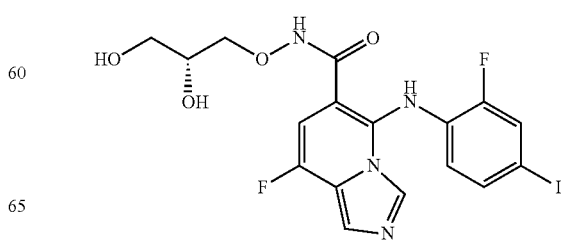

Step 1: 8-Fluoro-5-(2-fluoro-4-iodo-phenylamino)-imidazo[1,5-a]pyridine-6-carboxylic acid ((R)-2,2-dimethyl-[1,3]dioxolan-4-ylmethoxy)-amide

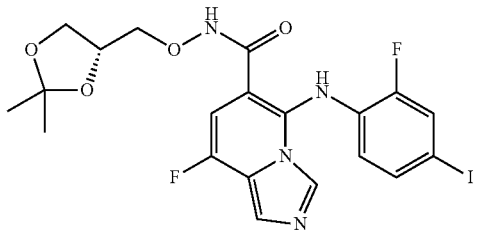 [SMILES: CC1(C)OC[C@H](CONC(=O)c2cc(F)c3cncn3c2Nc2ccc(I)cc2F)O1]

8-Fluoro-5-(2-fluoro-4-iodo-phenylamino)-imidazo[1,5-a]pyridine-6-carboxylic acid (235 mg, 0.57 mmol), O—(((R)-2,2-dimethyl-[1,3]dioxolan-4-ylmethyl)-hydroxylamine (92 mg, 0.62 mmol), EDCI (120 mg, 0.62 mmol), HOBt (84 mg, 0.62 mmol) and DIPEA (0.1 mL, 0.62 mmol) were dissolved in DMF (10 mL) and the reaction mixture stirred at room temperature for 72 hours before being concentrated in vacuo. The resultant residue was dissolved in ethyl acetate (10 mL), washed with aqueous saturated sodium bicarbonate solution (10 mL) and the aqueous fraction extracted twice with ethyl acetate (2×10 mL). The combined organic fractions were washed with brine (20 mL), dried with MgSO$_4$ and concentrated in vacuo. The resultant residue was subjected to flash chromatography (SiO$_2$, gradient 0-10% methanol in DCM) to yield the title compound as a pale yellow solid (298 mg, 97%). LCMS (Method B): R$_T$=3.34 min, [M+H]$^+$=545.

Step 2: 8-Fluoro-5-(2-fluoro-4-iodo-phenylamino)-imidazo[1,5-a]pyridine-6-carboxylic acid ((R)-2,3-dihydroxy-propoxy)-amide To a solution of 8-fluoro-5-(2-fluoro-4-iodo-phenylamino)-imidazo[1,5-a]pyridine-6-carboxylic acid ((R)-2,2-dimethyl-[1,3]-dioxolan-4-ylmethoxy)-amide (298 mg, 0.55 mmol) in methanol (5 mL) was added hydrochloric acid in dioxane (2 mL, 4N, 8.0 mmol). The reaction mixture was stirred at room temperature for 1 hour then concentrated in vacuo. The resultant residue was dissolved in ethyl acetate (5 mL), washed with aqueous saturated sodium bicarbonate solution (10 mL) and the aqueous fraction extracted twice with ethyl acetate (2×5 mL). The combined organic fractions were washed with brine (10 mL), dried (MgSO$_4$) and concentrated in vacuo. The resultant residue was subjected to reverse phase preparative HPLC (10-90% acetonitrile/water 0.1% formic acid, Phenominex gemini PhC6, 5 micron, 250× 20 mm). The resultant product was dissolved in ethyl acetate (5 mL) and washed with aqueous saturated sodium bicarbonate solution (10 mL). The aqueous fraction was extracted twice with ethyl acetate (2×10 mL) and the combined organics washed with brine (20 mL), dried (MgSO$_4$) and concentrated in vacuo to yield the title compound as a white solid (83 mg, 30%). LCMS (Method A): R$_T$=7.11 min, [M+H]$^+$=505. $^1$H NMR (DMSO-d$_6$): 11.63 (1 H, s), 8.97 (1 H, s), 8.22 (1 H, d, J=3.06 Hz), 7.61 (1 H, s), 7.57 (1 H, dd, J=10.74, 1.93 Hz), 7.26 (1 H, d, J=8.50 Hz), 6.82 (1 H, d, J=11.09 Hz), 6.32 (1 H, t, J=8.74 Hz), 3.72-3.65 (1 H, m), 3.59-3.50 (2 H, m), 3.29 (2 H, m).

Example 13

8-Fluoro-5-(2-fluoro-4-iodo-phenylamino)-imidazo[1,5-a]pyridine-6-carboxylic acid ((S)-2-hydroxy-propoxy)-amide

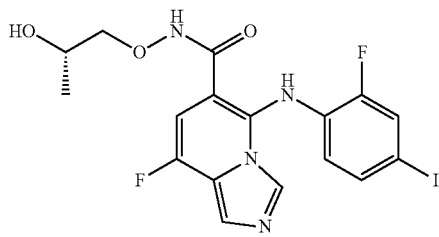

A suspension of 8-fluoro-5-(2-fluoro-4-iodo-phenylamino)-imidazo[1,5-a]pyridine-6-carboxylic acid (100 mg, 0.23 mmol), HATU (130 mg, 0.34 mmol), DIPEA (0.06 mL, 0.34 mmol) and (S)-2-hydroxy-propoxy-amide hydrochloride (44 mg, 0.34 mmol) in THF (1 mL) was stirred at room temperature for 18 hours. The reaction mixture was partitioned between ethyl acetate (5 mL) and 1M HCl, the organic layer was isolated and washed with saturated aqueous NaHCO$_3$ (2×5 mL) and brine (2×5 mL), dried over Na$_2$SO$_4$, filtered and concentrated in vacuo. The resultant residue was subjected to reverse-phase preparative HPLC (Gemini 5 micron C$_{18}$ 250×21.20 mm column, 0.1% formic acid, gradient acetonitrile/water, 5 to 98%, ramp time 20 minutes) to afford the title compound as a yellow solid (13 mg, 8%). LCMS (method A): R$_T$=8.13 min, [M+H]$^+$=489. $^1$H NMR (DMSO-d$_6$): 11.51 (1 H, broad), 8.95 (1 H, broad), 8.25 (1 H, s), 7.60 (1 H, s), 7.55 (1 H, d, J=10.7 Hz), 7.27 (1 H, d, J=8.4 Hz), 6.82 (1 H, d, J=11.1 Hz), 6.32 (1 H, t, J=8.8 Hz), 4.66 (1 H, broad), 3.64 (1 H, m), 3.43 (2 H, d, J=5.8 Hz), 0.94 (3 H, d, J=6.3 Hz).

Example 14

5-(2-Fluoro-4-methanesulfanyl-phenylamino)-imidazo[1,5-a]pyridine-6-carboxylic acid (2-hydroxy-ethoxy)-amide

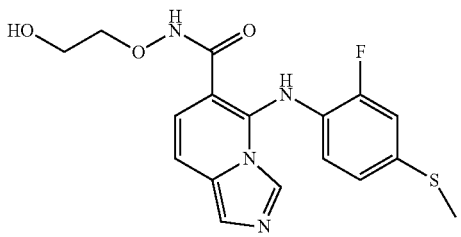 [SMILES: CSc1ccc(Nc2c(C(=O)NOCCO)ccc3cncn23)c(F)c1]

Step 1: 5-(2-Fluoro-4-methanesulfanyl-phenylamino)-imidazo[1,5-a]pyridine-6-carboxylic acid (2-vinyloxy-ethoxy)-amide

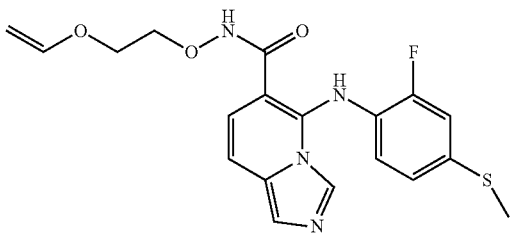 [SMILES: C=COCCONC(=O)c1ccc2cncn2c1Nc1ccc(SC)cc1F]

To a mixture of 5-(2-fluoro-4-methanesulfanyl-phenylamino)-imidazo[1,5-a]pyridine-6-carboxylic acid (400 mg, 1.26 mmol), O-(2-vinyloxyethyl)-hydroxylamine (260 mg, 2.52 mmol) and HOBt (221 mg, 1.64 mmol) in DMF (5 mL) was added EDCI hydrochloride (312 mg, 1.64 mmol), and DIPEA (0.285 mL, 1.64 mmol) and the mixture stirred at room temperature for 20 hours. The products were partitioned between ethyl acetate and saturated aqueous $NaHCO_3$. The organic layer was separated and washed with brine, then dried ($Na_2SO_4$), filtered and concentrated in vacuo to give the title compound (263 mg, 52%). LCMS (Method B): $R_T$ 2.64 $[M+H]^+$403.

Step 2: 5-(2-fluoro-4-methanesulfanyl-phenylamino)-imidazo[1,5-a]pyridine-6-carboxylic acid (2-hydroxy-ethoxy)-amide To a solution 5-(2-fluoro-4-methanesulfanyl-phenylamino)-imidazo[1,5-a]pyridine-6-carboxylic acid (2-vinyloxy-ethoxy)-amide (263 mg, 0.65 mmol) in methanol (10 mL) was added 1M hydrochloric acid (1 mL, 1 mmol.) and the mixture stirred at room temperature for 2 hours. The resultant mixture was concentrated in vacuo before being partitioned between saturated aqueous $NaHCO_3$ and ethyl acetate. The organic layer was separated, washed with water, dried ($Na_2SO_4$), filtered and concentrated in vacuo. The resultant residue was triturated with ethyl acetate and the solid collected by filtration was subjected to flash chromatography (Si-PPC, gradient 0 to 10%, methanol in DCM) to afford the title compound as a tan solid (123 mg, 50%). LCMS (method A): $R_T$=5.15 min, $[M+H]^+$=377. $^1$H NMR (DMSO-$d_6$, 400 MHz) 11.54 (1H, s), 9.39 (1 H, s), 7.93 (1 H, s), 7.39 (1 H, s), 7.32 (1 H, d, J=9.36 Hz), 7.16 (1 H, dd, J=11.86, 2.13 Hz), 6.93-6.88 (2 H, m), 6.57 (1 H, t, J=8.65 Hz), 4.62 (1 H, s), 3.66 (2 H, t, J=4.85 Hz), 3.45 (2 H, t, J=4.77 Hz), 2.40 (3 H, s).

Example 15

5-(2-Fluoro-4-iodo-phenylamino)-imidazo[1,5-a]pyrazine-6-carboxylic acid (2-hydroxy-ethoxy)-amide

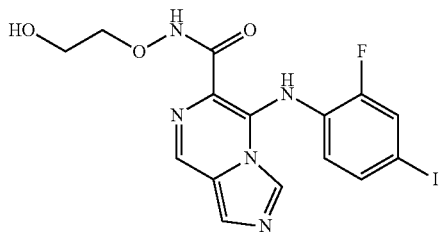 [SMILES: O=C(NOCCO)c1ncc2cncn2c1Nc1ccc(I)cc1F]

Step 1: 5-(2-Fluoro-4-iodo-phenylamino)-imidazo[1,5-a]pyrazine-6-carboxylic acid

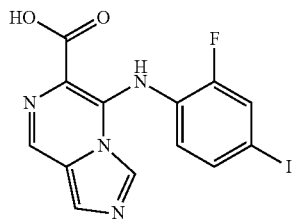 [SMILES: O=C(O)c1ncc2cncn2c1Nc1ccc(I)cc1F]

To a solution of 5-(2-fluoro-4-iodo-phenylamino)-imidazo[1,5-a]pyrazine-6-carboxylic acid methyl ester (140 mg, 0.34 mmol) in anhydrous 1,2-dichloroethane (2.5 mL) was added trimethyltin hydroxide (215 mg, 1.19 mmol, 3.5 eq.). The reaction mixture was heated at 85° C. for 1 hour and then cooled to RT. The reaction mixture was concentrated in vacuo, and the crude residue was diluted with ethyl acetate. The organic layer was washed with 1N HCl (3×), water and brine, dried ($Na_2SO_4$), filtered and concentrated in vacuo. Crystallization from dichloromethane ether hexane afforded the title compound as a yellow solid (132.1 mg, 97.7%). $^1$H NMR (MeOD, 400 MHz) δ ppm 8.76 (s, 1H), 7.92 (s, 1H), 7.86 (s, 1H), 7.64 (dd, J=10.13, 1.84 Hz, 1H), 7.55-7.50 (m, 1H), 6.72 (t, J=8.49 Hz, 1H); LCMS (method D1): $R_T$=0.77 min, $[M+H]^+$=399.

Step 2: 5-(2-Fluoro-4-iodo-phenylamino)-imidazo[1,5-a]pyrazine-6-carboxylic acid (2-vinyloxy-ethoxy)-amide

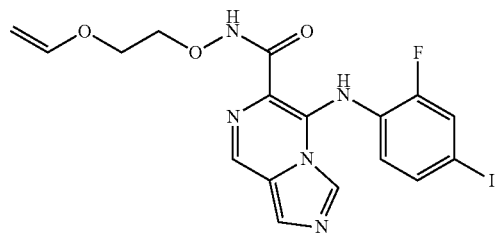 [SMILES: C=COCCONC(=O)c1ncc2cncn2c1Nc1ccc(I)cc1F]

A mixture of 5-(2-fluoro-4-iodo-phenylamino)-imidazo[1,5-a]pyrazine-6-carboxylic acid (110 mg, 0.28 mmol), O-(2-vinyloxy-ethyl)-hydroxylamine (45.6 mg, 0.44 mmol, 1.6 eq.), HATU (157.6 mg, 0.41 mmol, 1.5 eq.), and DIPEA (96.0 μL, 0.55 mmol, 2.0 eq.) in anhydrous DMF (4.2 mL) was stirred for 18 hours under $N_2$ at ambient temperature. The reaction mixture was diluted with ethyl acetate and washed with a saturated aqueous solution of sodium bicarbonate followed by water and brine. The organic phase was isolated, dried ($Na_2SO_4$), filtered and concentrated in vacuo. The resultant residue was subjected to flash chromatography (Si-PPC, gradient 0% to 15%, methanol in dichloromethane) to afford the desired product as a yellow solid (24 mg, 18%). LCMS (method D1): $R_T$=1.00 min, $[M+H]^+$=484.

Step 3: 5-(2-Fluoro-4-iodo-phenylamino)-imidazo[1,5-a]pyrazine-6-carboxylic acid (2-hydroxy-ethoxy)-amide To a solution of 5-(2-fluoro-4-iodo-phenylamino)-imidazo[1,5-a]pyrazine-6-carboxylic acid (2-vinyloxy-ethoxy)-amide (24.0 mg, 0.05 mmol) in methanol (0.5 mL) and dichloromethane (1.0 mL) was added 4M HCl in 1,4-dioxane (30 μL, 0.1 mmol, 2.5 eq.), and the reaction was stirred at ambient temperature under $N_2$ for 2 h. The reaction mixture was concentrated in vacuo then poured into ethyl acetate. The organic layer was washed with a saturated solution of sodium bicarbonate, water, and brine. The organic phase was isolated, dried ($Na_2SO_4$), filtered and concentrated in vacuo. The resultant residue was subjected to flash chromatography (Si-PPC, gradient 0% to 25%, methanol in dichloromethane) to afford the title compound as yellow solid (11.6 mg, 51%). $^1$H NMR (MeOD, 400 MHz) δ ppm 8.74 (s, 1H), 7.87 (s, 1H), 7.84 (s, 1H), 7.62 (dd, J=10.20, 1.82 Hz, 1H), 7.48 (d, J=8.41

Hz, 1H), 6.61 (t, J=8.53 Hz, 1H), 4.05 (t, J=4.80 Hz, 2H), 3.78 (t, J=4.80 Hz, 2H)); LCMS (method E1): $R_T$=4.33 min, [M+H]$^+$=458.

Example 16

5-(2-fluoro-4-iodo-phenylamino)-imidazo[1,5-a]pyrazine-6-carboxylic acid ((S)-2-hydroxy-propoxy)-amide

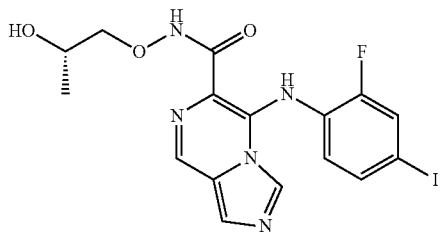

To a solution of 5-(2-fluoro-4-iodo-phenylamino)-imidazo[1,5-a]pyrazine-6-carboxylic acid (85 mg, 0.21 mmol) in anhydrous DMF (1.0 mL) was added (S)-1-aminooxy-propan-2-ol hydrochloride (32.7 mg, 0.26 mmol, 1.2 eq.), DIPEA (0.13 mL, 0.77 mmol, 3.6 eq.), HOBt (36.0 mg, 0.26 mmol, 1.2 eq.) and EDCI (51.2 mg, 0.26 mmol, 1.2 eq.), and the reaction mixture was stirred at ambient temperature under N$_2$ for 16 hours. The reaction mixture was poured into ethyl acetate, and the organic layer was washed with a saturated solution of sodium bicarbonate, 50% brine and brine. The organic phase was isolated, dried (Na$_2$SO$_4$), filtered and concentrated in vacuo. The resultant residue was subjected to flash chromatography (Si-PPC, gradient 0% to 40%, methanol in ethyl acetate) to give an oil. Crystallization from dichloromethane ether hexane afforded the title compound as a yellow solid (10.7 mg, 10.6%). $^1$H NMR (MeOD, 400 MHz) δ ppm 8.76 (s, 1H), 7.92 (s, 1H), 7.86 (s, 1H), 7.64 (dd, J=10.13, 1.84 Hz, 1H), 7.55-7.50 (m, 1H), 6.72 (t, J=8.49 Hz, 1H); LCMS (method E1): $R_T$=5.14 min, [M+H]$^+$=472.

Example 17

5-(4-Cyclopropyl-2-fluoro-phenylamino)-imidazo[1,5-a]pyridine-6-carboxylic acid (2-hydroxy-ethoxy)-amide

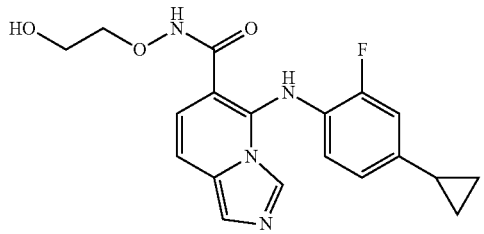 [SMILES: O=C(NOCCO)c1ccc2cncn2c1Nc1ccc(C2CC2)cc1F]

Step 1: 5-(4-Cyclopropyl-2-fluoro-phenylamino)-imidazo[1,5-a]pyridine-6-carboxylic acid (2-vinyloxy-ethoxy)-amide

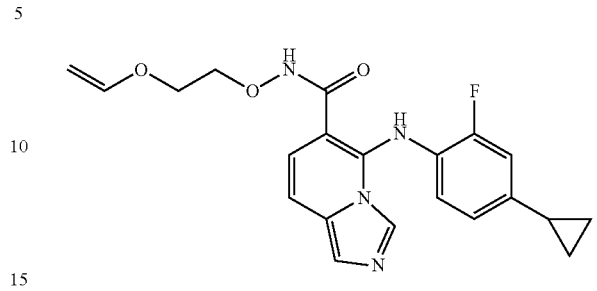

To a mixture of 5-(4-cyclopropyl-2-fluoro-phenylamino)-imidazo[1,5-a]pyridine-6-carboxylic acid (400 mg, 1.29 mmol), O-(2-vinyloxyethyl)-hydroxylamine (265 mg, 2.57 mmol) and HOBt (225 mg, 1.67 mmol) in DMF (5 mL) was added EDCI hydrochloride (320 mg, 1.67 mmol), and DIPEA (0.290 mL, 1.67 mmol) before the reaction mixture was stirred at room temperature for 18 hours. The products were partitioned between ethyl acetate and saturated aqueous NaHCO$_3$, the organic layer separated and washed with brine then dried (Na$_2$SO$_4$), filtered and concentrated in vacuo. The resultant residue was subjected to flash chromatography (Si-PPC, gradient 0-35% ethyl acetate in cylcohexane) to give the title compound (270 mg, 53%). LCMS (Method B): $R_T$ 2.79 [M+H]$^+$397.

Step 2: 5-(4-Cyclopropyl-2-fluoro-phenylamino)-imidazo[1,5-a]pyridine-6-carboxylic acid (2-hydroxy-ethoxy)-amide To a solution of 5-(4-cyclopropyl-2-fluoro-phenylamino)-imidazo[1,5-a]pyridine-6-carboxylic acid (2-vinyloxy-ethoxy)-amide (270 mg, 0.681 mmol) in methanol (10 mL) was added 1M hydrochloric acid (2 mL, 2 mmol.) and the mixture stirred at room temperature for 2 hours. Solvent was removed in vacuo, and then saturated aqueous NaHCO$_3$ added and the mixture extracted with ethyl acetate. The organic layer was separated, dried (Na$_2$SO$_4$), filtered and concentrated in vacuo. The resultant residue was triturated with TBME and the solid collected by filtration to give the title compound as an off-white solid (103 mg, 41%). LCMS (Method A): $R_T$ 5.68 [M+H]$^+$371. $^1$H NMR (DMSO-d$_6$, 400 MHz) 7.81 (1 H, s), 7.37-7.34 (1 H, m), 7.27 (1 H, d, J=9.37 Hz), 6.95 (1 H, d, J=9.34 Hz), 6.91 (1 H, dd, J=12.49, 1.92 Hz), 6.75 (1 H, dd, J=8.27, 1.96 Hz), 6.56-6.46 (1 H, m), 3.71-3.65 (2 H, m), 3.48-3.43 (2 H, m), 1.89-1.80 (1 H, m), 0.91-0.85 (2 H, m), 0.65-0.57 (2 H, m).

Example 18

(R)—N-(2,3-Dihydroxypropoxy)-5-(2-fluoro-4-iodophenylamino)imidazo[1,5-a]pyrazine-6-carboxamide

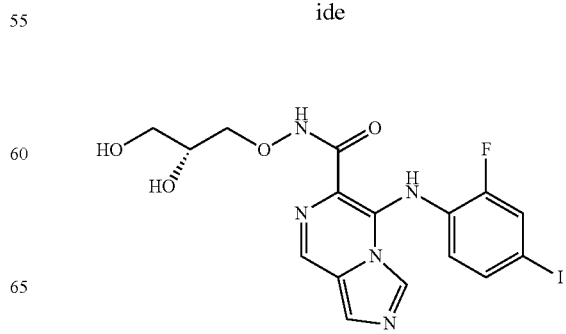

Step 1: (R)—N-((2,2-Dimethyl-1,3-dioxolan-4-yl)methoxy)-5-(2-fluoro-4-iodophenylamino)imidazo[1,5-a]pyrazine-6-carboxamide

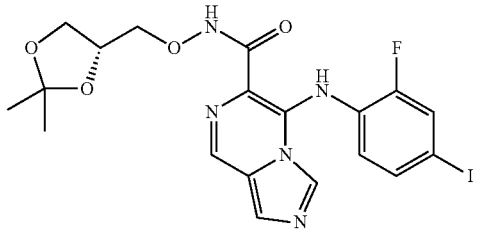 [SMILES: CC1(C)OC[C@H](CONC(=O)c2ncc3cncn3c2Nc2ccc(I)cc2F)O1]

To a solution of 5-(2-fluoro-4-iodo-phenylamino)-imidazo[1,5-a]pyrazine-6-carboxylic acid (100.0 mg, 0.25 mmol) in anhydrous DMF (2.5 mL) was added, in order, (R)-O4(2,2-dimethyl-1,3-dioxolan-4-yl)methyphydroxylamine (40.7 mg, 0.28 mmol, 1.1 eq.), HOBt (37.3 mg, 0.27 mmol, 1.1 eq.), EDCI (53.0 mg, 0.27 mmol, 1.1 eq.), and N-methylmorpholine (0.1 mL, 0.91 mmol, 3.6 mmol). The reaction mixture was stirred at room temperature under $N_2$ for 3 days. The reaction mixture was diluted with ethyl acetate, and the organic layer was washed with a saturated solution of sodium bicarbonate, water and brine. The organic phase was isolated, dried ($Na_2SO_4$), filtered and concentrated in vacuo. The resultant residue was subjected to flash chromatography (Si-PPC, gradient 80% to 100%, ethyl acetate in hexane, followed by gradient 0 to 20% methanol in ethyl acetate) to give a yellow solid (72.6 mg, 54.8%). LCMS (method D1): $R_T$=0.97 min, $[M+H]^+$=528.

Step 2: (R)—N-(2,3-Dihydroxypropoxy)-5-(2-fluoro-4-iodophenylamino)imidazo[1,5-a]pyrazine-6-carboxamide To a heterogeneous mixture of (R)—N-((2,2-dimethyl-1,3-dioxolan-4-yl)methoxy)-5-(2-fluoro-4-iodophenylamino)imidazo[1,5-a]pyrazine-6-carboxamide (69.5 mg, 0.13 mmol) in anhydrous methanol (1.6 mL) was added 4M HCl in 1,4-dioxane (0.13 mL, 0.5 mmol, 4.0 eq). The reaction mixture was stirred at room temperature for 10 minutes. Solid sodium sulfate (200 mg) was then added. The reaction mixture was absorbed onto silica and then subjected to flash chromatography (Si-PPC, gradient 0% to 40% methanol in dichloromethane) to give the title compound as yellow foam (43.2 mg, 67.3%). $^1$H NMR (DMSO-$d_6$, 400 MHz) δ ppm 11.90 (s, 1H), 10.30 (s, 1H), 8.82 (s, 1H), 7.95 (s, 1H), 7.91 (s, 1H), 7.74 (d, J=9.6 Hz, 1H), 7.44 (d, 8.4 Hz, 1H), 6.60 (t, J=8.4 Hz, 1H), 4.86 (d, J=4.4 Hz, 1H), 4.55 (broad s, 1H), 3.99-3.91 (m, 1H), 3.79-3.69 (m, 2H), 3.39 (broad s, 2H); LCMS (method E2): $R_T$=8.40 min, $[M+H]^+$=488.

Example 19

N-Ethoxy-5-(2-fluoro-4-iodophenylamino)imidazo[1,5-a]pyrazine-6-carboxamide

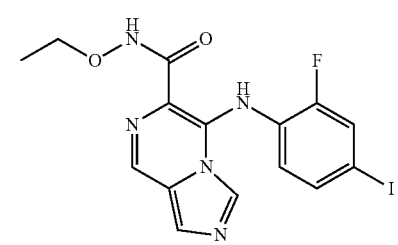 [SMILES: CCONC(=O)c1ncc2cncn2c1Nc1ccc(I)cc1F]

To a solution of 5-(2-fluoro-4-iodo-phenylamino)-imidazo[1,5-a]pyrazine-6-carboxylic acid methyl ester (165.0 mg, 0.40 mmol) and O-ethylhydroxylamine hydrochloride (78.1 mg, 0.80 mmol, 2.0 eq) in anhydrous THF (9.4 mL) at 0° C. was added lithium hexamethyldisilazide (1M in THF, 1.2 mL, 1.2 mmol, 3.0 eq). After stirring at room temperature for 16 h, additional O-ethylhydroxylamine hydrochloride (234.3 mg, 2.40 mmol, 3.0 eq) and lithium hexamethyldisilazide (1M in THF, 3.6 mL, 3.6 mmol, 9.0 eq) were added at 0° C., and the reaction mixture was stirred at room temperature for 3 days. The reaction mixture was then quenched with saturated aqueous solution of sodium bicarbonate (5 mL) and diluted with ethyl acetate (50 mL). The organic layer was isolated and washed with water and brine, dried ($Na_2SO_4$), filtered and concentrated in vacuo. The resultant residue was subjected to flash chromatography (Si-PPC, gradient 45% to 100%, ethyl acetate in hexane, followed by gradient 0 to 15% methanol in ethyl acetate) to give an oil. Crystallization from DCM ether hexane afforded the title compound as a yellow solid (33.7 mg, 19.1%). $^1$H NMR (DMSO-$d_6$, 400 MHz) δ ppm 11.86 (s, 1H), 10.38 (s, 1H), 8.82 (s, 1H), 7.94 (s, 1H), 7.92 (s, 1H), 7.73 (d, J=10.4 Hz, 1H), 7.44 (d, 8.4 Hz, 1H), 6.57 (t, J=8.4 Hz, 1H), 3.90 (q, J=7.2 Hz, 2H), 1.18 (t, J=6.8 Hz, 3H); LCMS (method D2): $R_T$=1.24 min, $[M+H]^+$=442.

Example 20

N-(Cyclopropylmethoxy)-5-(2-fluoro-4-iodophenylamino)imidazo[1,5-a]pyrazine-6-carboxamide

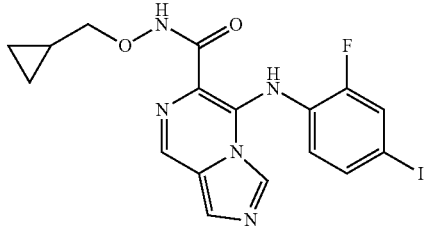 [SMILES: O=C(NOCC1CC1)c1ncc2cncn2c1Nc1ccc(I)cc1F]

The title compound was prepared in an analogous fashion to N-ethoxy-5-(2-fluoro-4-iodophenylamino)imidazo[1,5-a]pyrazine-6-carboxamide, using O-(cyclopropylmethyl)-hydroxylamine hydrochloride as the starting material. $^1$H NMR (DMSO-$d_6$, 400 MHz) δ ppm 11.82 (s, 1H), 10.36 (s, 1H), 8.82 (s, 1H), 7.95 (s, 1H), 7.91 (s, 1H), 7.73 (dd, J=10.4 Hz, 1.8 Hz, 1H), 7.44 (d, 8.4 Hz, 1H), 6.58 (t, J=8.4 Hz, 1H), 3.67 (d, J=7.2 Hz, 2H), 1.12 to 1.01 (m, 1H), 0.54-0.48 (m, 2H), 0.28-0.23 (m, 2H); LCMS (method D2): $R_T$=1.33 min, $[M+H]^+$=468.

Example 21

5-(2-Fluoro-4-iodophenylamino)-N-methylimidazo[1,5-a]pyrazine-6-carboxamide

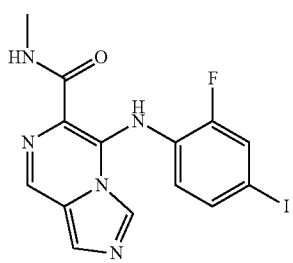 [SMILES: CNC(=O)c1ncc2cncn2c1Nc1ccc(I)cc1F]

To a solution of 5-(2-fluoro-4-iodo-phenylamino)-imidazo[1,5-a]pyrazine-6-carboxylic acid methyl ester (108 mg, 0.26 mmol) in anhydrous methanol (0.5 mL) was added 2M methylamine in THF (1.3 mL, 2.6 mmol, 10 eq), and the reaction mixture was stirred at room temperature under $N_2$ for 3 days. The reaction mixture was diluted with ethyl acetate (50 mL). The organic layer was washed with water and brine, dried ($Na_2SO_4$), filtered and concentrated in vacuo. The resultant residue was subjected to reverse-phase preparative HPLC [Gemini-NX (100×30 mm, 10 micron), 0.1% FA in water/acetonitrile, 5-85%, ramp time in 10 minutes, flow at 60 ml/min] to afford the title compound as a white solid (48.3 mg, 44.8%). $^1$H NMR (DMSO-$d_6$, 400 MHz) δ ppm 10.89 (s, 1H), 8.95 to 8.91 (m, 1H), 8.86 (s, 1H), 7.92 (s, 1H), 7.88 (s, 1H), 7.76 (dd, J=8.4 Hz, 1.2 Hz, 1H), 7.44 (d, J=6.8 Hz, 1H), 6.51 (t, J=6.8 Hz, 1H), 2.81 (d, 4.0 Hz, 3H); LCMS (method E2): $R_T$=12.23 min, [M+H]$^+$=412.

Example 22

5-(4-Bromo-2-fluorophenylamino)-N-(2-hydroxy-ethoxy)imidazo[1,5-a]pyrazine-6-carboxamide

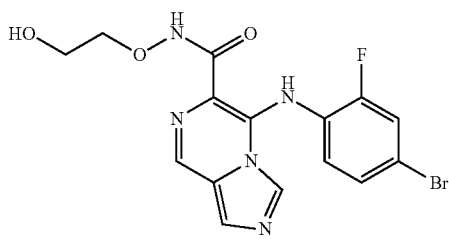 [SMILES: O=C(NOCCO)c1ncc2cncn2c1Nc1ccc(Br)cc1F]

Step 1: 5-(4-Bromo-2-fluorophenylamino)-N-(2-(vinyloxy)ethoxy)-imidazo[1,5-a]pyrazine-6-carboxamide

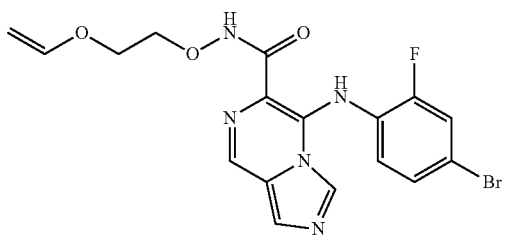 [SMILES: C=COCCONC(=O)c1ncc2cncn2c1Nc1ccc(Br)cc1F]

To a stirred solution of 5-(4-bromo-2-fluoro-phenylamino)-imidazo[1,5-a]pyrazine-6-carboxylic acid methyl ester (150 mg, 0.41 mmol) and O-(2-vinyloxy-ethyl)hydroxylamine (127 mg, 1.23 mmol, 3.0 eq) in anhydrous THF (7.5 mL) at 0° C. was added lithium hexamethyldisilazide (1M in THF, 1.2 mL, 1.23 mmol, 3.0 eq.), and the reaction mixture was stirred at room temperature. After 1 h the reaction mixture was quenched with saturated aqueous solution of sodium bicarbonate and diluted with ethyl acetate. The organic layer was isolated and washed with water and brine, dried ($Na_2SO_4$), filtered and concentrated in vacuo. The resultant residue was subjected to flash chromatography (Si-PPC, gradient 0 to 5% methanol in dichloromethane) to give an oil. Crystallization from DCM ether hexane afforded the desired product as a pale orange solid (160.2 mg, 89.4%). LCMS (method C): $R_T$=2.53 min, [M+H]$^+$=437/439.

Step 2: 5-(4-Bromo-2-fluorophenylamino)-N-(2-hydroxy-ethoxy)-imidazo[1,5-a]pyrazine-6-carboxamide A solution of 5-(4-bromo-2-fluorophenylamino)-N-(2-(vinyloxy)ethoxy)-imidazo[1,5-a]pyrazine-6-carboxamide (150 mg, 0.34 mmol) in methanol (4.5 mL) and dichloromethane (8.9 mL) was added 4M HCl in 1,4-dioxane (0.13 mL, 0.5 mmol, 1.5 eq.), and the reaction mixture was stirred at ambient temperature under $N_2$ for 1 h. Solid sodium carbonate (50 mg) was added to the reaction mixture. The reaction mixture was absorbed onto silica and then subjected to flash chromatography (Si-PPC, gradient 0% to 15%, methanol in dichloromethane) to afford the title compound as a white solid. (112.1 mg, 79.5%). $^1$H NMR (DMSO-$d_6$, 400 MHz) δ ppm 11.85 (broad s, 1H), 10.32 (broad s, 1H), 8.83 (s, 1H), 7.97 (s, 1H), 7.92 (s, 1H), 7.64 (dd, J=10.4 Hz, 2.6 Hz, 1H), 7.30 (d, J=8.8 Hz, 1H), 6.77 (t, J=8.8 Hz, 1H), 4.68 (t, J=5.6 Hz, 1H), 3.89 (t, 4.8 Hz, 2H), 3.59 (q, J=5.4 Hz, 2H); LCMS (method D1): $R_T$=0.786 min, [M+H]$^+$=410/412.

Example 23

(S)-5-(4-Bromo-2-fluorophenylamino)-N-(2-hydroxy-propoxy)imidazo[1,5-a]pyrazine-6-carboxamide

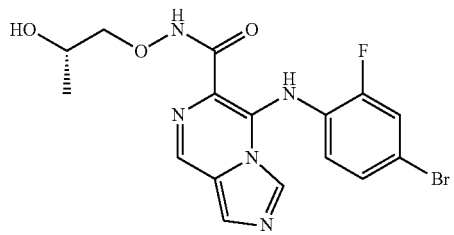 [SMILES: C[C@H](O)CONC(=O)c1ncc2cncn2c1Nc1ccc(Br)cc1F]

Step 1: 5-(4-Bromo-2-fluorophenylamino)imidazo[1,5-a]pyrazine-6-carboxylic acid

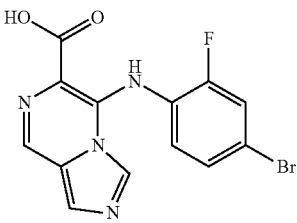 [SMILES: O=C(O)c1ncc2cncn2c1Nc1ccc(Br)cc1F]

The desired compound was prepared in an analogous fashion to 5-(2-fluoro-4-iodo-phenylamino)-imidazo[1,5-a]pyrazine-6-carboxylic acid, using 5-(4-bromo-2-fluoro-phenylamino)-imidazo[1,5-a]pyrazine-6-carboxylic acid methyl ester as the starting material. LCMS (method D1): $R_T$=0.713 min, [M+H]$^+$=351/353.

Step 2: (S)-5-(4-Bromo-2-fluorophenylamino)-N-(2-hydroxy-propoxy)imidazo[1,5-a]pyrazine-6-carboxamide To a solution of 5-(4-bromo-2-fluorophenylamino)imidazo[1,5-a]-pyrazine-6-carboxylic acid (100 mg, 0.28 mmol)

in anhydrous DMF (1.5 mL) was added, in order, (S)-1-aminooxy-propan-2-ol hydrochloride (37.4 mg, 0.29 mmol, 1.03 eq.), HOBt (40.4 mg, 0.30 mmol, 1.05 eq.), EDCI (57.3 mg, 0.30 mmol, 1.05 eq.), and 4-methylmorpholine (0.15 mL, 1.36 mmol, 4.8 eq.). The reaction mixture was stirred at room temperature under $N_2$ for 7 h and then diluted with ether (25 mL) and ethyl acetate (25 mL). The organic layer was washed with water and brine, dried ($Na_2SO_4$), filtered and concentrated in vacuo. The resultant residue was subjected to flash chromatography (Si-PPC, gradient 0 to 40% methanol in ethyl acetate) to give an oil. Crystallization from DCM ether hexane afforded the desired product as a white solid (30.3 mg, 25.0%). $^1$H NMR (DMSO-$d_6$, 400 MHz) δ ppm 11.88 (broad s, 1H), 10.29 (broad s, 1H), 8.82 (s, 1H), 7.98 (s, 1H), 7.92 (s, 1H), 7.65 (dd, J=10.6 Hz, 2.2 Hz, 1H), 7.30 (d, J=8.6 Hz, 1H), 6.78 (t, J=8.4 Hz, 1H), 4.80 (d, J=4.0 Hz, 1H), 3.90-3.81 (m, 1H), 3.75-3.62 (m, 2H), 1.05 (d, J=6.4 Hz, 3H); LCMS (method D2): $R_T$=1.516 min, $[M+H]^+$=424/426.

Example 24

(R)-5-(4-Bromo-2-fluorophenylamino)-N-(2,3-dihydroxy-propoxy)imidazo[1,5-a]pyrazine-6-carboxamide

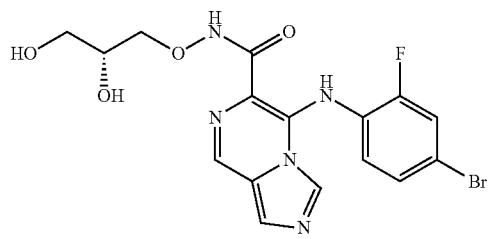 [SMILES: O=C(NOC[C@H](O)CO)c1ncc2cncn2c1Nc1ccc(Br)cc1F]

Step 1: (R)-5-(4-Bromo-2-fluorophenylamino)-N4(2,2-dimethyl-1,3-dioxolan-4-yl)methoxy)imidazo[1,5-a]pyrazine-6-carboxamide

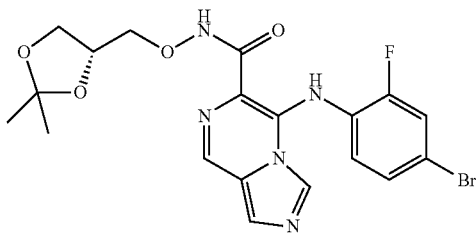 [SMILES: CC1(C)OC[C@H](CONC(=O)c2ncc3cncn3c2Nc2ccc(Br)cc2F)O1]

The desired compound was prepared in an analogous fashion to 5-(4-bromo-2-fluorophenylamino)-N-(2-(vinyloxy)ethoxy)-imidazo[1,5-a]pyrazine-6-carboxamide, using (R)—O((2,2-dimethyl-1,3-dioxolan-4-yl)methyphydroxylamine as the starting material. LCMS (method D1): $R_T$=0.954 min, $[M+H]^+$=480/482.

Step 2: 5-(4-Bromo-2-fluorophenylamino)-N-(2-hydroxy-ethoxy)-imidazo[1,5-a]pyrazine-6-carboxamide The desired compound was prepared in an analogous fashion to 5-(4-bromo-2-fluorophenylamino)-N-(2-hydroxy-ethoxy)-imidazo[1,5-c]pyrazine-6-carboxamide, using (R)-5-(4-bromo-2-fluorophenylamino)-N-((2,2-dimethyl-1,3-dioxolan-4-yl)methoxy)imidazo[1,5-a]pyrazine-6-carboxamide as the starting material. $^1$H NMR (DMSO-$d_6$, 400 MHz) δ ppm 11.90 (broad s, 1H), 10.38 (broad s, 1H), 8.81 (s, 1H), 7.96 (s, 1H), 7.91 (s, 1H), 7.65 (d, J=10.4 Hz, 1H), 7.30 (d, J=8.4 Hz, 1H), 6.77 (t, J=8.8 Hz, 1H), 4.87 (s, 1H), 4.56 (broad s, 1H), 3.93 (dd, J=9.6 Hz, 3.2 Hz, 1H), 3.79-3.69 (m, 2H), 3.43-3.35 (m, 2H); LCMS (method D1): $R_T$=0.724 min, $[M+H]^+$=440/442.

Example 25

5-(4-Bromo-2-fluorophenylamino)-N-(cyclopropylmethoxy)imidazo[1,5-a]pyrazine-6-carboxamide

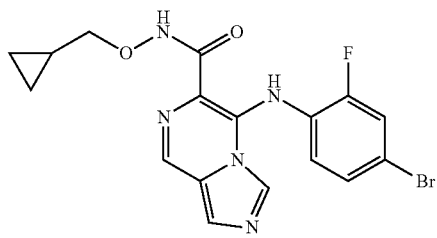 [SMILES: O=C(NOCC1CC1)c1ncc2cncn2c1Nc1ccc(Br)cc1F]

The title compound was prepared in an analogous fashion to N-(cyclopropylmethoxy)-5-(2-fluoro-4-iodophenylamino)imidazo[1,5-a]pyrazine-6-carboxamide, using 5-(4-bromo-2-fluoro-phenylamino)-imidazo[1,5-a]pyrazine-6-carboxylic acid methyl ester as the starting material. $^1$H NMR (MeOD, 400 MHz) δ ppm 8.74 (s, 1H), 7.87 (s, 1H), 7.84 (s, 1H), 7.48 (dd, J=10.4 Hz, 3.2 Hz, 1H), 7.30 (d, 8.4 Hz, 1H), 6.75 (t, J=8.4 Hz, 1H), 3.79 (d, J=7.2 Hz, 2H), 1.26-1.13 (m, 1H), 0.62-0.55 (m, 2H), 0.36 to 0.30 (m, 2H); LCMS (method D1): $R_T$=0.985 min, $[M+H]^+$=420/422.

I claim:

1. A compound 5-(2-fluoro-4-iodophenylamino)-imidazo[1,5-a]pyridine-6-carboxylic acid(2-hydroxyethoxy)-amide, or a pharmaceutically acceptable salt thereof.

2. The compound of claim 1 where the compound is a free base.

* * * * *